US012788723B2

(12) United States Patent
Brisander et al.

(10) Patent No.: US 12,788,723 B2
(45) Date of Patent: *Nov. 10, 2026

(54) FAST DISSOLVING PHARMACEUTICAL COMPOSITIONS

(71) Applicant: XSPRAY PHARMA AB, Solna (SE)

(72) Inventors: Magnus Brisander, Ekerö (SE); Thomas Meijer, Segeltorp (SE); Victor Söderberg, Uppsala (SE)

(73) Assignee: XSPRAY PHARMA AB, Solna (SE)

( * ) Notice: Subject to any disclaimer, the term of this patent is extended or adjusted under 35 U.S.C. 154(b) by 450 days.

This patent is subject to a terminal disclaimer.

(21) Appl. No.: 18/359,973

(22) Filed: Jul. 27, 2023

(65) Prior Publication Data

US 2024/0024248 A1 Jan. 25, 2024

Related U.S. Application Data

(63) Continuation-in-part of application No. 18/064,383, filed on Dec. 12, 2022, which is a continuation-in-part of application No. 17/580,768, filed on Jan. 21, 2022, now Pat. No. 11,529,351.

(60) Provisional application No. 63/288,752, filed on Dec. 13, 2021, provisional application No. 63/140,003, filed on Jan. 21, 2021.

(51) Int. Cl.

| | |
|---|---|
| ***A61K 9/28*** | (2006.01) |
| ***A61K 31/506*** | (2006.01) |
| ***A61K 47/02*** | (2006.01) |
| ***A61K 47/12*** | (2006.01) |
| ***A61K 47/32*** | (2006.01) |

(52) U.S. Cl.

CPC .......... *A61K 9/2866* (2013.01); *A61K 31/506* (2013.01); *A61K 47/02* (2013.01); *A61K 47/12* (2013.01); *A61K 47/32* (2013.01)

(58) Field of Classification Search

None

See application file for complete search history.

(56) References Cited

U.S. PATENT DOCUMENTS

| | | | | |
|---|---|---|---|---|
| 10,799,459 | B1 | 10/2020 | Andersson et al. | |
| 11,529,351 | B2 | 12/2022 | Brisander et al. | |
| 2009/0118297 | A1 | 5/2009 | Simo | |
| 2016/0038496 | A1* | 2/2016 | Shu | A61K 47/38 514/262.1 |
| 2021/0236489 | A1* | 8/2021 | Wertz | A61K 31/4164 |
| 2023/0121325 | A1 | 4/2023 | Brisander et al. | |

FOREIGN PATENT DOCUMENTS

| | | |
|---|---|---|
| WO | 2013/105895 A1 | 7/2013 |
| WO | 2019/105894 A1 | 7/2013 |
| WO | 2017/108605 A1 | 6/2017 |

OTHER PUBLICATIONS

Budha et al., Drug absorption interactions between oral targeted anticancer agents and PPIs: is PH-dependent solubility the Achilles heel of targeted therapy?, Clin. Pharmacol. Ther. (2012) 92(2): 203-213; DOI: 10.1038/clpt.2012.73; Epub: Jun. 27, 2012; PMID: 22739140;2012 ("Budha").

Buehler G. History of bioequivalence for critical dose drugs, Office of Pharmaceutical Science, U.S. Food and Drug Administration, Archived Document, 2010 ("Buehler").

Chandani et al Atypical pharmacokinetic profiles observed with dasatinib reference listed drug product in bioequivalence studies American Association of Pharmaceutical Scientists (AAPS) Annual Meeting, San Diego, Nov. 12-15, 2017 (Poster M6107) ("Chandani").

Dasatinib Dissolution Method, www.accessdata.fda.gov/scripts/cder/dissolution searching for dasatinib, last accessed on Jan. 19, 2022.

Eley et al., Phase I study of the effect of gastric acid pH modulators on the bioavailability of oral dasatinib in healthy subjects, J. Clin. Pharmacol. (2009) 49(6): 700-709; DOI: 10.1177/0091270009333854; Epub Apr. 24, 2009; PMID: 19395585. ("Eley").

Guidance for Industry, ANDAs: Stability Testing of Drug Substances and Products, Jun. 2013 ("GFI, Stability Testing").

Guidance for Industry, Assessing the Effects of Food on Drugs in INDs and NDAs—Clinical Pharmacology Considerations, Feb. 2019 ("GFI, Assessing Food Effects").

Guidance for Industry, Dissolution Testing and Acceptance Criteria for Immediate-Release Solid Oral Dosage Form Drug Products Containing High Solubility Drug Substances, Aug. 2018 ("GFI, Dissolution Testing").

Guidance for Industry, Evaluation of Gastric pH-Dependent Drug Interactions With Acid-Reducing Agents: Study Design, Data Analysis, and Clinical Implications, Nov. 2020 ("GFI, Evaluation of Gastric pH").

Guidance for Industry, Food-Effect Bioavailability and Fed Bioequivalence Studies, Dec. 2002 ("GFI, Food Effect").

Indini, Impact of Use of Gastric-Acid Suppressants and Oral Anti-Cancer Agents on Survival Outcomes: A Systematic Review and Meta-Analysis, Cancers (2020) 12(4): 998 (1-14). DOI: 10.3390/cancers12040998. Epub Apr. 18, 2020. PMID: 32325628.

Larfors et al. Increased Risk of Chronic Myeloid Leukemia Following Gastric Conditions Indicating Helicobacter pylori Infection: A Case-Control Study, Cancer Epidemiol. Biomarkers Prev. (2020) 29(1):151-156; DOI: 10.1158/1055-9965. EPI-19-0758; Epub Oct. 16, 2019; PMID: 31619405 ("Larfors").

Lassman et al., Phase 2 trial of dasatinib in target-selected patients with recurrent glioblastoma (RTOG 0627), Neuro-Oncology (2015) 17(7): 992-998 ("Lassman").

(Continued)

*Primary Examiner* — Susan T Tran

(74) *Attorney, Agent, or Firm* — Merchant & Gould P.C.; Daniel R. Evans

(57) ABSTRACT

The present disclosure relates to the field of pharmaceutical compositions. Furthermore, the present invention relates to an immediate release pharmaceutical composition in the form of a non-effervescent tablet composition comprising dasatinib and a gas generating agent.

20 Claims, 19 Drawing Sheets

(56) References Cited

OTHER PUBLICATIONS

Pang et al., Pharmacokinetics and absorption of the anticancer agents dasatinib and GDC-0941 under various gastric conditions in dogs—reversing the effect of elevated gastric pH with betaine HCl, Mol. Pharm. (2013) 10(11): 4024-4031; DOI: 10.1021/mp400356m; Epub Sep. 11, 2013; PMID: 23980865 ("Pang").
Robbins J et al., Dysphagia Research in the 21st Century and Beyond: Proceedings From Dysphagia Experts Meeting, Aug. 21, 2001, J. Rehab. Res. Devel. (2001) 39(4): 543-548 ("Robbins").
Shara et al., The concomitant use of tyrosine kinase inhibitors and proton pump inhibitors: Prevalence, predictors, and impact on survival and discontinuation of therapy in older adults with cancer, Cancer (2019) 125(7): 1155-1162; DOI: 10.1002/cncr.31917; Epub Jan. 3, 2019; PMID: 30605231 ("Sharma").
Smelick et al., Prevalence of Acid-Reducing Agents (ARA) in Cancer Populations and ARA Drug-Drug Interaction Potential for Molecular Targeted Agents in Clinical Development, Molecular Pharmaceutics (2013) 10(11): 4055-4062; DOI: doi.org/10.1021/mp400403s. Epub Sep. 13, 2013 ("Smelick").
Sprycel Prescribing Information for NDA 021986, Supplement 25 (Revised Jun. 29, 2021) ("Sprycel Label").
Sprycel Clinical Pharmacology and Biopharmaceutics Review for NDAs 21986 and 22072, Jun. 27, 2006 ("Sprycel Clinical Review").
Code of Federal Regulations Title 21, vol. 5, dated Oct. 1, 2021; 109 Pages (21 CFR 314.3(b)).
Dec. 30, 2020 Xspray Press Release, Xspray Pharma reports positive results from a study with dasatinib during omeprazole treatment.
Sep. 25, 2020 Xspray Press Release, Xspray announces positive preliminary results from the study for its lead product candidate HyNap-Dasa.
International Search Report and Written Opinion dated May 3, 2022 cited in Application No. PCT/EP2022/051343; (15 pages).
Imbruvica® Canadian monograph (2018), 59 pages.
Michael reaction—Wikipedia (2022), 6 pages.
LoPachin et al., Molecular mechanism of acrylamide neurotoxicity: lessons learned from organic chemistry, Environ. Health Perspectives (2012) 120(12): 1650-1657.
Sprycel® Canadian monograph (2021), 71 pages.
Aulton, M., Properties of solutions, Chapter 3 (pp. 33-40) in Pharmaceutics: The Science of Dosage Form Design (M. E. Aulton ed., 2nd Edition, 2002).
Harvard Lecture Notes is available online at canvas.harvard.edu/courses/775/files/108069/download?verifier=y2b5tTzPLktFlqfqXkCKtlwYZ1UHXFC9GqMMKEPA&wrap=1, last accessed on Jun. 28, 2022.
Spruance et al., Hazard Ratio in Clinical Trials, Antimicrob Agents Chemother. (2004) 48(8): 2787-2792 ("Spruance").
Miura M., Therapeutic drug monitoring of imatinib, nilotinib, and dasatinib for patients with chronic myeloid leukemia, Biol. Pharm. Bull. (2015) 38(5): 645-654.
Rousselot et al., Dasatinib dose optimisation based on therapeutic drug monitoring reduces pleural effusion rates in chronic myeloid leukaemia patients, Br. J. Haemotol. (2021) 194: 393-402 ("Rousselot").
Wang et al., Differential effects of dosing regimen on the safety and efficacy of dasatinib: retrospective exposure-response analysis of a Phase III study, Clin. Pharmacol. (2013) 5(1): 85-97 ("Wang").
Phyrago® Prescribing Information, as of Dec. 5, 2023 (35 pp.).

* cited by examiner

| Formulation (Dose) | > 50 ng/mL | | ≤ 50 ng/mL | | C24h (ng/mL) [All Subjects] | | | | | |
|---|---|---|---|---|---|---|---|---|---|---|
| | Cmax | C2h | Cmax | C2h | > 1.5 | ≤ 1.5 | > 2.5 | ≤ 2.5 | > 2.61 | ≤ 2.61 |
| Test (100 mg) | 208 (100%) | 205 (99%) | 0 (0%) | 3 (1%) | 206 (99%) | 2 (1%) | 119 (57%) | **89 (43%)** | 111 (53%) | 97 (47%) |
| Sprycel (140 mg) | 197 (96%) | 193 (94%) | 9 (4%) | 13 (6%) | 203 (99%) | 3 (1%) | 154 (75%) | **52 (25%)** | 145 (70%) | 61 (30%) |
| Test (70 mg)* | 207 (100%) | 200 (96%) | 1 (0%) | 8 (4%) | 156 (75%) | **52 (25%)** | 45 (22%) | **163 (78%)** | 40 (19%) | 168 (81%) |
| Reference (100 mg)* | 196 (95%) | 186 (90%) | 10 (5%) | 20 (10%) | 183 (89%) | **23 (11%)** | 80 (39%) | **126 (61%)** | 73 (35%) | 133 (65%) |

*Estimated plasma concentration values (Cmax, C2h, and C24h) from observed values.

FIG. 18

FAST DISSOLVING PHARMACEUTICAL COMPOSITIONS

RELATED APPLICATIONS

This application is a continuation-in-part of U.S. patent application Ser. No. 18/064,383, filed on Dec. 12, 2022, which is a continuation-in-part of U.S. patent application Ser. No. 17/580,768, filed on Jan. 21, 2022, now U.S. Pat. No. 11,529,351, which claims priority to U.S. Provisional Patent Application Nos. 63/140,003, filed on Jan. 21, 2021, and 63/288,752, filed on Dec. 13, 2021, the subject matter of which is incorporated by reference.

FIELD

Disclosed herein is an immediate release pharmaceutical composition in the form of a non-effervescent tablet comprising dasatinib and a gas generating agent.

BACKGROUND

Drugs that are delivered orally via a tablet should ideally be readily soluble in water. Drugs that are poorly water-soluble tend to pass through the gastrointestinal tract before they can fully dissolve, and this typically leads to poor bioavailability of the drug. Unfortunately, many drugs currently on the market or in development are poorly water-soluble, and this presents a serious challenge to the pharmaceutical industry.

A major objective of formulation chemistry is to improve drug efficiency and safety, by e.g. improving bioavailability and stability as well as convenience to the patient. Bioavailability means the rate and extent to which an active substance or drug is absorbed from a pharmaceutical form and becomes available at the site of action. The most common and preferred method of delivery due to convenience, ease of ingestion, and high patient compliance to treatment is the oral route of drug delivery. However, for many drugs, drug absorption from the gastrointestinal tract is limited by poor aqueous solubility and/or poor membrane permeability of the drug molecules.

Tablet production is an essential operation for the pharmaceutical industry. Tablet presses operating on the principle of direct compression have been functioning for decades. However, formulations that process well in these units to consistently deliver uniform tablets with the required properties remain an ongoing challenge. Producing good quality tablets requires manipulation of variables such as particle size and shape, surface texture and moisture content, to control both compactibility and the flow properties of the blend. Excipients are often used to enhance drug properties and processability. The aim is to develop a formulation with optimal rheology that delivers high quality in combination with high productivity. Direct compression involves feeding of tablet ingredients to a press as a blended powder. The blend contains various components such as filler, binder, API, and lubricant; each of which fulfils a different function in terms of tablet or processing performance. Tablet quality is quantified in terms such as strength, weight, dimensions, and API content, the required properties being produced through control of variables such as flowability and tabletability of the mix. This is achieved by addressing fundamental issues such as excipient choice and the concentration of each component in the final formulation.

For a drug to be absorbed from a solid dosage form after oral administration, it must first be in solution, and the first important step toward this condition is usually the break-up of the tablet; a process known as disintegration, as depicted in FIG. 1.

Wetting is the ability of a liquid to maintain contact with a solid surface, resulting from intermolecular interactions when the two are brought together. The degree of wetting (wettability) is determined by a force balance between adhesive and cohesive forces.

Although disintegrants are important components in solid dosage forms, their mechanism of action has not been clearly elucidated. However, wetting is an important and early part of the mechanism of action for a disintegrant. The mechanisms proposed in the past include water wicking, swelling, deformation recovery, repulsion, heat of wetting and even dissolution of a fast dissolving material can be considered as a passive disintegration mechanism. It seems likely that no single mechanism can explain the complex behavior of the disintegrants. However, each of these proposed mechanisms provides some understanding of different aspects of disintegrant action.

Most immediate release oral drug products, such as tablets and capsules, are formulated to release the active drug immediately after oral administration. For immediate release solid oral drug products containing a high solubility drug substance (as defined herein), the dissolution criterion is Q=80% in 30 minutes (see GFI, Dissolution Testing).

Drug product is a finished dosage form, e.g., tablet, capsule, or solution, that contains a drug substance, generally, but not necessarily, in association with one or more other ingredients (defined in 21 CFR 314.3(b)).

Background Regarding Generic Drugs

A generic drug must contain the same active pharmaceutical ingredient as the original brand name product, but it may differ in characteristics such as manufacturing process, formulation, excipients, color, taste, and packaging.

Drug companies can submit an abbreviated new drug application (ANDA) to U.S. Food and Drug Administration (FDA) for approval to market a generic drug that is the same as (or bioequivalent to) the brand-name product. FDA's Office of Generic Drugs reviews the application to make certain drug companies have demonstrated that the generic medicine can be substituted for the brand-name medicine.

An ANDA must show that the generic medicine is equivalent to the brand in at least the following ways:

- i) The active ingredient is the same as that of the brand-name drug/innovator drug.
- ii) The generic medicine is the same strength.
- iii) The medicine is the same type of product (such as a tablet or an injectable).
- iv) The medicine has the same route of administration (such as oral or topical).
- v) It has the same use indication.
- vi) The inactive ingredients of the medicine are acceptable.

Some differences, which must be shown to have no effect on how the medicine functions, are allowed between the generic and the brand-name version.

The FDA defines bioequivalence as the absence of a significant difference in the rate and extent to which the active ingredient becomes available when administered at the same molar dose under similar conditions in an appropriately designed study.

In order to determine bioequivalence, a randomized, crossover trial is conducted with both the generic drug being assessed and the brand-name drug as the control. In these studies, a number of pharmacokinetic (PK) parameters are assessed, including maximum plasma concentration of a drug (Cmax) and drug plasma exposure over time (or area under the curve, (AUC)).

These parameters help assess how the rate and extent of the availability of the generic drug compares to the control. As the FDA requires, there must be no significant difference in the rate and extent to be deemed bioequivalent.

According to current regulatory (viz., FDA and European Medicines Agency) guidance documents, bioequivalence can be declared when the 90% confidence interval (CI) for the ratio of mean values for Cmax and AUC for generic drug vs. original drug falls within the interval 80-125%, as evaluated in a randomized, cross-over trial. Highly variable drugs (intra-subject variability of 30% or more) are allowed a wider acceptance interval.

The confidence interval is dependent on both the point estimate for the ratio of mean values and on the variability between subjects in the PK parameter for each product. The larger the deviation in point estimate for the ratio from the value 1.0 and the larger the variability in the PK parameter between subjects for each product, the more unlikely it becomes that bioequivalence criteria will be met.

A ratio of mean values for Cmax and AUC for generic drug vs. original drug below or above 1.1 will typically result in a 90% confidence interval outside 80-125% unless the variability in Cmax and AUC between subjects is very low. Therefore, the bioequivalence criteria are very strict and require that both the ratio of mean values is close to 1.0 and that the variability between subjects is limited.

According to an FDA study, the mean difference for AUC values between test and reference products was found to be 3.5% in the 2-year period following the Waxman-Hatch Act (see Buehler).

In other words, it is a misconception that the FDA allows the strength of the tablet or a PK parameter, to vary from 80%-125%. The mean PK value of the generic drug must be quite close to that of the reference drug for the ratio of the PK values (AUC and Tmax) to be close to 1.00 which implies comparable bioavailability. If the ratio is not close to 1.00, then the 90% CI of ratio is unlikely to lie between 0.80 and 1.25.

Assessment of bioequivalence (BE) for highly variable drugs is challenging. Reference-scaled average bioequivalence (RSABE) is a statistical methodology that is increasingly used to demonstrate bioequivalence for highly variable drugs (HVDs). A drug product is called highly variable if the intra-subject (aka, within-subject) variability is greater than 30% C.V. (coefficient of variation) in the pharmacokinetic measures of AUC and/or Cmax. In other words, if you take the same drug in two different occasions at similar conditions (e.g., same dosage, administration route, fasted, same time a day, etc.)

you would expect the measured AUC and Cmax to be very similar regardless of the time of administration. However, if instead the rate and extend of absorption differ by more than 30% between the occasions then the drug is considered highly variable. In those cases, running conventional average bioequivalence (ABE) with the standard sample size will likely fail to show bioequivalence due to the intrinsic variability even if the products were comparable. Indeed, some HVDs have failed to show bioequivalence to itself using standard ABE sample sizes. For HVDs, studies designed to show bioequivalence may need to enroll large numbers of subjects, even when the formulations themselves have no significant mean differences. This increases the expense of BE studies, places more subjects at risk, and ultimately, limits the availability of generics.

The RSABE method allows to scale the acceptance bioequivalence window based on the within subject variability of the reference drug. Thus, the limits of the conventional average bioequivalence (ABE) can be scaled to the reference variability (i.e., the permitted window increases as the variability increases). RSABE methods can be applied to show bioequivalence if the within subject variability for the reference drug has been shown to have at least 30% CV.

Specifics of RSABE methodology vary between regulatory agencies. Simply stated, the RSABE may be employed if the reference product within-subject variability, $CV_{WR}$, is greater than 30%, which corresponds to a within-subject standard deviation $S_{WR} \geq 0.294$.

As related to AUC, if $S_{WR} \geq 0.294$, then RSABE may be permitted and acceptance criteria for 90% CI may be widened. The point estimate (or geometric mean ratio) must be within 80-125% regardless of the widened acceptance criteria.

As related to Cmax, if $S_{WR} \geq 0.294$, then RSABE may be permitted and acceptance criteria for 90% CI may be widened. The point estimate (or geometric mean ratio) must be within 80-125% regardless of the widened acceptance criteria.

In addition, most regulatory authorities would look at the intra-subject variability for the two products and ask questions if there was a marked difference between them. Products satisfying the bioequivalence requirements can reliably be assumed to produce similar clinical effects when used interchangeably in the same patient.

In addition, most regulatory authorities would look at the intra-subject variability for the two products and ask questions if there was a marked difference between them. Products satisfying the bioequivalence requirements can reliably be assumed to produce similar clinical effects when used interchangeably in the same patient.

There is thus a high medical need and high commercial incentives for companies to develop a drug that is considered a generic drug according to the relevant national regulatory standards. Such regulatory standards are high and difficult to meet since safety and efficacy is a major concern for all regulatory authorities. It is thus a major challenge to develop a drug that is considered fully bioequivalent and substitutable for the reference listed drug (RLD).

It is well established that for example Sprycel (dasatinib monohydrate) has a high PK variability. Lassman discloses that dasatinib exposure is known to be quite variable within and between patients, with coefficients of variation of up to 100% for both AUC and Cmax.

There is notable interindividual heterogeneity in drug response, affecting both drug efficacy and toxicity, resulting in patient harm and the inefficient utilization of limited healthcare resources. It has been reported that the proportion of patients who respond beneficially to the first drug offered in the treatment of a wide range of diseases is typically just 50-75%. Drug absorption is an important component of drug response where interindividual variability leads to patient harm and the excessive and inefficient use of limited healthcare resources.

There is thus an unmet need for a pharmaceutical composition that is bioequivalent to Sprycel (dasatinib monohydrate), but with fewer drawbacks like inter- or interindividual variation, food interaction, bioavailability dependent of gastric transit time and the like.

A drug interaction is a change in the action or side effects of a drug caused by concomitant administration with a food, beverage, supplement, or another drug. The majority of clinically relevant food-drug interactions are caused by food-induced changes in the bioavailability of the drug. Since the extent of a food effect on oral bioavailability strongly depends on the type and composition of the food as well as on the dietary protocol during the study, the FDA issued a guidance in 2002 for conducting bioavailability and bioequivalence studies under fed conditions (GFI, Food Effect). This so-called FDA standard meal meanwhile represents the general standard for food effect studies and therefore, the majority of pharmacokinetic data on food effects that were published are based on this particular meal. The final evaluation of the food effect is based on the 90% confidence intervals of the ratios of AUC and Cmax obtained following drug administration under fasted and fed conditions. According to the ratio of the AUC determined after fasting and after fed drug administration, positive (increased oral bioavailability) and negative (reduced oral bioavailability) food effects are distinguished.

Concomitant use of antacid preparations including proton pump inhibitor (PPIs) with other medications is common. The potential for antacid-drug interactions is dependent upon the chemistry and physical properties of the antacid preparation and might be increased if the API has a pH-dependent solubility. These pH-dependent solubility differences might lead to pH-dependent dissolution profiles. Many APIs, like dasatinib, are known to have a pH-dependent solubility. However, the physical form of the API and/or the pharmaceutical excipients used in the final drug product, may decrease or even diminish the pH-dependent solubility of the API. It is advantageous if the final drug product shows a small, or non-existing, pH-dependent dissolution profile.

Further, while generic formulations of drug products are required to be both pharmaceutically and therapeutically equivalent to a RLD, the FDA is also concerned that differences in physical characteristics (e.g., size and shape of the tablet) may affect patient compliance and acceptability of medication regimens or could lead to medication errors. Thus, the FDA recommends that generic drug manufacturers consider physical attributes when they develop quality target product profiles (QTPPs) for their generic product candidates.

Size

Difficulty swallowing tablets and capsules can be a problem for many individuals and can lead to a variety of adverse events and patient non-compliance with treatment regimens. It is estimated that over 16 million people in the United States have some difficulty swallowing, also known dysphagia (see Robbins). For these individuals, swallowing a tablet or a capsule can be particularly challenging. A survey of adults on difficulties swallowing tablets and capsules suggests that this problem goes well beyond the patient population with clinically recognized dysphagia and may affect as many as 40 percent of Americans. Of those who experience difficulty swallowing medications, less than a quarter discuss the problem with a health care professional, 8 percent admit to skipping a dose of prescribed medication, and 4 percent have discontinued therapy because the tablets and/or capsules were difficult to swallow.

Size and shape of tablets and capsules also affect the transit of the product through the pharynx and esophagus. Larger tablets and capsules have been shown to have a prolonged esophageal transit time. This can lead to disintegration of the product in the esophagus and/or cause injury to the esophagus, resulting in pain and localized esophagitis and the potential for serious sequelae including ulceration, stricture, and perforation. Other adverse events such as pain, gagging, choking, and aspiration are related to swallowing difficulties in the oropharyngeal phase of swallowing and increasingly occur at larger tablet and capsule sizes.

For comparable ease of swallowing as well as patient acceptance and compliance with treatment regimens, the FDA recommends that generic oral tablets and capsules intended to be swallowed intact should be of a similar size to the corresponding RLD. The Agency recommends limiting size differences between therapeutically equivalent tablets as follows:

If the RLD is less than 17 mm in its largest dimension, the generic product should be:

- No more than 20 percent larger than the RLD in any single dimension (the resulting single dimension of the generic should not exceed 17 mm).
- No more than 40 percent larger than the volume of the RLD.

If the RLD is equal to or greater than 17 mm in its largest dimension, the generic product should be:

- No larger than the RLD in any single dimension.
- No larger than the volume of the RLD.

The FDA further recommends that the largest dimension of a tablet or capsule should not exceed 22 mm and that capsules should not exceed a standard 00 size.

Background on Solid Dispersions

In some instances, the pharmaceutical dosage form may be a solid dispersion. The term "solid dispersion" refers to a system in a solid state comprising at least two components, wherein one component, a drug substance, is dispersed throughout the other component or components. For example, the solid dispersion can be an amorphous solid dispersion.

The term "amorphous solid dispersion" (ASD) as used herein, refers to stable solid dispersions comprising amorphous drug substance and a polymeric stabilizing and matrix-forming component.

The term "polymeric stabilizing and matrix-forming component" refers to any polymer known to the skilled practitioner that is used to stabilize an amorphous drug substance in a solid dispersion.

Processes for making such solid dispersions are also available to the skilled practitioner and include, for instance, spray drying, melt extrusion, freeze drying, rotary evaporation, drum drying, or other solvent removal processes. In the spray drying process, the amorphous dispersion is formed by dispersing or dissolving the drug substance and the stabilizing polymer in a suitable solvent to form a feed solution, pumping the feed solution through a nozzle or atomizer into a drying chamber, and removing the solvent to form the amorphous solid dispersion powder in the drying chamber. A drying chamber uses gases, such as forced air, nitrogen, nitrogen-enriched air, or argon to dry particles. The feed solution can be atomized by conventional means well known in the art, such as a two-fluid sonicating nozzle and a two-fluid non-sonicating nozzle.

There is thus a high medical need and high commercial incentives for companies to develop a drug that is considered a generic drug according to the relevant national regulatory standards. Such regulatory standards are high and difficult to meet since safety and efficacy is a major concern for all regulatory authorities. It is thus a major challenge to develop a drug that is considered fully bioequivalent and substitutable for the RLD.

Further, the size limitation imposed by the FDA on generic drugs manufacturer adds an extra burden if a high amount of excipients and/or high amount of the active pharmaceutical ingredient is required in the tablet. The generic drug manufacturer is caught between a rock and a hard place. The generic manufacturer cannot add high amounts of disintegrant, in order to break up the tablet, without infringing on the size limitation. The present disclosure provides a solution to said problem, which is especially useful in the manufacture of so-called immediate release oral drug products.

The size limitation, enforced by the FDA, becomes extra burdensome when working with a solid dispersion, such as an amorphous solid dispersion, since the stabilizing polymer in the solid dispersion takes up space and weight, and sometimes even more space and weight compared to the API, such as dasatinib, when for example the drug load in the solid dispersion is below 50%, by weight.

SUMMARY

The present disclosure relates to dasatinib amorphous solid dispersions (ASDs), pharmaceutical compositions of dasatinib ASDs, and methods of use comprising administration of the pharmaceutical compositions of dasatinib ASDs. The dasatinib ASDs and the pharmaceutical compositions of the present disclosure may provide particular advantages over conventional crystalline dasatinib formulations, such as Sprycel.

Moreover, certain ASDs and pharmaceutical compositions of the present disclosure unexpectedly provide a pharmacokinetic profile similar to that of Sprycel, even when the dose of dasatinib administered by the pharmaceutical compositions is a fraction (e.g., from about 0.70 to about 0.75) of the dose of dasatinib normally administered when using Sprycel. Therefore, the disclosure provides pharmaceutical compositions that can be administered at a lower dose than Sprycel, but that would be expected to provide a comparable therapeutic effect.

As another advantage, pharmaceutical compositions of the disclosure may achieve a reduced inter-subject and/or intra-subject variability, as compared to the variability observed for Sprycel.

Thus, the ASDs and the pharmaceutical compositions of the present disclosure may offer a safer but equally effective presentation of dasatinib as compared to the currently available product, i.e., Sprycel.

BRIEF DESCRIPTION OF THE DRAWINGS

FIG. 18 provides individual plasma concentration values (Cmax, C2h, and C24h) observed from clinical study comparing Test Formulation (100 mg dasatinib, amorphous) and Reference Formulation (140 mg), as well as estimated individual plasma concentration values (Cmax, C2h, and C24h) for Test Formulation (70 mg dasatinib, amorphous) and Reference Formulation (100 mg).

Figure 1:
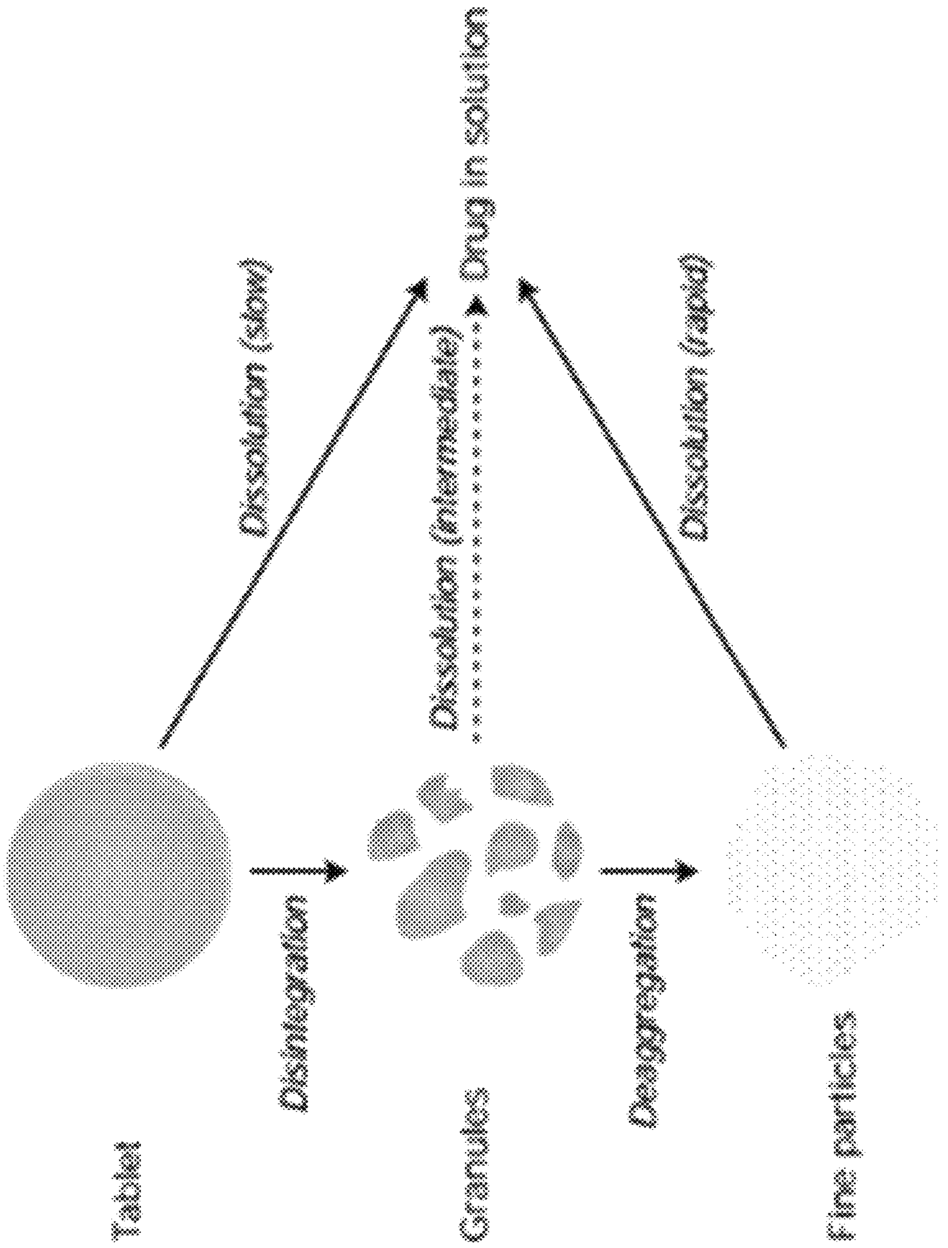
FIG. 1 depicts a generalized diagram showing selected processes available for tablet dissolution.
Figure 2:
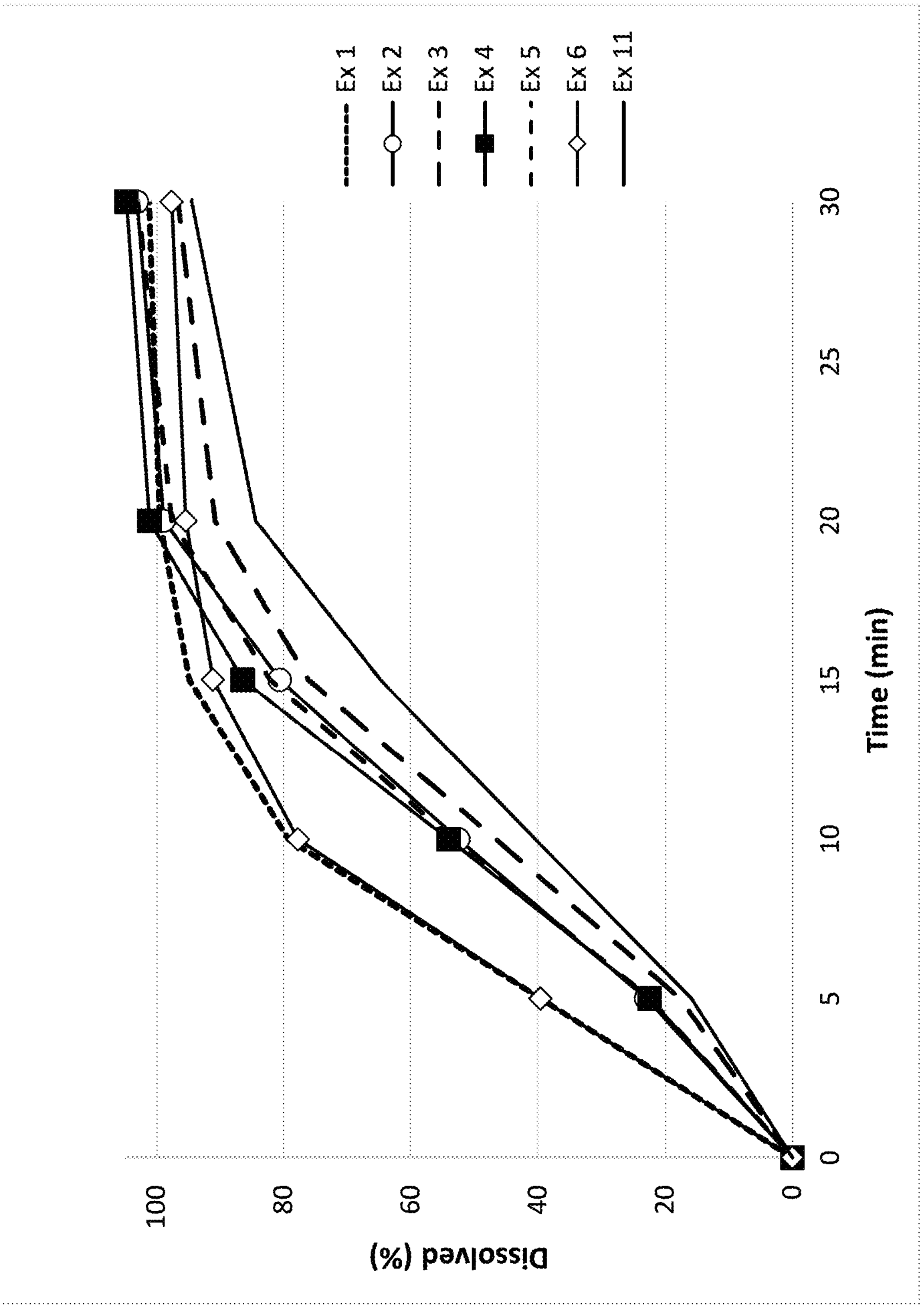
FIG. 2 provides results of a dissolution test, performed as per Ph. Eur. 2.9.3. apparatus II (paddles) at pH 2 using ultraviolet (UV) detection, of tablets prepared in Examples 1 to 6 and Example 11.
Figure 3:
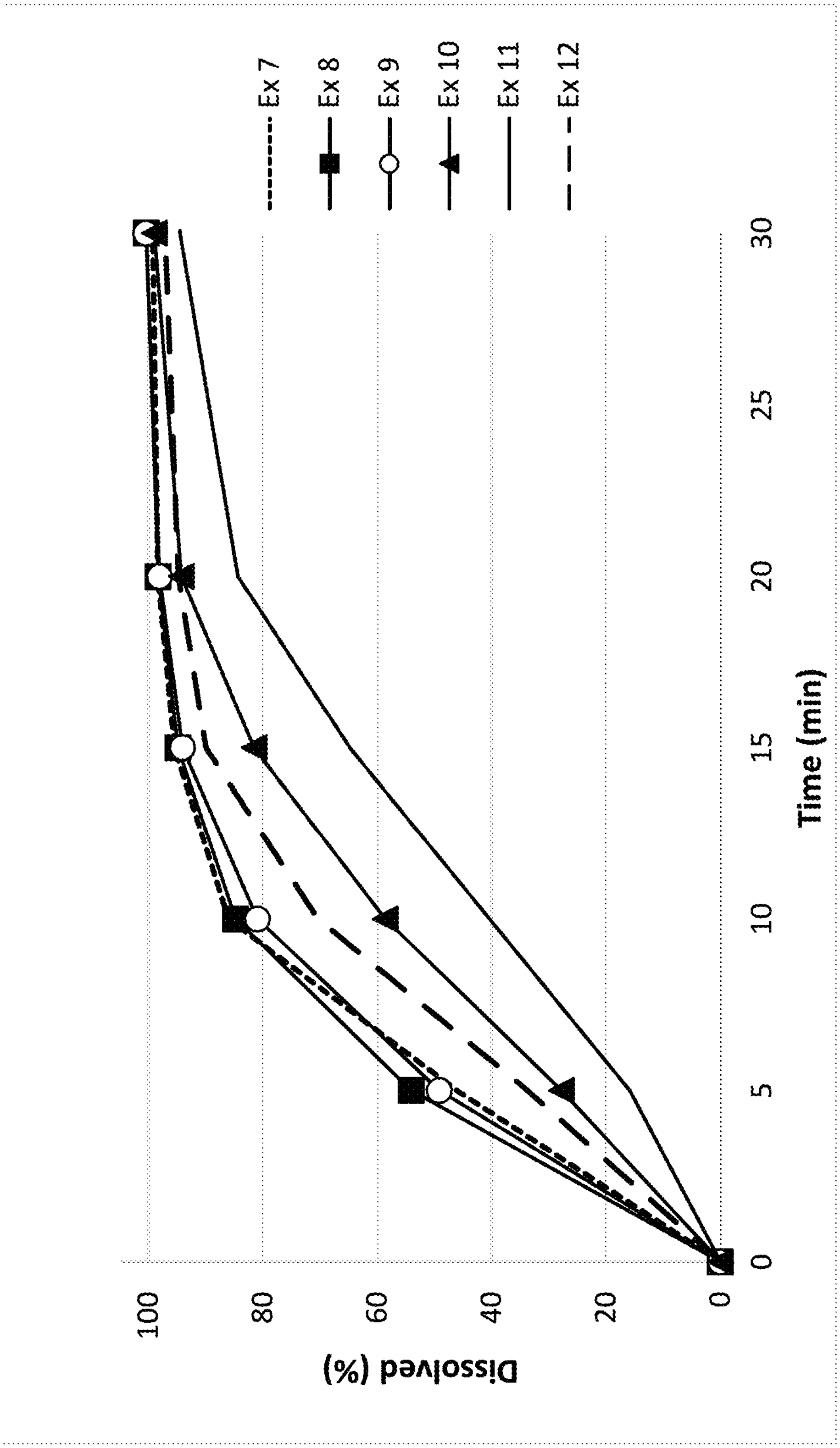
FIG. 3 provides results of a dissolution test, performed as per Ph. Eur. 2.9.3. apparatus II (paddles) at pH 2 using UV detection, of tablets prepared in Examples 7 to 12.
Figure 4:
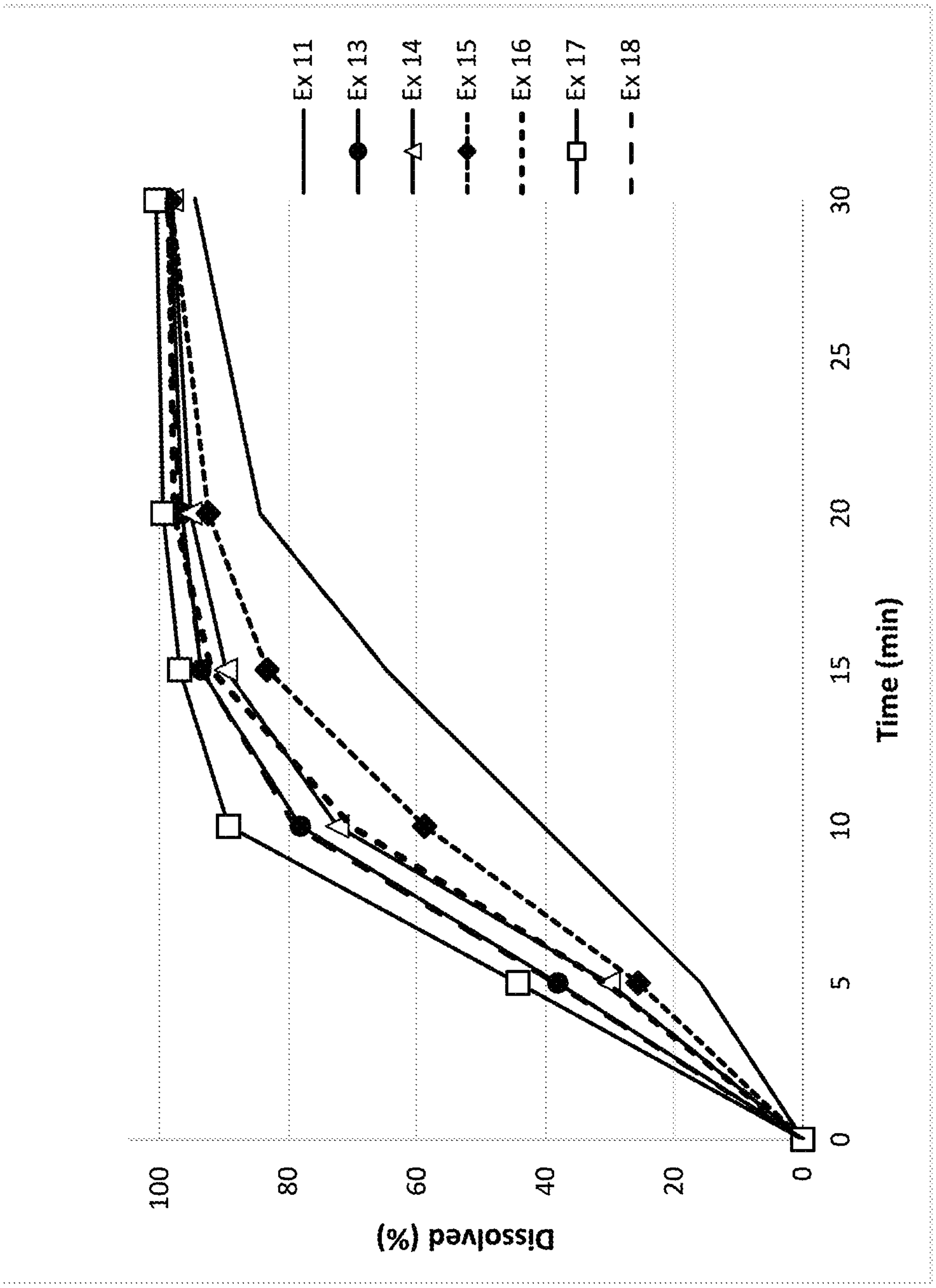
FIG. 4 provides results of a dissolution test, performed as per Ph. Eur. 2.9.3. apparatus II (paddles) at pH 2 using UV detection, of tablets prepared in Examples 13 to 18 and Example 11.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION

Disclosed herein is a pharmaceutical composition in the form of a non-effervescent tablet, comprising: (a) particles comprising (i) dasatinib in an amount of about 10% by weight to about 70% by weight of the particles; and (ii) at least one polymeric stabilizing and matrix-forming component; (b) at least one disintegrant agent in an amount of about 4% by weight to about 16% by weight; (c) at least one gas generating agent in an amount of about 8% by weight to about 16% by weight; (d) at least one acidic pH-modifier in an amount of about 2% by weight to about 6% by weight.

In one aspect, the particles comprise solid dispersion particles.

Solid dispersion particles may be produced by any conventional means, for instance, spray drying, melt extrusion, freeze drying, rotary evaporation, drum drying, or other solvent removal processes; or as is described in Xspray WO894 or Xspray WO895. An important characteristic of the system disclosed therein is that the two fluid streams should merge within a nozzle at an angle in the interval of from about 45° to about 135°, e.g., about 90°, and sprayed into a particle formation/separation function. In principle, the system allows for producing particles of predetermined size and/or morphology for example dasatinib as the active pharmaceutical ingredient and $CO_2$ as a fluid antisolvent under supercritical or subcritical conditions. The solid dispersion particles are dried by flushing $CO_2$ through the retained particles in order to extract any remaining solvent. The precipitation vessel is then depressurized and the particles can be collected.

Illustrative fluids which can be used as an antisolvent are a) gaseous at room temperature and atmospheric pressures, or b) liquid at room temperature and atmospheric pressure.

The antisolvent is typically selected for its ability to be readily dispersed into small droplets and for its ability to act as an atomizing agent and antisolvent against the dasatinib present in the solution.

Fluids according to group (a) may be selected from carbon dioxide (Pc=74 bar and Tc=31° C.) (preferred), nitrous oxide (Pc=72 bar and Tc=36° C.), sulphur hexafluoride (Pc=37 bar and Tc=45° C.), ethane (Pc=48 bar and Tc=32° C.), ethylene (Pc=51 bar and Tc=10° C.), xenon (Pc=58 bar and Tc=16° C.), trifluoromethane (Pc=47 bar and Tc=26° C.), chlorotrifluoromethane (Pc=39 bar and Tc=29° C.) and nitrogen (Pc=34 bar and Tc=−147° C.) and mixtures containing these compounds/elements. Pc stands for critical pressure and Tc for critical temperature.

Fluids according to group (b) are typically selected among conventional liquids of the same general types as discussed for solvents above but with the difference that the dasatinib present in the solution must be poorly soluble in the antisolvent. Particular liquids of group (b) comprise methanol, ethanol, acetone/water and mixtures containing one or more of these fluids.

The fluid antisolvents of group (a) above are typically used at pressures and temperatures providing i) supercritical conditions (supercritical fluid) or ii) a subcritical conditions (subcritical fluid) in the particle formation function and/or upstream of this function, such as in the mixing function and upstream of this latter function. With reference to the preceding paragraph, variant (i) means pressures and temperatures which are typically above the critical pressure Pc and critical temperature Tc of the antisolvent used. For the pressure this typically means pressures in the interval (1.0-7.0)×Pc or in the interval≥10 bar, suitably ≥20 bar with preference for ≥30 bar, higher than Pc with illustrative upper limits being 100 bar, 200 bar and 300 bar higher than Pc. For the temperature this typically means temperatures within (1.0-4.0)×Tc or in the interval of ≥5° C., suitably ≥10° C. with preference for ≥15° C. above Tc with illustrative upper limits being 10° C., 40° C. and 50° C. above Tc.

Variant (ii) means that at least one of temperature and pressure, with preference for only the temperature, is/are below the critical value; Tc and Pc, respectively. Thus, the temperature may be in the interval of (0.1-1)×Tc, such as (0.5-1)×Tc, or lower. Further, the temperature may be low, such as −10° C. or −30° C. These temperatures may be combined with pressures as defined in the preceding paragraph or with pressures lower than the Pc of the used antisolvent. For carbon dioxide this means that the temperature in the particle formation function is <+31° C., such as about +25° C. or lower combined with a pressure above or below 74 bar.

The antisolvents of group (b) above are typically used in the subcritical state, i.e. as a subcritical fluid.

A suitable solvent is an organic solvent selected from the group consisting of DMSO, trifluoroethanol, acetone, tetrahydrofuran, ethyl acetate, dimethylacetamide, or a mixture thereof.

In one aspect, the amount of an active pharmaceutical ingredient (e.g., dasatinib) in a solid dispersion ranges from about 10% by weight to about 70% by weight, such as about 20% by weight to about 60% by weight, such as about 30% by weight to about 50% by weight, or about 35% by weight to about 40% by weight.

A suitable "polymeric stabilizing and matrix-forming component" comprises, but is not limited to, methyl cellulose, ethyl cellulose, hydroxyethyl cellulose, hydroxypropyl cellulose (e.g. HPC ef, HPC lf and HPC jf), hydroxypropyl methylcellulose (e.g. Methocel E3 and E15 and Pharmacoat), hydroxypropyl methylcellulose acetate succinate (HPMC AS), hydroxypropyl methylcellulose phthalate (e.g. HPMCP-HP55), polyvinylpyrrolidone (e.g. PVP 30K and PVP 90K), polyvinyl acetate phthalate (PVAP), copolyvidone (aka copovidone, e.g. Kollidon VA 64), crospovidon (e.g. Kollidon CL), methacrylic acid and ethylacrylate copolymer (e.g. Kollicoat ME), methacrylate acid and methyl methacrylate copolymer (e.g. Eudragit L100), polyethylene glycol (PEG), DL lactide/glycolide copolymer, poly DL-lactide, cellulose acetate phthalate (CAP), aminoalkyl methacrylate copolymers (e.g. Eudragit RL100, RL PO or RS PO), carbomer homopolymer Type A (e.g. Carbopol 971P), carbomer homopolymer Type B (e.g. Carbopol 974P), or Poloxamers (e.g. Pluronics, Kolliphor), or mixtures thereof.

In another aspect, the amount of active pharmaceutical ingredient (e.g., dasatinib) in a solid dispersion (e.g., amorphous solid dispersion) ranges from about 30% by weight to about 35% by weight, including for example, about 31% by weight, about 32% by weight, about 33% by weight, and about 34% by weight, where remaining amount of solid dispersion comprises a polymeric stabilizing and matrix-forming component (e.g., copolyvidone).

In one aspect, dasatinib is 100% amorphous and at least one polymeric stabilizing and matrix-forming component is 100% amorphous, and thus, providing an amorphous solid dispersion.

In another aspect, dasatinib is 100% amorphous and the at least one polymeric stabilizing and matrix-forming component has an amorphicity of less than 100%.

The degree of amorphicity and/or crystallinity is generally measured using X-ray powder diffraction (XRPD). An amorphous solid does not display a definitive X-ray diffraction pattern with sharp maxima. The degree of amorphicity and/or crystallinity should be measured using conventional laboratory XRPD.

In one aspect, the composition may be conveniently administered in unit dosage form; for example containing from about 5 to about 200 mg of dasatinib, including all values in between, such as, for example, 10, 15, 20, 25, 30, 35, 36, 40, 45, 50, 55, 57, 65, 70, 75, 80, 85, 90, 95, 100, 105, 110, 115, 120, 125, 130, 135, 140, 145, 150, 155, 160, 165, 170, 175, 180, 185, 190, 195, or 200 mg of active ingredient per unit dosage form.

In yet another aspect, the pharmaceutical composition disclosed herein comprises dasatinib in an amount of about 15 mg, about 36 mg, about 50 mg, about 57 mg, about mg, or about 100 mg.

Pharmaceutical Composition Having Improved Variability

The pharmaceutical compositions of the present disclosure may, in some embodiments, provide a less variable in vivo pharmacokinetic performance compared to a reference listed drug (e.g., Sprycel).

As used herein, the phrase "improved variability composition" refers to a composition disclosed herein that exhibits a lower coefficient of variation with respect to one or more pharmacokinetic parameters when administered to an appropriate set of human subjects (e.g., healthy human subjects), as compared to the coefficient of variation observed for a conventional formulation of dasatinib (e.g., Sprycel) when administered under similar conditions. For this assessment, the set of human subjects should include a suitable number of subjects such that the study would be sufficiently powered to demonstrate bioequivalence, according to standard practices and relevant FDA guidelines.

In some embodiments, the improved variability composition provides a coefficient of variation with respect to at least one pharmacokinetic parameter that is 40% lower, 35% lower 30% lower, 25% lower, 20% lower, 15% lower, 10% lower, or 5% lower than the coefficient of variation observed for the standard commercial, composition of dasatinib (e.g., Sprycel) when administered under similar conditions. The pharmacokinetic parameter can be any of Cmax, AUC(last) (AUC up to the last measurable concentration and sometimes referred to as AUC(0-t), e.g., AUC(0-24h), and AUC (0-∞)). In some embodiments, the improved variability composition provides an improvement with respect to Cmax and at least one of AUC(last) and AUC(0-∞). In other embodiments, the improved variability composition provides an improvement with respect to each of Cmax, AUC (last), and AUC(0-∞).

In particular, it has been observed that compositions disclosed herein can provide a lower coefficient of variation for pharmacokinetic parameters when administered to human subjects (e.g., healthy human subjects) in a fasted state.

These results showed that dasatinib ASD according to the present disclosure can be used to increase dasatinib exposure in the fasted state, potentially facilitating a lower delivered dose and improved food effect profile compared to Sprycel.

Additionally, the reduced variability may result in a reduced occurrence of pleural effusion in CML patients. For instance, administration of a conventional crystalline dasatinib formulation (viz., Sprycel) shows that CML patients may exhibit pleural effusion, as evidenced by Section 5.3 of the Sprycel Label stating that "SPRYCEL may cause fluid retention," and that "Grade 3 or 4 fluid retention was reported in 5% of patients, including 3% of patients with Grade 3 or 4 pleural effusion." Results obtained from the OPTIM-dasatinib study associated with the conventional crystalline dasatinib formulation, identifies Cm in as a driver for increased risk of pleural effusion. See Rousselt at 399; see also Wang at 90. And a separate evaluation of clinical trials for the conventional crystalline dasatinib formulation shows that a plasma trough concentration (C0) less than 2.5 ng/mL may avoid the incidence of pleural effusion. Miura at 645. Minimum plasma concentration (Cmin, or C24) is considered to be an alternative expression for plasma trough concentration (C0). Dosage results summarized below show that administration of a pharmaceutical composition disclosed herein provides for a greater percentage of C24 (or Cmin) less than or equal to about 2.5 ng/mL when compared to administration of an equivalent dosage amount of the conventional crystalline dasatinib formulation (e.g., Sprycel).

Accordingly, one aspect disclosed herein relates to a method for reducing pleural effusion in a patient suffering from CML by administering a pharmaceutical composition comprising dasatinib as an amorphous solid dispersion, wherein the administered amount of dasatinib is 20% to 30% lower in intra-subject variability of Cm in than a dose required for delivering a therapeutically effective amount of dasatinib in the fasted state using a conventional crystalline dasatinib formulation.

Alternatively, another aspect disclosed herein relates to a method for reducing pleural effusion in a patient suffering from CML by administering a pharmaceutical composition comprising dasatinib as an amorphous solid dispersion, wherein the administered amount of dasatinib is 20% to 30% less than a dose required for delivering a therapeutically effective amount of dasatinib in the fasted state using a conventional crystalline dasatinib formulation.

The Sprycel Label instructs the patient to dose SPRYCEL once daily with or without food.

An aspect of the present disclosure is to provide a pharmaceutical composition that is bioequivalent, including size limitations, to the corresponding RLD, such as Sprycel (dasatinib monohydrate).

Bioequivalence of the pharmaceutical compositions of the present disclosure is established by (a) 90% Confidence Interval for the ratio (generic drug vs reference listed drug) of mean AUC(0-t), e.g., AUC(0-24h), which is between 80% and 125%; (b) 90% Confidence Interval for the ratio (generic drug vs reference listed drug) of mean AUC(0-∞), which is between 80% and 125%; or (c) a 90% Confidence Interval for the ratio (generic drug vs reference listed drug) of mean Cmax, which is between 80% and 125%; or a combination of any features a-c above. In one aspect, the mean may be a least-squares geometric mean. In another aspect, the mean may be a log-transformed least-squares geometric mean.

Alternatively, bioequivalence of the pharmaceutical compositions of the present disclosure is established by: (a) a 90% Confidence Interval for the ratio (generic drug vs reference listed drug) of AUC(0-∞) is between 80% and 125%, and optionally without excluding any subjects with AUC(0-∞)<5% of the reference listed drug; (b) a 90% Confidence Interval the ratio (generic drug vs reference listed drug) for Cmax, which is between 80% and 125%; and without excluding any subjects with AUC (0-t), e.g., AUC (0-24h); and (c) a 90% Confidence Interval the ratio (generic drug vs reference listed drug) of Cmax, which is between 80% and 125%; or a combination of any features a-c above.

An aspect of the present disclosure is to provide a pharmaceutical composition with a dissolution profile that within about 5 minutes at least about 20% of the composition is dissolved. In other embodiments of the disclosure, at least about 30%, about 40%, about 50%, about 60%, about 70%, about 80%, about 90%, or about 100% of the active pharmaceutical ingredient, such as dasatinib, is dissolved within about 5 minutes.

In other embodiments of the disclosure, at least about 40%, about 50%, about 60%, about 70%, about 80%, about 90%, or about 100% of the active pharmaceutical ingredient, such as dasatinib, is dissolved within about 10 minutes.

In another embodiment of the disclosure, preferably at least about 70%, about 80%, about 90%, or about 100% of the active pharmaceutical ingredient, such as dasatinib, is dissolved within about 15 minutes.

In another embodiment of the disclosure, preferably at least about 70%, about 80%, about 90%, or about 100% of the active pharmaceutical ingredient, such as dasatinib, is dissolved within about 20 minutes.

In another embodiment of the disclosure, preferably at least about 70%, about 80%, about 90%, or about 100% of the active pharmaceutical ingredient, such as dasatinib, is dissolved within about 30 minutes.

Pharmaceutical Excipients

A pharmaceutical excipient is a substance formulated alongside the active ingredient of a medication, included for example for the purpose of long-term stabilization, bulking up solid formulations that contain potent active ingredients in small amounts (thus often referred to as "bulking agents", "fillers", or "diluents"), or to confer a therapeutic enhancement on the active ingredient in the final dosage form, such as facilitating drug absorption, reducing viscosity, or enhancing solubility. A pharmaceutical excipient can also be useful in the manufacturing process, to aid in the handling of the active substance concerned such as by facilitating powder flowability or non-stick properties, in addition to aiding in vitro stability such as prevention of denaturation or aggregation over the expected shelf life.

Binders

Many pharmaceutical excipients have dual functionality and fillers and binders are thus often treated as one group of pharmaceutical excipients, e.g., fillers/binders. Tablet fillers/binders are one of the most essential elements in the formulation of a tablet. Because they promote cohesiveness, the fillers/binders, are sometimes also referred to as adhesives, help the other ingredients in a tablet to mix together. A polymeric stabilizing and matrix-forming component used as a component in a solid dispersion also has properties and functionality as a binder. Tablet fillers/binders are used to turn powder to granules; this is achieved through the process of granulation. During granulation, powder substances are accumulated to form larger particles called granules.

Commonly used fillers/binders are sugars, natural and synthetic/semisynthetic binders, as summarized below:

| Sugars | Natural Binders | Synthetic/Semisynthetic Polymer |
|---|---|---|
| Sucrose | Acacia | Methyl Cellulose |
| Liquid glucose | Tragacanth | Ethyl Cellulose |
| Mannitol | Gelatin | Hydroxy Propyl Methyl Cellulose (HPMC) |
| Micro microcrystalline cellulose | Starch Paste | Hydroxy Propyl Cellulose |
| Lactose | Pregelatinized Starch | Sodium Carboxy Methyl Cellulose |
| Isomalt | Alginic Acid Cellulose | Polyvinyl Pyrrolidone (PVP) Polyethylene Glycol (PEG) Polyvinyl Alcohols Polymethacrylates |

A suitable amount of a filler/binder ranges from about 20% to about 90% by weight, about 30% to about 80% by weight, about 40% to about 70% by weight, and about 50% to about 60% by weight.

Disintegrants

The rate at which drugs dissolve in the biofluids of the body may be influenced by the tablet's disintegration. For most tablets, it may be necessary to overcome the cohesive forces that bind together the particles within the tablet that were introduced as a result of the tablet pressing process. This may be difficult in some cases through the introduction of materials that are added before the tableting process with the aim of binding the particles together.

A disintegrant is an excipient that is incorporated into the formulation of tablets or capsules to promote their disintegration when they come into contact with liquid or fluid matter. Several types of disintegrant may be distinguished according to their mode of action: (a) those that enhance the action of capillary forces that promote the absorption of water (by wicking) (b) those that swell on contact with water and (c) those that release gases leading directly to disintegration of the tablet, so-called effervescent tablets. The general purpose of incorporating one or more disintegrants in the product formulation is to increase the surface area of the product and soften the binding matter that holds together the solid particles that make up the product. The net effect is that a tablet when exposed to aqueous media disintegrates first into granules, and then into fine particles.

An effervescent tablet is a tablet that quickly dissolves in drinking water at ambient temperature, usually taking about 20-30 seconds to dissolve depending on the temperature.

The growing demand for faster and more rapid disintegrating formulations has stimulated the development of superdisintegrants, which may have a greater effectiveness even at a low concentration, and which may be effective as an intragranular component. Unfortunately most superdisintegrants are hygroscopic and readily absorb moisture, which generally rules them out for drugs that are moisture-sensitive.

A suitable disintegrant, such as croscarcellose sodium, crospividone, and sodium starch glycolate, or a combination thereof may be used. A suitable amount of a disintegrant ranges from about 4% to about 16% by weight, about 6% to about 15% by weight, about 8% to about 14% by weight, about 10% to about 13% by weight, and about 11% to about 12% by weight.

In one aspect, the disintegrating agent comprises crospovidone.

In yet another aspect the disintegrating agent comprises crospovidone in an amount that ranges of from about 4.0% by weight and about 9.0% by weight, and all values in between.

Gas Generating Agents

A suitable gas generating agent is selected from a group consisting of a sodium carbonate, a potassium carbonate, a sodium bicarbonate, a potassium bicarbonate, a sodium sulfite, a potassium sulfite, an ammonium cation, and a combination thereof.

Alternatively, a hard sugar mixture comprising pressurized carbon dioxide may also be used. A suitable hard sugar mixture comprises, for example, sugar, sucrose, lactose, and corn syrup, or a combination thereof. Such a hard sugar mixture is prepared by, for example, mixing sugar and corn syrup in water to obtain a mixed mass; heating the mixed mass to about 150° C. to drive off water to obtain a hot sugar mass. The hot sugar mass is then mixed with carbon dioxide gas at an elevated pressure, such as about 600 pounds per square inch (psi) to obtain a hot sugar-$CO_2$ mass. The hot sugar-$CO_2$ mass is thereafter allowed to cool and the pressure is released to obtain the hard sugar mixture. The obtained hard sugar mixture maybe used herein as a gas generating agent.

A suitable amount of a gas generating agent ranges from about 8% to about 22% by weight, about 10% to about 18% by weight, about 12% to about 16% by weight, and about 14% by weight.

Acidic pH-Modifier

An acidic pH-modifier may be added as a pharmaceutical excipient to the pharmaceutical composition of the present disclosure. A suitable acidic pH-modifier, such as a carboxylic acid may be used. A suitable carboxylic acid is selected from a group consisting of citric acid, sorbic acid, adipic acid, succinic acid, fumaric acid, tartaric acid, or a combination thereof.

A suitable amount of an acidic pH-modifier ranges from about 2% to about 7% by weight, about 3% to about 6% by weight, and about 4% by weight, and about 5% by weight.

Alternatively, the amounts of acidic pH-modifiers may be measured relative to the amounts of gas generating agent. For instance, it may be desirable to have a mole ratio of the gas generating agent to the acidic pH-modifier of about 4:1 to about 1:4, such as about 2:1 to about 1:2.

Solubilizers

A solubilizers may be used to increase the solubility of a substance, such as an active pharmaceutical ingredient. A solubilizer may be selected from the group consisting of a d-α-tocopherol acid polyethylene glycol 1000 succinate, sodium dodecyl sulphate, a PEG-40 hydrogenated castor oil, a PEG-35 castor oil, a PEG-40 stearate, a hard fat, a polyoxylglyceride, a PEG-8 caprylic/capric glyceride, a poloxamer, and a combination thereof.

Glidants

A glidants may be used to promote powder flow by reducing interparticle friction and cohesion. A glidants may be used in combination with a lubricant as they have small ability to reduce die wall friction. A glidant may be selected from the group consisting of anhydrous colloidal silica, calcium phosphate tribasic, powdered cellulose, hydrophobic colloidal silica, magnesium oxide, magnesium silicate, magnesium trisilicate, silicon dioxide, talc, and a combination thereof. A suitable amount of a glidant ranges from about to about 5% by weight, about 1% to about 4% by weight and about 2% to about 3% by weight.

Lubricants

A lubricant may prevent the clumping of an active ingredient and prevent the sticking of materials to machines in any of the manufacturing steps of the whole manufacturing process. A lubricant may be selected from the group consisting of calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, medium-chain triglyceride, mineral oil, myristic acid, palmitic acid, poloxamer, polyethylene glycol, sodium benzoate, sodium chloride, sodium lauryl sulfate, sodium stearyl fumarate, stearic acid, talc, zinc stearate, and a combination thereof. A suitable amount of lubricant ranges from about 0.5% to about 5% by weight, about 1% to about 4% by weight and about 2% to about 3% by weight in each of manufacturing step where it is being used.

Tableting

Tableting is a method whereby a powder or granule mixture is prepared, and thereafter filled in a dye mold, and then the mixture is pressed or compressed into tablets and tablet is thereafter ejected. Any conventional tableting machine may be used. Conventional tableting machines may generate a compression force of about 4 kN upto about 30 kN, such as about 10 kN upto about 20 kN.

Coatings

A coating may protect a tablet ingredient from deterioration by moisture in the air and make large or unpleasant-tasting tablets easier to swallow. A coating material may be selected from the group consisting of carnauba wax, cellulose acetate, cellulose acetate phthalate (CAP), ceresin, cetyl alcohol, chitosan, ethylcellulose, fructose, gelatin, glycerin, glyceryl behenate, glyceryl palmitostearate, hydroxyethyl cellulose, hydroxyethylmethyl cellulose, hydroxypropyl cellulose, hypromellose, hypromellose phthalate, isomalt, latex particles, liquid glucose, macrogol 400, maltitol, maltodextrin, methylcellulose, microcrystalline wax, paraffin, poloxamer, polydextrose, polyethylene glycol, polyethylene oxide, poly-DL-(lactic acid), polyvinyl acetate phthalate, polyvinyl alcohol, povidone, shellac, shellac with stearic acid, surface color agents, titanium oxide, tributyl citrate, triethyl citrate, vanillin, white wax, xylitol, yellow wax, zein, and a combination thereof. Certain coating agents marked under the tradename OPADRY® may be used. One grade of OPADRY® comprises hypromellose, macrogol 400, and Polysorbate 80. Any suitable coating method, like spraying may be used. A color may be added to improve the appearance of a tablet. Color consistency may be important as it allows easy identification of a medication. Some coatings are therefore colored using OPADRY® Blue or OPADRY® White, wherein titanium dioxide is the white color agent.

A suitable amount of coating ranges from about 0.5% to about 3% by weight, about 1% to about 2% by weight and about 1.8% to about 1.9% by weight.

In one embodiment, there is provided an aqueous based coating process of a compressed tablet comprising: (a) particles comprising (i) dasatinib in an amount of about 10% by weight to about 70% by weight of the particles; and (ii) at least one polymeric stabilizing and matrix-forming component; (b) at least one disintegrant agent in an amount of about 4% by weight to about 16% by weight; (c) at least one gas generating agent in an amount of about 8% by weight to about 16% by weight; (d) at least one acidic pH-modifier in an amount of about 2% by weight to about 6% by weight; and (e) optionally at least one pharmaceutically acceptable solubilizer selected from the group consisting of a d-α-tocopherol acid poly-ethylene glycol 1000 succinate, a PEG-40 hydrogenated castor oil, a PEG-35 castor oil, a PEG-40 stearate, a hard fat, a polyoxylglyceride, a PEG-8 caprylic/capric glyceride, and a poloxamer or mixtures thereof; wherein optionally the at least one pharmaceutically acceptable solubilizer, when present, is a physical mixture with the particles.

Such an aqueous based coating process produces coated tablets that are stable during the process and upon following storage and thus compliant with the stability recommendations for ANDAs submitted under section 505(j) of the Federal Food, Drug and Cosmetic Act, and the drug master files (DMFs) that support ANDAs (see GFI, Stability Testing).

In another aspect, a composition disclosed herein may be used in therapy.

In another embodiment, a composition disclosed herein may be used in the treatment of a proliferative disorder. Typically, said proliferative disorder is selected from tumors and cancers, including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

More typically said proliferative disorder is selected from newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; adults with Philadelphia chromosome-positive acute lymphoblastic leukemia (Ph+ ALL) with resistance or intolerance to prior therapy.

In another embodiment of this aspect, there is provided a composition to be administered without regard to whether the patient is in a fasted state or a fed state.

As generally interpreted, "food effect" broadly refers to all aspects of interactions of food on drug dissolution, absorption, distribution, metabolism and elimination. The implications of food effect include changes in bioavailability, rate of on-set, duration of therapeutic effect and incidence and seriousness of side effects. The magnitude of a food effect is generally greatest when the drug product is administered shortly after a meal is ingested. An example of a drug product is with a food effect is Sprycel, which as described above can produce a decrease of AUC and/or Cmax respectively, when orally taken 30 minutes after a high-fat meal as compared to levels obtained under fasting conditions.

In practice, a food effect is generally assessed by measuring standard pharmacokinetic parameters observed upon administration of a drug product to a subject in a fasted state, versus the same measurements observed upon administration to the same subject in a fed state. Relevant pharmacokinetic parameters can include AUC, Cmax, and/or Tmax. AUC can be assessed for a specified time interval (such as AUC(0-12 h) or AUC(0-24 h), for example), or as AUC(0-last) or AUC(0-∞). Typically, data for a number of test subjects is pooled for analysis. For further information about food effect studies, refer to GFI, Food Effect and GFI, Assessing Food Effects.

As used in relation to the methods of the present disclosure the phrase "food effect" refers to a relative difference in one or more of AUC, Cmax, and/or Tmax for an active substance, when said substance or a formulation thereof (such as a solid dispersion or pharmaceutical composition) is administered orally to a human subject, concomitantly with food or in a fed state, as compared to the measured value for the same parameter when the same formulation is administered to the same subject in a fasted state.

The food effect F is calculated as $$F=(Y\text{fed}-Y\text{fasted})Y\text{fasted}$$

wherein Yfed and Yfasted are the measured values of AUC, Cmax or Tmax in the fed and fasted state, respectively.

The phrase "positive food effect" refers to a food effect where the AUC and/or Cmax is higher when the drug product is administered orally in a fed state than when it is administered in a fasted state. The phrase "negative food effect" refers to a food effect where the AUC and/or Cmax is lower when the drug product is administered orally in the fed state than when it is administered in the fasted state.

In assessing food effect, data obtained from fasted and fed studies is processed using conventional pharmacokinetic statistical analyses and methods. Fasted and fed studies may be single-dose studies or steady-state studies, as appropriate. Using pooled data from a suitable number of subjects, an absence of food effect is indicated when the 90% CI for the ratio of population geometric means between fed and fasted administrations, based on log-transformed data, is contained in the equivalence limits of 80% to 125% for AUC(0-∞) (or AUC(0-t), e.g., AUC(0-24h), when appropriate) and Cmax. On the other hand, an absence of food effect is not established if the 90 percent CI for the ratio of population geometric means between fed and fasted administrations, based on log-transformed data, is not contained in the equivalence limits of 80% to 125% for either AUC(0-∞) (or AUC(0-t), e.g., AUC(0-24h), when appropriate) or Cmax.

In the methods of the present disclosure, "without a food effect" means that the relative difference is not substantially large, e.g., less than 20%, or less than 15%, or less than 10%, for AUC (which can be, for example, AUC(0-24 h), AUC (0-last) or AUC(0-∞)) and/or Cmax, for dasatinib when the ASD or pharmaceutical composition of the present disclosure is administered orally, concomitantly with food or in a fed state, as compared to the measured value for the same parameter when the same ASD or pharmaceutical composition is administered in a fasted state. (As used herein, for a relative difference stated as a percentage, each stated range is with respect to the absolute value of that relative difference; i.e., "less than 20%" means that the relative difference F falls in the range $-20\%<F<+20\%$.)

In the methods of the present disclosure, "without regard to consumption of food" means that no consideration has to be made whether the ASD or pharmaceutical composition of the present disclosure is being administered to the subject or patient concomitantly with food, or whether the patient or subject is in a fed state or fasted state. The administration will be expected to provide a therapeutically relevant exposure and will not be expected to cause an unsafe overexposure, regardless of whether the patient or subject is in a fed state or fasted state.

As used herein, the phrase "conventional dasatinib composition" refers to a commercially available composition comprising dasatinib monohydrate, generally in crystalline form. The conventional dasatinib composition may be in a tablet dosage form. One suitable conventional dasatinib composition is Sprycel Tablet (marketed in the United States under New Drug Applications 21986 and 22072). Sprycel is understood to contain crystalline dasatinib monohydrate in a tablet formulation.

Administration of a pharmaceutical composition, containing an ASD, of the present disclosure can be characterized by the pharmacokinetic profile or by calculated pharmacokinetic parameters (such as Cmax and/or AUC(0-t), which can be, for example, AUC(0-24h), AUC(0-last) or AUC(0-∞)) resulting from the administration of a pharmaceutical composition, containing an ASD, at certain dosages to a subject in a fasted state or a fed state.

Administration of a pharmaceutical composition, containing an ASD, of the present disclosure can also be characterized by how the pharmacokinetic profile resulting from administration of a pharmaceutical composition, containing an ASD, to a subject in a fed state compares to the pharmacokinetic profile resulting from administration of a pharmaceutical composition, containing an ASD, to a subject in a fasted state. As an example, for some embodiments, administration of a pharmaceutical composition, containing an ASD, of the present disclosure to a subject in a fed state and in a fasted state may result in a relative difference in the plasma exposure of dasatinib between the fed state and the fasted state of less than 50%, less than 40%, or less than 35%, or less than 30%, or less than 25%, or less than 20%, or less than 15%, or less than 10%, or less than 5%. Exposure may be expressed as AUC(0-12 h), AUC(0-24 h), AUC(0-last), or AUC(0-∞), for example. Exposure can be demonstrated for an individual subject, or alternatively for a suitable number of subjects (n>1). When comparing a number of subjects for which data is pooled, the exposure may be expressed as a population geometric mean, in accordance with conventional pharmacokinetic statistical analyses and methods.

Methods of Administering at Reduced Dosage

In addition, administration of a pharmaceutical composition, comprising an ASD disclosed herein may be characterized by how the pharmacokinetic profile resulting from administration of a pharmaceutical composition, comprising an ASD, compares to the pharmacokinetic profile resulting from administration of a conventional dasatinib composition.

For instance, in some embodiments, administration of a pharmaceutical composition, containing an ASD, of the present disclosure may result in a pharmacokinetic profile that is comparable to the pharmacokinetic profile obtained by orally administering a conventional dasatinib formulation, but administered at a fraction of the dosage (e.g., from about 0.70 to about 0.75). For this comparison, administration must be done in a fasted state, since Sprycel should only be administered in a fasted state.

For embodiments of the disclosure that can be administered at a fraction (e.g., from about 0.70 to about 0.75) of the dosage as compared to the dosage required when administering a conventional dasatinib composition, it can be reasoned that the inventive formulation is inherently safer than the corresponding conventional dasatinib composition. By decreasing the required dosage while still providing an efficacious exposure to the patient, the risks of overexposure are reduced.

By way of example only, a pharmaceutical composition of the present disclosure containing approximately 100 mg dasatinib free base may provide a pharmacokinetic profile that is comparable to the pharmacokinetic profile obtained by orally administering a crystalline dasatinib formulation labeled to contain 140 mg of dasatinib (such as 140 mg Sprycel Tablet). In this example, the dose of dasatinib in the inventive pharmaceutical composition is 75% less than the dosage of the crystalline dasatinib formulation.

In some embodiments, the dose of dasatinib in a pharmaceutical composition, containing an ASD, of the present disclosure is 80% less, or 75% less, or 70% less, or 65% less, or 60% less, or 55% less, or 50% less, as compared to the labeled dosage of the crystalline dasatinib monohydrate formulation. In one aspect, the dose of dasatinib in a pharmaceutical composition disclosed herein has a reduced dosage amount (e.g., from about 0.70 to about 0.75) compared to the labeled dosage of the crystalline dasatinib formulation.

In one embodiment, there is provided a dasatinib containing composition with a drug-drug interaction with antacid preparations, including PPIs, that is less (decreased) compared to Sprycel (dasatinib monohydrate).

In another aspect, the present disclosure relates to a method of treating a patient who has a proliferative disorder and is suffering from condition caused by the overproduction of stomach acid or exacerbated by stomach acid, the method comprising co-administering to the patient (a) a therapeutically effective amount of a pharmaceutical composition of the present disclosure, and (b) a therapeutically effective amount of a gastric acid-reducing agent. The gastric acid reducing agent may be administered shortly before, shortly after or concurrently with the pharmaceutical composition of the present disclosure.

In yet another aspect, the present disclosure relates to a method of delivering a therapeutically effective amount of dasatinib to a patient without regard to whether the patient is concurrently administered a gastric acid-reducing agent, comprising administering a therapeutically effective amount of a pharmaceutical composition of the present disclosure to the patient.

"Gastric acid-reducing agent" refers herein to any agent that acts to significantly reduce the amount of acid in a subject's stomach. Acid reduction can be due to suppression or blocking of acid secretion, or by neutralization of stomach acid. Examples of gastric acid-reducing agents include, but are not limited to, proton pump inhibitors, histamine-2 receptor antagonists (or H2 antagonists), and antacids.

Proton pump inhibitors reduce stomach acid production by blocking the hydrogen/potassium adenosine triphosphatase enzyme (i.e., the gastric proton pump) of the parietal cells, which are the epithelial cells that secrete stomach acid. Examples of proton pump inhibitors include, but are not limited to, rabeprazole, esomeprazole, lansoprazole, omeprazole, pantoprazole, and dexlansoprazole.

H2 antagonists block histamine from binding to the H2 receptors of parietal cells, thereby suppressing both the normal secretion and meal-stimulated secretion of acid by parietal cells. Examples of H2 antagonists include, but are not limited to, famotidine, cimetidine, nizatidine, and ranitidine.

Antacids contain alkaline ions that chemically neutralize stomach gastric acid. Examples of antacids include, but are not limited to, aluminum hydroxide, magnesium hydroxide, sodium citrate, sodium carbonate, sodium bicarbonate, calcium carbonate, and magnesium trisilicate.

The gastric acid-reducing agent may be administered in accordance with the dosing information that is known in the art for the agent, or according to a physician's instructions. A "therapeutically effective amount" of the gastric acid-reducing agent may be the amount set forth in the dosing information that is known in the art for the gastric acid-reducing agent, or according to a physician's instructions. A "standard dosage" is a dosage in accordance with a product's labeled instructions. In particular, a standard dosage is appropriate for gastric acid-reducing agents that are available over-the-counter (i.e., without a physician's prescription), such as most antacids, certain H2 antagonists, and certain proton pump inhibitors.

As used herein, a condition caused by the overproduction of stomach acid or exacerbated by stomach acid may be any condition that can be treated by reducing the amount of acid or the acidity in the subject's stomach. Examples of such a condition include, but are not limited to, dyspepsia (i.e., indigestion), gastroesophageal reflux disease, duodenal or stomach ulcers, erosive esophagitis, stress gastritis, Barrett's esophagus, and gastrinomas.

As used herein, "co-administration" (or "co-administered") refers to the administration of two or more therapeutic agents within a relevant period of time (such as one day, or 12 hours, or 8 hours, or 6 hours, for example), such that consideration must be given to whether the administration of one of the therapeutic agents may affect the absorption or efficacy of the other. Such administration may be for the treatment of two or more conditions simultaneously, such as, by way of example only, a patient requiring treatment for a proliferative disorder as described herein with dasatinib as a therapeutic agent, while also being treated for another condition, such as acid reflux or ulcers, with a second therapeutic agent such as a gastric acid-reducing agent (e.g., a proton pump inhibitor). Since both therapeutic agents are dosed at least once daily, the two therapeutic agents are "co-administered," and consideration must be given to whether the administration of one of the therapeutic agents may affect the absorption or efficacy of the other.

In the context of the present disclosure, the phrase "can be co-administered" means that the two (or more) therapeutic agents of interest can be co-administered without a detrimental reduction in the exposure of dasatinib. "Without a detrimental reduction" indicates that the realized exposure would be comparable to the exposure realized when the gastric acid-reducing agent is not co-administered. Any difference in the realized exposure would be insubstantial and/or therapeutically inconsequential. In contrast, when a detrimental reduction in exposure would be realized, then co-administration should be avoided. A "detrimental reduction" means a substantial and material reduction in the realized exposure. By way of example, if the realized exposure would be less than or equal to a level recognized as a sub-therapeutic exposure, then the co-administration would result in a detrimental reduction in exposure.

As used herein, the phrase "gastric acid-insensitive composition" indicates a pharmaceutical composition of the present disclosure that can be administered without regard to the patient or subject's gastric pH. A gastric acid-insensitive composition provides a therapeutically relevant exposure to the patient or subject across a range of gastric pH values. Accordingly, a gastric acid-insensitive composition can be administered whether or not the patient or subject has ingested a gastric acid-reducing agent, or whether or not the patient has a condition that causes elevated gastric pH (as further discussed below).

Embodiments of the disclosure relate to administering a gastric acid-reducing agent shortly before, concurrently with, or shortly after the dasatinib ASDs or pharmaceutical compositions of the disclosure. The term "shortly before" as used herein may mean that a gastric acid-reducing agent was administered to the subject 10 hours or less, or 8 hours or less, or 6 hours or less, or 5 hours or less, or 4 hours or less, or 3 hours or less, or 2 hours or less, or 1 hour or less, or 45 minutes or less, or 30 minutes or less, or 15 minutes or less, prior to the administration of the pharmaceutical composition of the disclosure. The term "concurrently" or "concomitantly" as used herein may mean that a gastric acid-reducing agent was administered to the subject within 30 minutes or less, or within 20 minutes or less, or within 15 minutes or less, or within 10 minutes or less, or within 5 minutes or less, or within 4 minutes or less, or within 3 minutes or less, or within 2 minutes or less, or within 1 minute or less, or simultaneously, of the administration of the pharmaceutical composition. The term "shortly after" as used herein means that a gastric acid-reducing agent was administered to the subject 6 hours or less, or 5 hours or less, or 4 hours or less, or 3 hours or less, or 2 hours or less, or 1 hour or less, or 45 minutes or less, or 30 minutes or less, or 15 minutes or less, after the administration of the pharmaceutical composition.

In some embodiments, administration of an ASD or pharmaceutical composition of the present disclosure to a subject who was concurrently, shortly before, or shortly after administered a gastric acid-reducing agent exhibits a pharmacokinetic profile of dasatinib that is similar to the pharmacokinetic profile resulting from administration of the ASD or pharmaceutical composition to a subject who was not concurrently, shortly before, or shortly after administered a gastric acid-reducing agent. In certain embodiments, single administration of the ASD or pharmaceutical composition to a subject who was concurrently, shortly before, or shortly after administered a gastric acid-reducing agent results in an AUC of dasatinib that is within 50%, or within 40%, or within 30%, of the AUC of dasatinib that results from administration of the ASD or pharmaceutical composition without being administered the gastric acid-reducing agent concurrently, shortly before, or shortly after. In certain embodiments, the AUC is AUC(0-24 h). In other embodiments, the AUC is AUC(0-∞).

Further, one aspect of the present disclosure relates to the use of a pharmaceutical composition, comprising an ASD, of the present disclosure to deliver dasatinib to a subject without regard to the subject's gastric pH. Some embodiments relate to a method of delivering dasatinib to a human subject without regard to the subject's gastric pH, the method comprising administering a pharmaceutical composition, comprising an ASD, of the present disclosure to the human subject. Some embodiments relate to a use of a dasatinib ASD or pharmaceutical composition of the present disclosure for delivering dasatinib to a subject without regard to the subject's gastric pH, the use comprising administering a pharmaceutical composition, containing an ASD, Some embodiments relate to a pharmaceutical composition, containing an ASD, of the present disclosure for use in delivering dasatinib to a subject without regard to the subject's gastric pH, the use comprising administering a pharmaceutical composition, containing an ASD, to the subject.

In another aspect, there is provided a method of treating proliferative disorder in a patient in need thereof, comprising administering a therapeutically effective amount of a composition disclosed herein. Said proliferative disorder is typically selected from tumors and cancers including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

Said proliferative disorder is more typically selected from newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; adults with Philadelphia chromosome-positive acute lymphoblastic leukemia (Ph+ ALL) with resistance or intolerance to prior therapy.

The desired dose may be conveniently presented in a single dose or as a divided dose administered at appropriate intervals, for example as two, three, four or more doses per day. Dependent on the need of the treatment and/or prevention, the desired dose may also be, for example, once every two days, once every three days, or even once a week.

The composition may be conveniently administered in unit dosage form; for example containing from about 5 to about 200 mg of dasatinib, including all values in between, such as, for example, 10, 15, 20, 25, 30, 35, 36, 40, 45, 50, 55, 57, 60, 65, 70, 80, 85, 90, 95, 100, 105, 110, 115, 120, 125, 130, 135, 140, 145, 150, 155, 160, 165, 170, 175, 180, 185, 190, 195, or 200 mg of active ingredient per unit dosage form.

Methods of Treatment with Reduced Variability

Administration of a pharmaceutical composition disclosed herein does not exhibit anomalously low systemic exposure profiles, where administration provides a coefficient of variation with respect to at least one pharmacokinetic parameter that is 40% lower, 35% lower 30% lower, 25% lower, 20% lower, 15% lower, 10% lower, or 5% lower than the coefficient of variation observed for the standard commercial, composition of dasatinib (e.g., Sprycel) when administered under similar conditions. The pharmacokinetic parameter can be any of Cmax, AUC(last) (AUC up to the last measurable concentration and sometimes referred to as AUC(0-t), e.g., AUC(0-24h), and AUC(0-∞)). In some embodiments, the improved variability composition provides an improvement with respect to Cmax and at least one of AUC(last) and AUC(0-∞). In other embodiments, the improved variability composition provides an improvement with respect to each of Cmax, AUC(last), and AUC(0-∞)

Accordingly, an aspect disclosed herein relates to a method of treating a disorder in a patient in need thereof, which comprises administering a therapeutically effective amount of a pharmaceutical formulation comprising an amorphous solid dispersion of dasatinib (comprising about 5 to about 200 mg of dasatinib, including all values in between), wherein said proliferative disorder is newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and adults with Philadelphia chromosome-positive acute lymphoblastic leukemia (Ph+ ALL) with resistance or intolerance to prior therapy, where administering the pharmaceutical formulation provides a coefficient of variation with respect to at least one pharmacokinetic parameter that ranges from about 5% lower to about 40% lower (and all values in between, for example, about 10% lower, about 15% lower, about 20% lower, about 25% lower, about 30% lower, and about 35% lower), than the coefficient of variation observed for the standard commercial, composition of dasatinib (e.g., Sprycel) when administered under similar conditions.

Methods of Improving Survival

Administration of a pharmaceutical composition disclosed herein improves survival in the patient over 5-years. For instance, concurrent administration of a therapeutically effective amount of an immediate release tablet disclosed herein and an acid reduction agent (viz., ARA, e.g., omeprazole) showed no drug-drug interaction between dasatinib and the ARA. Also, as explained herein, administration of a therapeutically effective amount of an immediate release tablet disclosed herein reduces anomalously low dasatinib systemic exposure.

Accordingly, an aspect disclosed herein relates to a method of treating a disorder in a patient in need thereof, which comprises administering a therapeutically effective amount of a pharmaceutical formulation comprising an amorphous solid dispersion of dasatinib (comprising about 5 to about 200 mg of dasatinib, including all values in between), wherein said proliferative disorder is newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and adults with Philadelphia chromosome-positive acute lymphoblastic leukemia (Ph+ ALL) with resistance or intolerance to prior therapy, wherein the method provides for an increased probability in patient survival over compared to a Sprycel-treated patient, wherein the patient optionally undergoes concurrent ARA administration and where the probability of survival ranges from about 1% to about 10% and all values in between, including, for example, about 2%, about 3%, about 4%, about 5%, about 6%, about 7%, about 8%, and about 9%, and wherein the amount of dasatinib administered ranges of from about 5 to about 200 mg of dasatinib, including all values in between.

Another aspect relates to a a method of treating a disorder in a patient in need thereof, which comprises administering a therapeutically effective amount of a pharmaceutical formulation comprising an amorphous solid dispersion of dasatinib (comprising about 5 to about 200 mg of dasatinib, including all values in between), wherein said proliferative disorder is newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and adults with Philadelphia chromosome-positive acute lymphoblastic leukemia (Ph+ ALL) with resistance or intolerance to prior therapy, wherein the method provides for a reduction in the probability of mortality in the patient over 5-years; compared to a Sprycel-treated patient, wherein the patient optionally undergoes concurrent ARA administration; and wherein the probability of mortality ranges from about 5% to about 50% and all values in between, including, for example, about 10%, about 15%, about 20%, about 25%, about 30%, about 35%, about 40%, and about 45%.

Methods of Reducing Pleural Effusion

An aspect disclosed herein relates to a method for reducing pleural effusion in a patient suffering from a proliferative disorder (e.g., newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; adults with Philadelphia chromosome-positive acute lymphoblastic leukemia (Ph+ ALL) with resistance or intolerance to prior therapy) by administering a pharmaceutical composition comprising dasatinib as an amorphous solid dispersion, wherein the administered amount of dasatinib is 20% to 30% lower in intra-subject variability of Cmin than a dose required for delivering a therapeutically effective amount of dasatinib in the fasted state using a conventional crystalline dasatinib formulation.

Another aspect disclosed herein relates to a method for reducing pleural effusion in a patient suffering from a proliferative disorder (e.g., newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; adults with Philadelphia chromosome-positive acute lymphoblastic leukemia (Ph+ ALL) with resistance or intolerance to prior therapy) by administering a pharmaceutical composition comprising dasatinib as an amorphous solid dispersion, wherein the administered amount of dasatinib is 20% to 30% less than a dose required for delivering a therapeutically effective amount of dasatinib in the fasted state using a conventional crystalline dasatinib formulation.

Clinical Results

Figure 5:
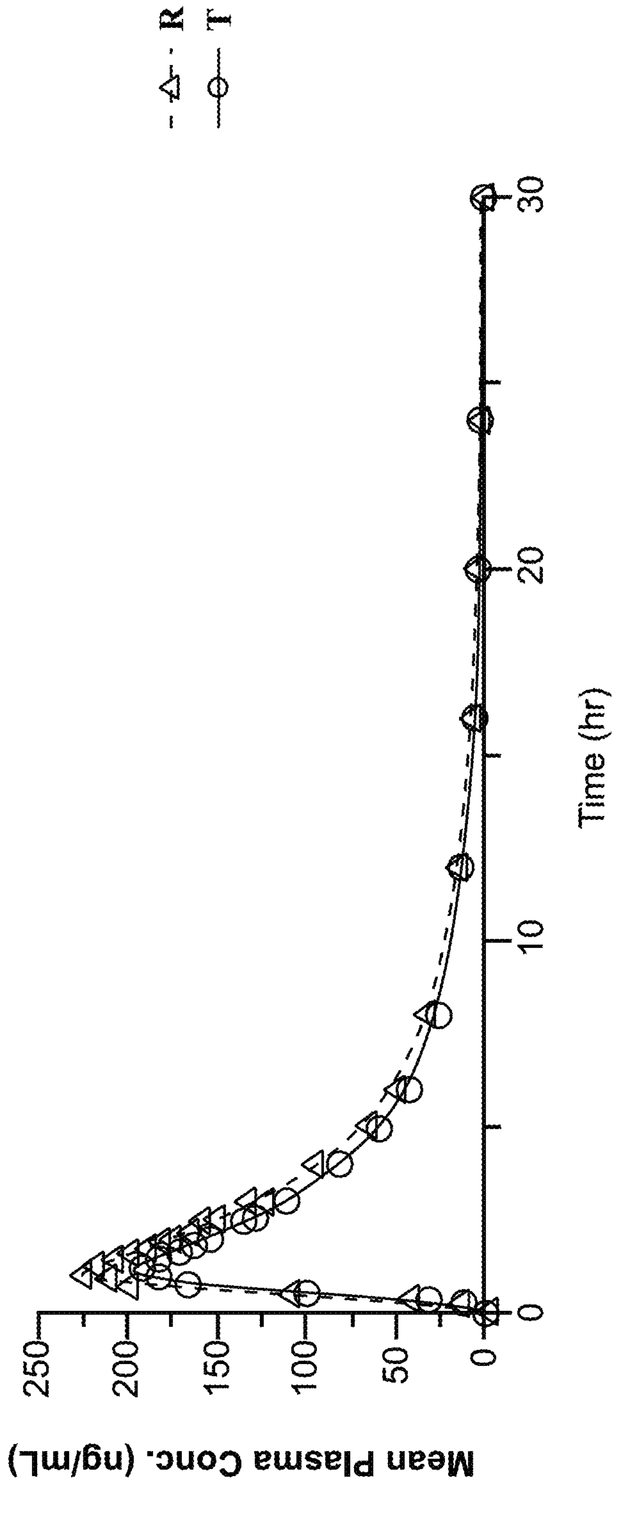
FIG. 5 provides Mean Plasma Concentration-Time Profile for Dasatinib 100 mg Test Formulation (denoted T) and Sprycel 140 mg (denoted R).
Figure 6:
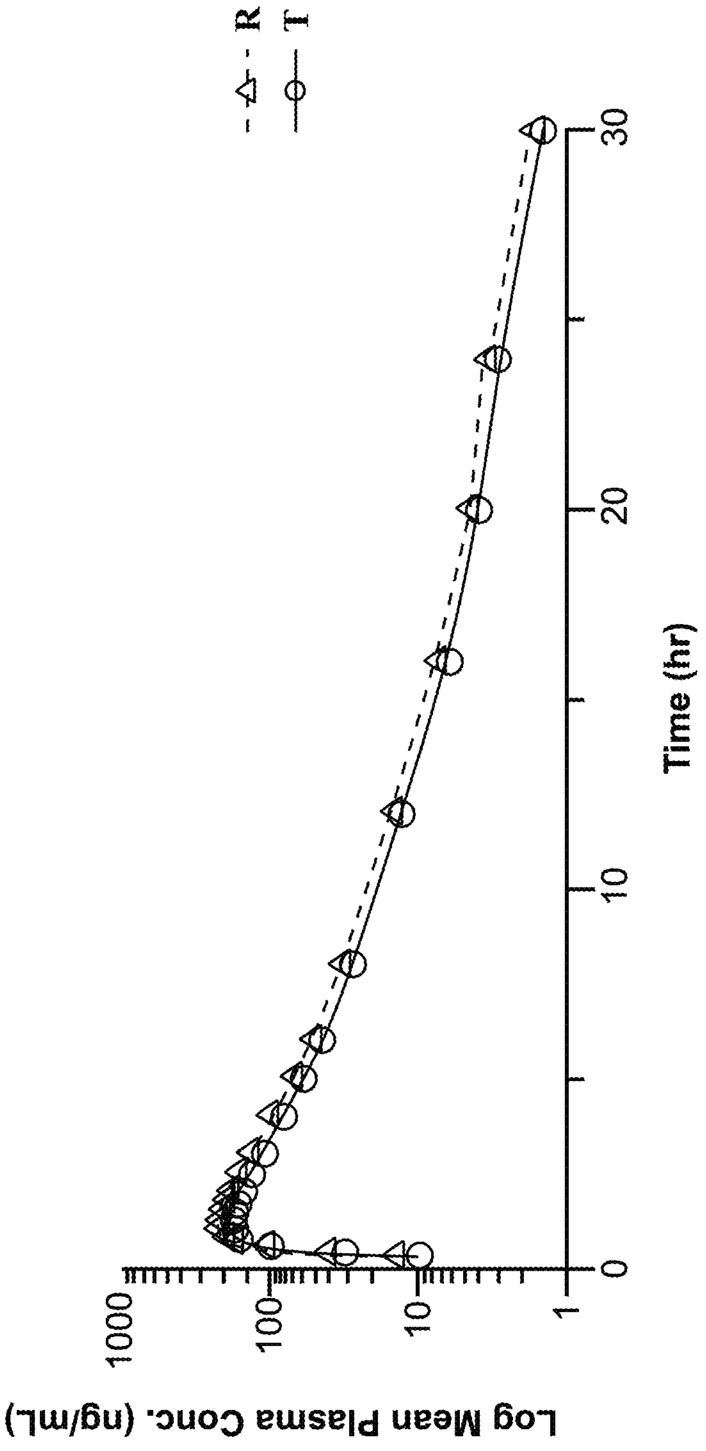
FIG. 6 provides Semi-log Mean Plasma Concentration-Time Profile for Dasatinib 100 mg Test Formulation (denoted T) and Sprycel 140 mg (denoted R).

A clinical study including 107 subjects showed that a single 100 mg dose of a formulation disclosed herein (Example 6) is bioequivalent to a single 140 mg dose of Sprycel, the RLD under fasting conditions. Hereafter, the tablet formulation of Example 6 is referred to as the "Dasatinib 100 mg Tablets Test Formulation" (or "Test Formulation" or "Test"), while Sprycel (dasatinib monohydrate) 140 mg is referred to as the "Reference Formulation" (or "Reference" or "RLD"). The study was a single-dose full replicate crossover comparative bioavailability study of Dasatinib 100 mg Tablets Test Formulation and Sprycel 140 mg tablets in healthy subjects in the fasting state. The results indicate that a single dose of Dasatinib 100 mg Tablets Test Formulation is bioequivalent to 140 mg Sprycel. The 90% confidence interval of the relative mean Cmax, AUC(0-t), e.g., AUC(0-24h), and AUC(0-∞) of Dasatinib 100 mg Tablets Test Formulation to Sprycel 140 mg (RLD) for log-transformed data were within 80% to 125% to establish bioequivalence (Table 1, FIG. 5 and FIG. 6). This indicates that administration of 100 mg Test Formulation will be associated with the same safety and efficacy as Sprycel 140 mg. This study is therefore the pivotal bridge to Sprycel's NDA 21,986.

TABLE 1

Relative Fasted Bioavailability of Dasatinib 100 mg Test Formulation (denoted Test or T) and Sprycel 140 mg (denoted Sprycel or R)

| | Assessment Dasatinib 100 mg Test Formulation 100 mg vs. SPRYCEL 140 mg (RLD) Average Bioequivalence (ABE) All subjects (n = 107) | | | |
|---|---|---|---|---|
| | Test 100 mg | Sprycel 140 mg | Ratio T/R (%) | 90% CI |
| $C_{max}$ (ng/ml) | 240.60 ± 85.989 | 265.65 ± 125.64 | 100.84 | 90.78-112.00 |
| AUC(0-24) (ng · hr/mL) | 864.009 ± 213.213 | 989.155 ± 390.609 | 94.22 | 87.54-101.42 |
| AUC(0-∞) (ng · hr /mL) | 877.311 ± 215.590 | 1011.402 ± 387.627 | 92.18 | 86.20-98.57 |

Variability

In the study the Cmax of Dasatinib 100 mg Tablets Test Formulation and Sprycel 140 mg tablets following oral administration in healthy subjects in the fasting state was observed at a 1.25 hr (median Tmax), although, Sprycel was associated with significantly greater variability (range: 0.50-24.00) when compared with Test Formulation (range: 0.33-3.00).

Figure 16:
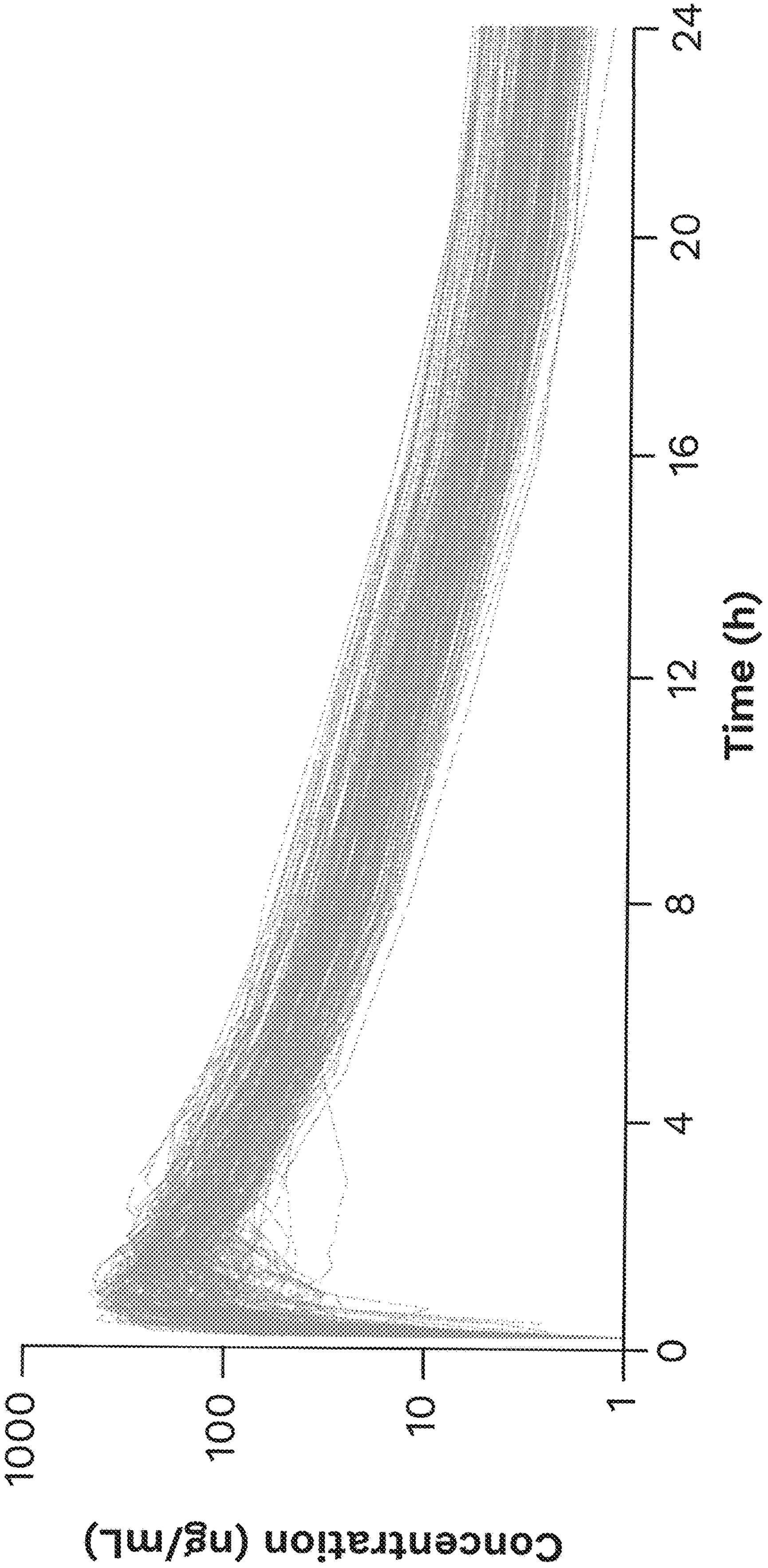
FIG. 16 provides individual plasma concentration time of dasatinib following a single dose oral administration of Test Formulation (100 mg dasatinib) under fasting conditions.
Figure 17:
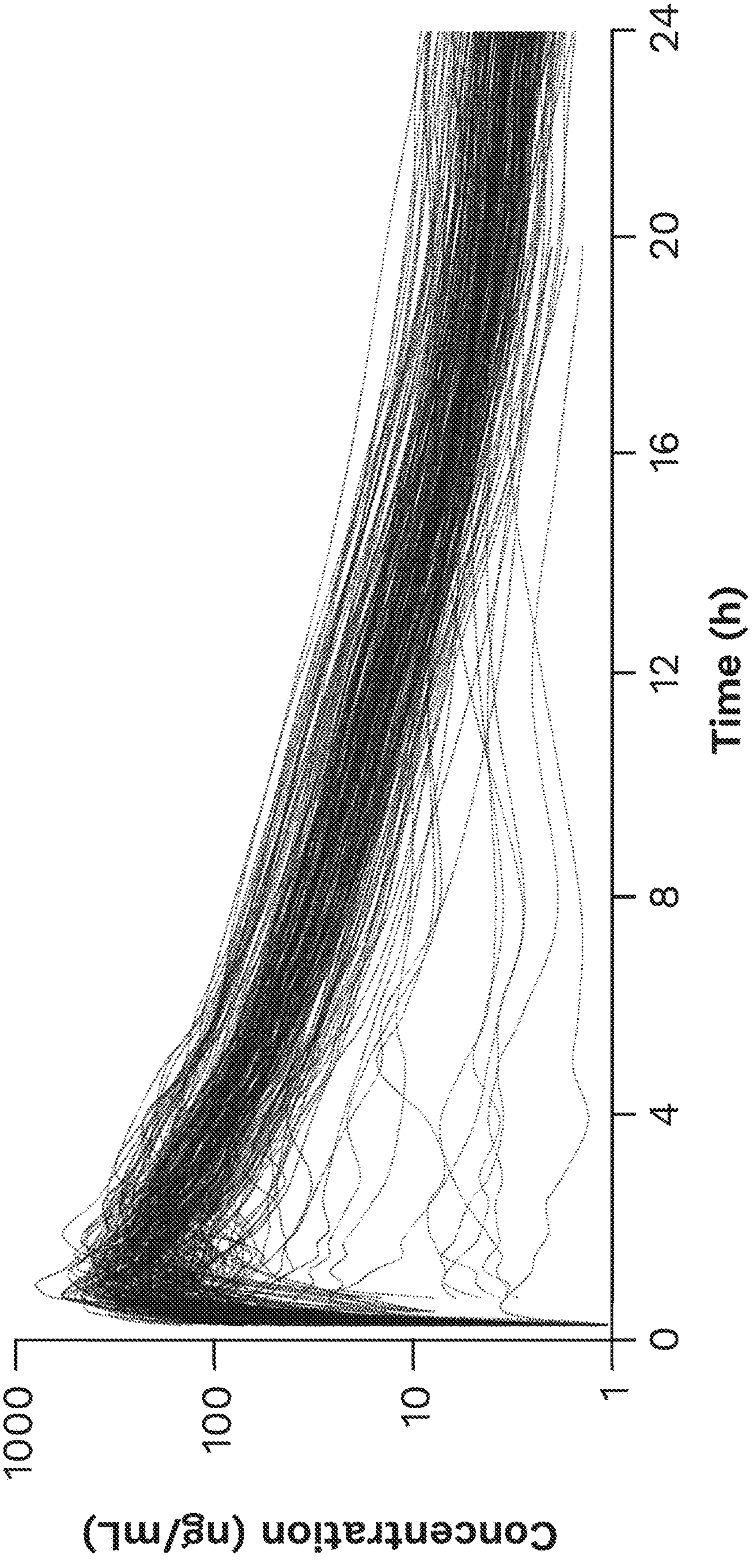
FIG. 17 provides individual plasma concentration time of dasatinib following a single dose oral administration of Reference Formulation (140 mg crystalline dasatinib) under fasting conditions.

In addition, results from this study indicate that Test Formulation was not associated with anomalously low exposure in any of the 107 subjects after administration of Test Formulation 100 mg (FIG. 16), while this phenomenon was observed in 2 of the 104 subjects after administration of Sprycel 140 mg (FIG. 17). These anomalously low exposure profiles are seen randomly with Sprycel, between and within healthy subjects and/or patients. This phenomenon is described in the EMA product-specific bioequivalence guidance for dasatinib as "low-tier" patient profiles, as well as Chandani.

The intra-subject CV % for AUC(0-24h) after Sprycel (dasatinib monohydrate) 140 mg (Reference-to-Reference) was approximately 3-fold greater than Test Formulation (Test-to-Test).

The intra-subject CV % for AUC(0-∞) after Sprycel (dasatinib monohydrate) 140 mg (Reference-to-Reference) was approximately 2.5-fold greater than Test Formulation (Test-to-Test).

The intra-subject CV % for Cmax after Sprycel (dasatinib monohydrate) 140 mg (Reference-to-Reference) was approximately 2-fold greater than Test Formulation (Test-to-Test).

As a point of reference, FIG. 18 presents data from individualized plasma concentrations for tested subjects comparing the Test Formulation (100 mg) to the Reference (Sprycel, 140 mg) and the observed plasma concentration values (Cmax, C2h, and C24h) reported in ng/m L. The reported values for 100 mg Test and 140 mg Reference represent observed values receiving 2 tablets during separate periods. The reported values for 70 mg Test and 100 mg Reference represent estimated values (indicated by asterisk) based on the observed values, which is acceptable given the dose-proportionality.

As a point of reference, the FIG. 18 data shows that the Test Formulation (100 mg) resulted in 208 observed individual Cmax-values (or 100% of observables for Test)>50 ng/mL, but no Cmax values≤50 mg/m L. It also may be seen that Reference Formulation (Sprycel, 140 mg) resulted in 197 observed individual Cmax-values (or 96% of observables for Reference)>50 ng/mL and 9 Cmax-values (or 4% of observables for Reference)≤50 ng/mL.

A further examination of the C24h (or Cmin) values depicted in FIG. 18 show substantial differences between Test and Reference. For instance, it was observed that 89 observed individual C24h-values (or 43% of observables for Test) were ≤2.5 ng/mL. In contrast, C24h-values (or 52% of observables for Reference) were ≤2.5 ng/mL. As stated above, a plasma trough concentration (C0) less than 2.5 ng/mL may avoid the incidence of pleural effusion. Miura at 645. Minimum plasma concentration (Cmin, or C24h) is considered to be an alternative expression for plasma trough concentration (C0). Thus, the FIG. 18 C24h-values show that administration of Test Formulation (100 mg) has a substantial proportion of individualized doses with trough concentrations of ≤2.5 ng/mL when compared to Sprycel (140 mg). This is even more evident when one considers the estimated values for the Test Formulation (70 mg) where 163 estimated individual C24h-values (78% of estimated observables for Test) were ≤2.5 ng/mL, while 126 estimated individual C24h-values (61% of estimated observables for Reference) were ≤2.5 ng/m L.

These results show that administration of Test Formulation provides for a greater percentage of C24h (or Cmin)≤to about 2.5 ng/mL when compared to administration of an equivalent dosage amount of the conventional crystalline dasatinib formulation (e.g., Sprycel), where C24h (or Cmin) corresponds to the dasatinib plasma concentration after 24-hours dosing. And again, with reference to FIG. 18, observed C24h values less than or equal to 2.5 ng/mL for Test Formulation (100 mg) resulted in a 1.7- to 1.9-fold improvement compared to conventional crystalline dasatinib formulation (Sprycel, 140 mg). Further, estimated C24h values less than or equal to 2.5 ng/mL for Test Formulation (70 mg) resulted in a 1.3-fold improvement compared to conventional crystalline dasatinib formulation (Sprycel, 100 mg) and estimated C24h values less than or equal to 1.5 ng/mL for Test Formulation (70 mg) resulted in a 2.3-fold improvement compared to conventional crystalline dasatinib formulation (Sprycel, 100 mg).

TABLE 2

| Overall Intra-subject Variability in Pharmacokinetics of Sprycel and Test Formulation | | | |
|---|---|---|---|
| | Treatment Mean Intra-subject CV % | | |
| | $C_{max}$ | AUC(0-24 h) | AUC(0-∞) |
| Sprycel (Reference) | 60.10 | 41.45 | 34.56 |
| Test Formulation | 28.79 | 14.16 | 13.92 |

Similarly, there was considerably greater inter-subject variability (CV %) in Cmax, AUC(0-24h) and AUC(0-∞) after fasted state administration of Sprycel (dasatinib monohydrate) 140 mg, when compared with Dasatinib 100 mg Test Formulation.

The inter-subject CV % for AUC(0-24h) after Sprycel (dasatinib monohydrate) 140 mg was approximately 4.5-fold greater than Test Formulation.

The inter-subject CV % for AUC(0-∞) after Sprycel (dasatinib monohydrate) 140 mg was approximately 4.3-fold greater than Test Formulation.

The inter-subject CV % for Cmax after Sprycel (dasatinib monohydrate) 140 mg was approximately 4.8-fold greater than Test Formulation.

TABLE 3

| Overall Inter-subject Variability in Pharmacokinetics of Sprycel and Test Formulation | | | |
|---|---|---|---|
| | Treatment Mean Inter-subject CV % | | |
| | $C_{max}$ | AUC(0-24 h) | AUC(0-∞) |
| Sprycel (Reference) | 58.30 | 38.91 | 36.48 |
| Test Formulation | 12.25 | 8.69 | 8.57 |

Figure 7:
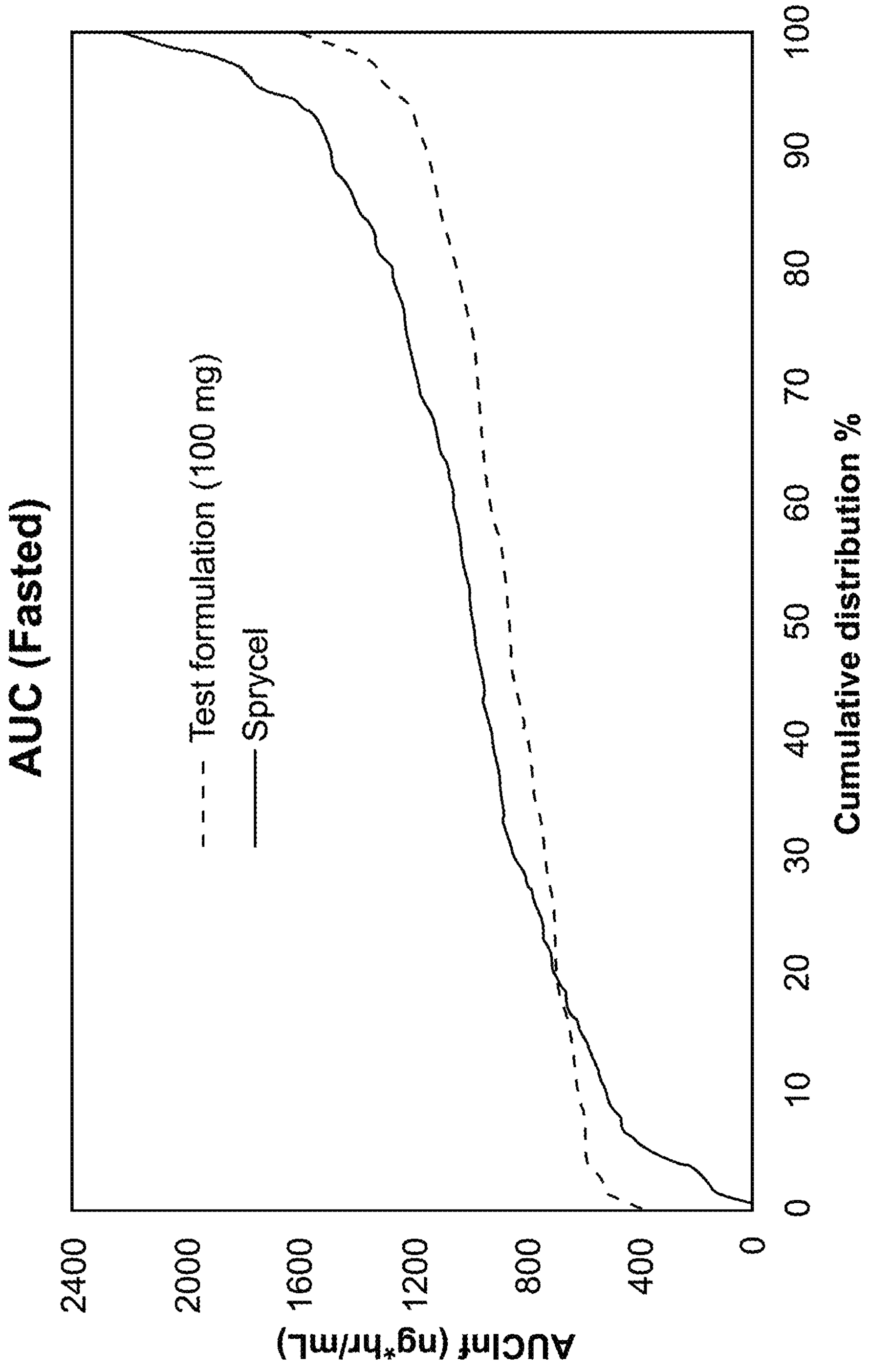
FIG. 7 provides cumulative distribution of AUC(0-∞) (ng·h/mL) of Test Formulation 100 mg tablets and Sprycel (reference product) 140 mg tablets in healthy adult subjects in the fasting state.

FIG. 7 shows the Cumulative Distribution of AUC in a Single dose full replicate crossover comparative bioavailability study of Test Formulation 100 mg tablets and Sprycel (reference product) 140 mg tablets in healthy adult subjects in the fasting state.

Figure 8:
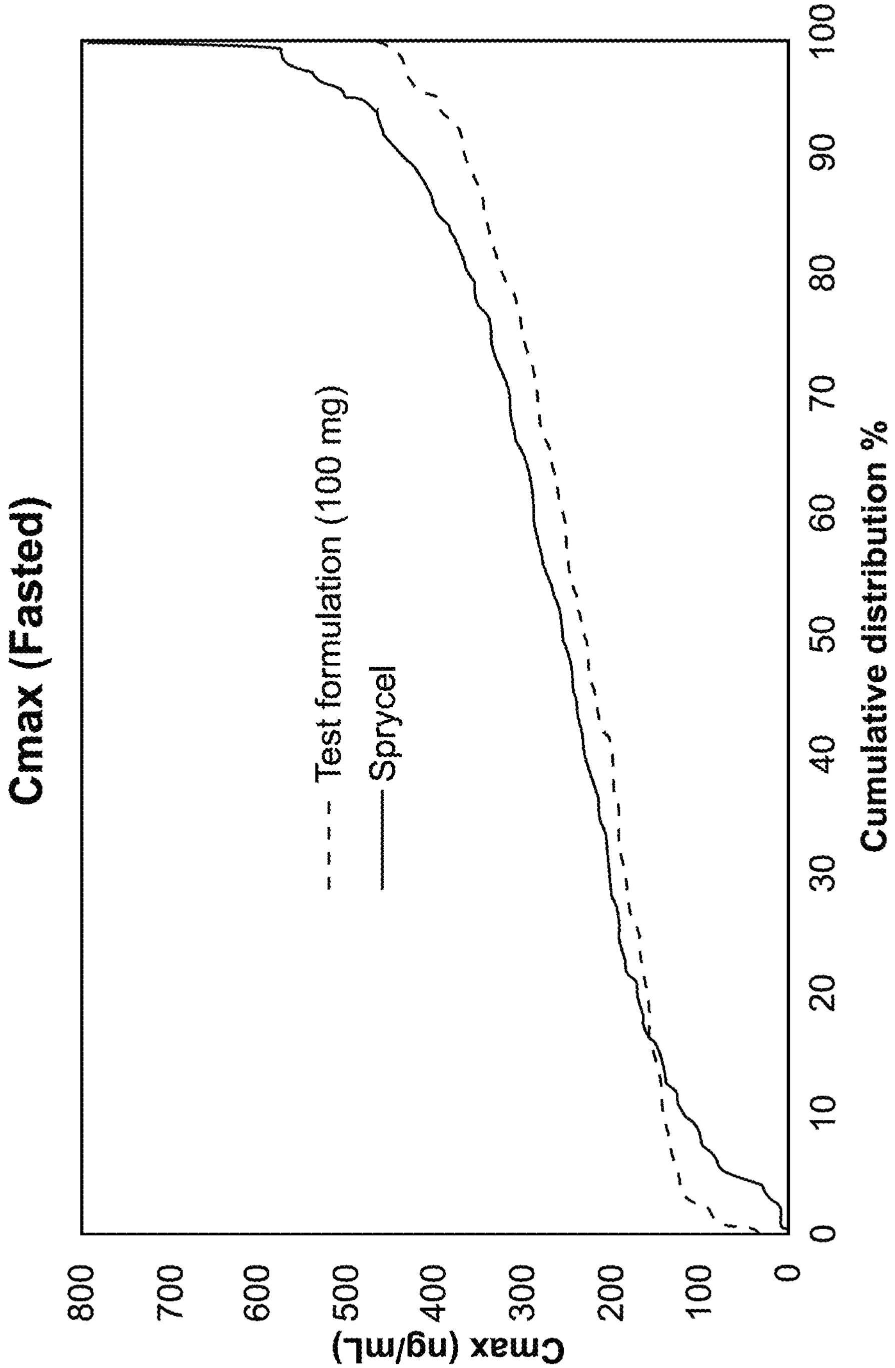
FIG. 8 provides cumulative distribution of Cmax of Test Formulation 100 mg tablets and Sprycel (reference product) 140 mg tablets in healthy adult subjects in the fasting state.

FIG. 8 shows the Cumulative Distribution of Cmax in a single dose full replicate crossover comparative bioavailability study of Test Formulation 100 mg tablets and Sprycel (reference product) 140 mg tablets in healthy adult subjects in the fasting state.

Gastric Acid Reducing Agent Drug-Drug Interaction

A drug-drug interaction (DDI) study of Dasatinib 90 mg Tablets Test Formulation with or without 5-day repeated dose of omeprazole 40 mg was conducted in healthy subjects and showed no DDI. The geometric mean ratios for Cmax, AUC(0-24h), AUC(0-∞) were 85.7, 106.8% and 107.5%, respectively, indicating an absence of an effect of omeprazole on the PKs of Test Formulation with a mean decrease of 14% in Cmax (geometric mean 119 ng/mL on Day 6 compared to 138 ng/mL on Day 1), and 7% increase in the extent of systemic exposure (geometric mean AUC (0-∞)466 ng·hr/mL on Day 6 compared to 434 ng·hr/mL on Day 1). No dosing adjustments are therefore necessary when Test Formulation is co-administered with omeprazole or other gastric acid reducing agents.

TABLE 4

| PK Parameters of Dasatinib Plus Omeprazole vs Dasatinib Alone | | | | | | |
|---|---|---|---|---|---|---|
| | Ln-transformed Data (n = 16) (Dasatinib + Omeprazole (Day 6) vs. Dasatinib alone (Day 1)) | | | | | |
| | Geometric Mean | | | | | |
| Parameter (Unit) | Dasatinib alone (Day 1) | Dasatinib + Omeprazole (Day 6) | (Day 6/Day 1) Ratio (%) | 90% CI | Intra-Subject CV (%) | Power (%) |
| Cmax (ng/mL) | 138.4157 | 118.5866 | 85.67 | 67.20-109.22 | 42.1 | 45 |
| AUC(0-24 h) (ng · hr/mL) | 426.2652 | 455.0639 | 106.76 | 90.26-126.26 | 28.5 | 71 |
| AUC(0-∞) (ng · hr/mL) | 433.6406 | 466.313 | 107.53 | 90.99-127.09 | 28.4 | 71 |

According to FDA draft guidance (see GFI, Evaluation of Gastric pH), PPIs represent a worst-case scenario for pH dependent DDIs. Consequently, a negative result from such a study indicates the lack of a pH dependent DDI for an investigational drug. The results are thus able to support the label claim regarding use with or without concomitant acid reducing agents (ARAs). Said study confirms a previous non-GLP fasted dog study conducted which demonstrated poor oral absorption of dasatinib, given as Sprycel tablet, after famotidine administration, when compared with a prototype dasatinib amorphous solid dispersion capsule. In this study, the Cmax and AUC after Sprycel tablets were 108-fold and 83-fold lower, respectively, when compared with dasatinib amorphous solid dispersion. These results are further supported by prior studies demonstrating a significant reduction in dasatinib bioavailability with ARAs, when given as Sprycel:

(i) famotidine pretreatment to the dog resulting in mostly undetectable plasma concentrations of dasatinib after Sprycel administration (see Pang);

(ii) famotidine pretreatment 10 hours prior to Sprycel to healthy subjects resulting in a dasatinib AUC decrease of approximately 60% (see Eley); and (iii) dasatinib steady-state Cmax and AUC reduced by 42% and 43%, respectively when Sprycel dosed 22 hours after repeated dose omeprazole pretreatment (see Sprycel Label).

SUMMARY

Potential Therapeutic Advantages of Test Formulation Relative to Sprycel:

Dasatinib 100 mg tablet Test Formulation shows improved solubility compared to Sprycel, RLD, and more consistent bioavailability under various pH conditions. Dasatinib 100 mg tablet Test Formulation shows a greater apparent solubility, a faster dissolution rate and an improved oral bioavailability compared to Sprycel.

The main clinical study data obtained for dasatinib (Test Formulation) indicate:

A more bioavailable product, i.e., 100 mg of Test Formulation shows similar rate and extent of exposure as 140 mg of Sprycel An absence of food effect on its extent of exposure (Fed/Fast AUCt ratios within ±5% for Test Formulation versus±15% for Sprycel)

An absence of DDI with the PPI omeprazole

Lower intra- and inter-subject variability in both rate (Cmax) and extent (AUC) of absorption and greater consistency in the AUC in the fasted state, when compared with Sprycel (Sprycel AUC intra-CV ~30-60% vs. Test Formulation of ~10-15%).

With increased bioavailability, 100 mg of Test Formulation will allow for use of a lower tablet strength than Sprycel 140 mg Tablets.

With reduced within- and between-subject variability in bioavailability in the fasting state, 100 mg of Test Formulation is also expected to offer more consistent oral absorption when compared to Sprycel.

Additionally, the gastrointestinal absorption and PK of orally administered weakly basic drugs such as dasatinib are characterized by strong pH dependent solubility. With a less pH dependent solubility, 100 mg of Test Formulation is expected to allow use with or without concurrent ARAs such as PPIs, H2 antagonists, and antacids, and to have more consistent absorption under various pH conditions, with overall safety and efficacy comparable to Sprycel for the treatment of advanced chronic myeloid leukemia (CML) and acute lymphoblastic leukemia (ALL).

Clinical Benefits

In view of the bioequivalence of Dasatinib 100 mg Tablets Test Formulation and can be expected to have an efficacy profile comparable to Sprycel 140 mg.

The Test Formulation is expected to have a similar overall efficacy and safety when compared to Sprycel, with the following added potential clinical benefits:

Unlike Sprycel, it shows no DDI with omeprazole and therefore can be safely taken with ARAs which are commonly co-administered to patients receiving anticancer therapy, including Sprycel for CML (see Budha). Use of ARAs is widely associated with reduced bioavailability of Sprycel (see Eley and Sprycel Label) and can potentially reduce anti-tumor effects that may affect survival outcomes (see Indini, Smelick, and Larfors).

It is approximately 40% more bioavailable than Sprycel in the fasting state, allowing for a lower tablet strength.

It shows reduced intra- and inter-subject variability in Cmax and AUC in the fasting state when compared with Sprycel, the latter a highly variable formulation under fasting conditions.

It does not exhibit anomalously low systemic exposure profiles, which the EMA has referred to as "low-tier" patient profiles, when compared with Sprycel.

Food Effect

Objective: The objective of this analysis was to investigate the effect of food on the single-dose PK of Test Formulation using fasted and fed PK data from two studies, referred to as "Fasted Study" and "Fed Study," respectively below.

Methodology. Since the PK parameters following the oral administration of Test Formulation in fasting and fed conditions were obtained from two different studies (Fasted Study and Fed Study, respectively), the PK data were analyzed using an analysis of variance (ANOVA), which considered the data as if they were collected in a parallel design.

Both studies were fully replicate studies and therefore subjects were dosed with Test Formulation on two occasions. The PK population in this analysis included subjects who received Test Formulation on two occasions; subjects who received Test Formulation only once were not included in this analysis.

In the current analysis, data from the PK population of the Fasted Study and Fed Study were considered "Reference" Treatment and "Test" Treatment, respectively.

The food effect was assessed by evaluating natural log-transformations, least-squares geometric means (LSmeans), two-sided 90% CIs and Fed/Fast ratios, for AUC(0-24h) and AUC(0-∞), as well as Cmax values. For each parameter, the value used for the subject was the geometric mean of the two values that were available for each subject. The use of geometric means is consistent with the assumption that PK parameters are In normally distributed. Subjects with only one period of data were not included in the ANOVA, as this would incorrectly imply that singular data have the same weight as subjects with replicate values for the parameter.

Results

In the Fasted Study, 51 subjects received Test Formulation on at least one occasion under fasting conditions, of whom 44 received Test Formulation on both occasions.

In the Fed Study, 32 subjects received Test Formulation on at least one occasion under fed conditions, of whom 27 received Test Formulation on both occasions.

Food Effect Assessment

Figure 9A:
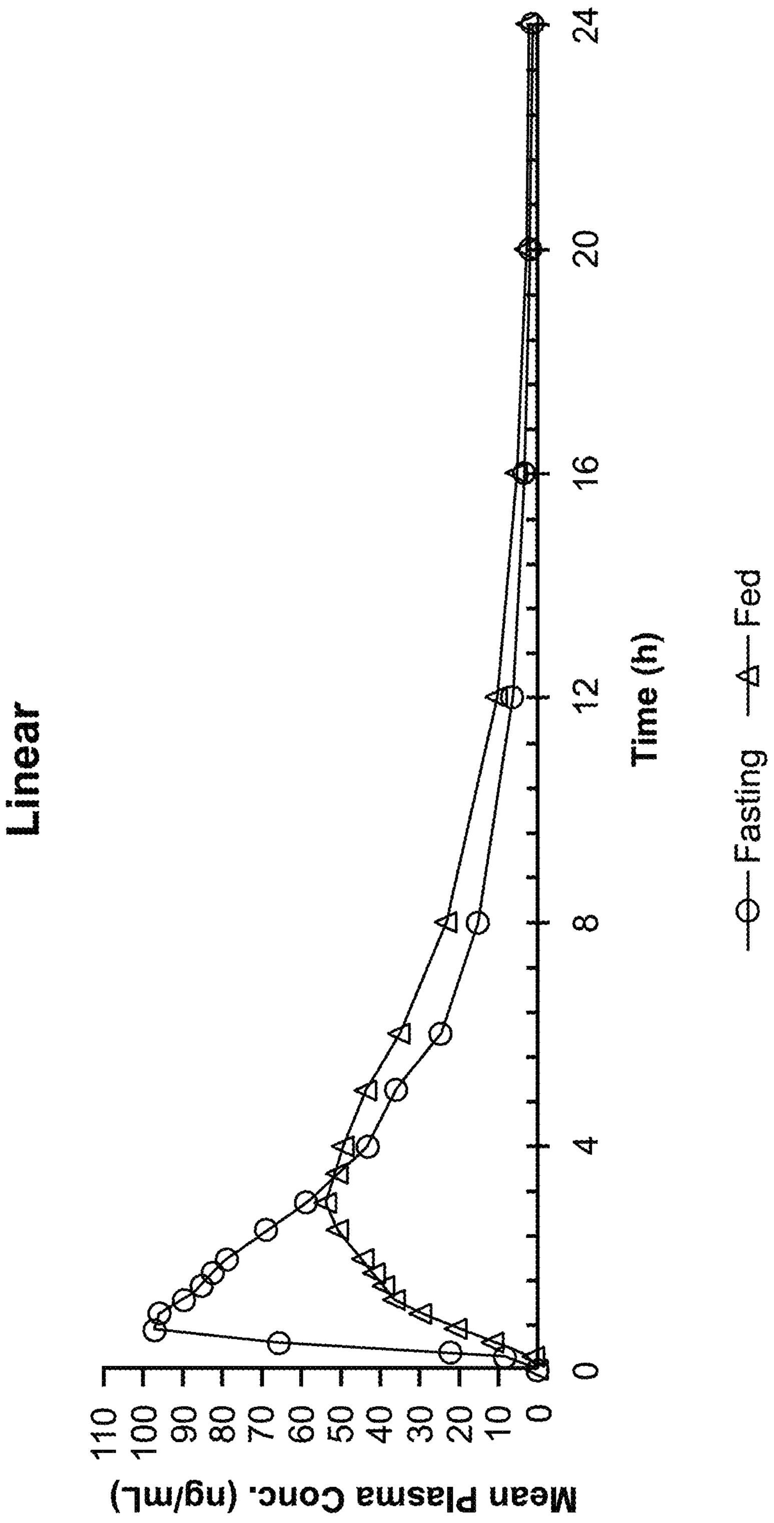
FIG. 9A provides Mean Plasma Concentration-Time Profiles After Single-Dose Administration of Test Formulation under Fasting and Fed Conditions using linear scale.
Figure 9B:
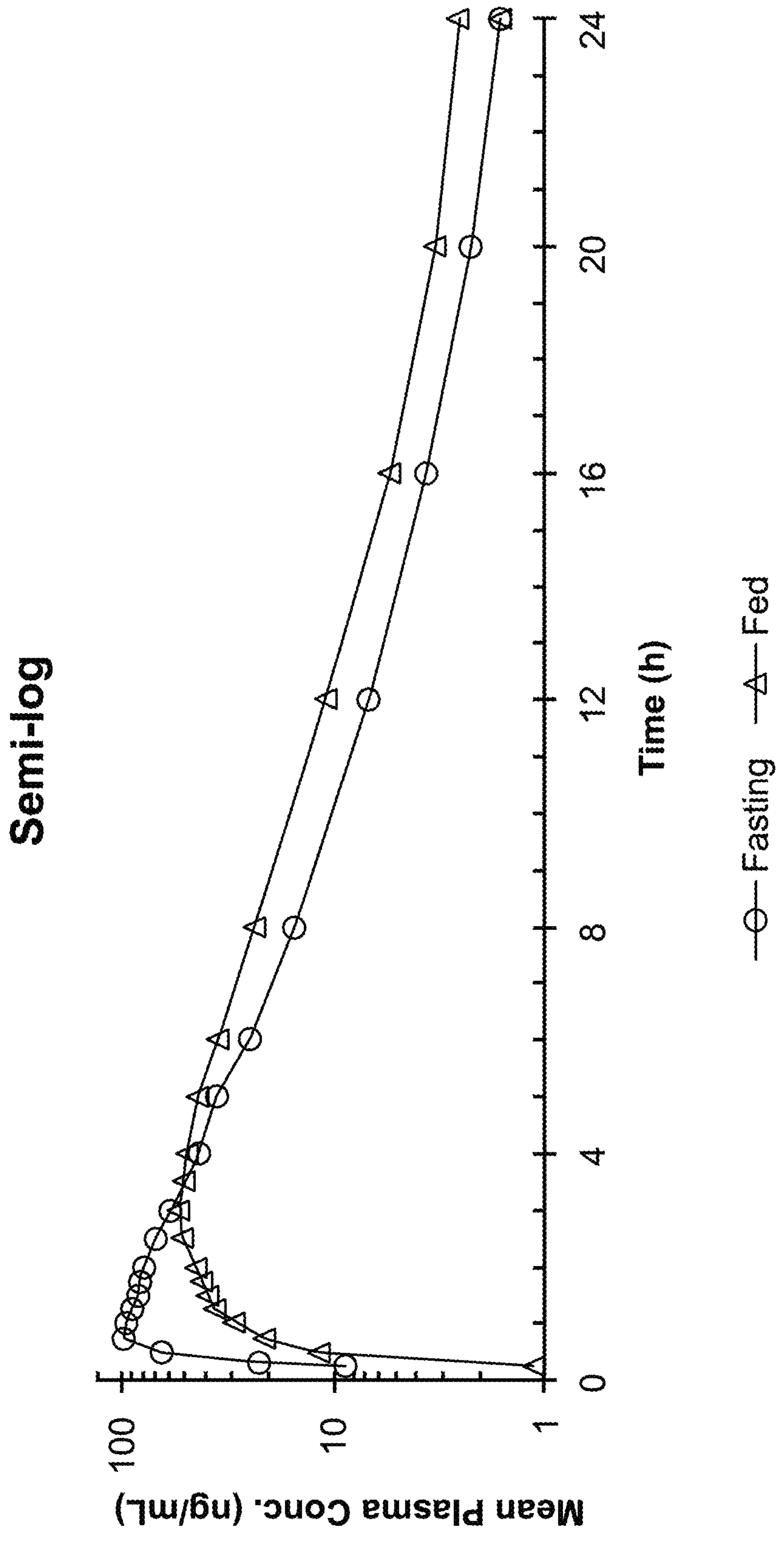
FIG. 9B provides Mean Plasma Concentration-Time Profiles After Single-Dose Administration of Test Formulation under Fasting and Fed Conditions using semi-logarithmic scale.

Mean plasma concentration-time profiles after single-dose administration of Test Formulation under fasting and fed conditions are displayed in FIG. 9. Subjects receiving Test Formulation under fasting conditions were not the same as those receiving Test Formulation under fed conditions.

Results of the food effect statistical analysis are summarized in Table 5.

TABLE 5

Summary of the Statistical Analysis of Dasatinib Under Fasting (n = 44) vs. Fed (n = 27) Conditions

| | LSmeans [a] | | Fed/Fast Ratio | | 90% CI [c] | |
|---|---|---|---|---|---|---|
| Parameter | Fed | Fasted | (%) | CV% [b] | Lower | Upper |
| AUC(0-24 h) (ng · h/mL) | 413 | 433 | 95.30 | 28.8 | 84.94 | 106.91 |
| AUC(0-∞) (ng · h/mL) | 431 | 446 | 96.64 | 28.5 | 86.23 | 108.30 |
| $C_{max}$ (ng/mL) | 67 | 127 | 52.92 | 36.9 | 45.75 | 61.21 |

[a] Least-squares geometric means.
[b] Residual variability CV % = 100*SQRT(eMSE-1), where MSE is the mean square error term from the ANOVA.
[c] Confidence intervals around the ratios.

Discussion

Results from this analysis showed that the Fed/Fast ratios and 90% CIs for AUC(0-t) (e.g., t=24 h) and AUC(0-∞) were well within the clinical equivalence range of to 125.00% and the ratios were less than 5% away from unity (100%). Therefore, a high-fat/high-calorie breakfast did not have any significant effect on the overall extent of exposure of dasatinib following single-dose administration of Test Formulation.

Food did however delay the time to peak plasma concentration by approximately 2 h, resulting in a large difference in the observed Cmax. For Cmax, the Fed/Fast ratios and 90% CIs fell outside the equivalence range of 80.00% to 125.00%. Fed/Fast ratio was ~53%, indicating that food appeared to reduce the maximum exposure by almost 50%.

Since Cmax during the fed state is lower than in the fasted state, it is not expected to have any adverse safety implications for the use of Test Formulation when taken orally with food versus in a fasted state. From the safety data collected, Test Formulation was generally safe and well tolerated by the healthy subjects. Furthermore, no new or unexpected adverse reactions were observed.

The exposure-response relationship of dasatinib indicates that most of the efficacy of dasatinib is related to AUC or to the administered dose. The results of the efficacy studies submitted for the Sprycel NDA suggest that a higher Cmax may contribute to efficacy in addition to the dose or exposure, but in all likelihood only a small 5-10% additional effect. The impact of a 50% lower observed mean Cmax under fed conditions on the clinical efficacy of Test Formulation is therefore expected to be of no significant clinical relevance.

This is consistent with the analyses and recommendations from the Sprycel NDA in which a 25% decrease in Cmax with food was judged to be of no clinical relevance for dasatinib. The food effect study for Sprycel showed that a high-fat/high-calorie meal increased the extent of exposure (AUC) by 14% while decreasing the Cmax by 24% (see Sprycel Clinical Review at 41). These results were judged to be not clinically relevant by the Applicant Bristol Myers Squibb and the FDA approved the label for Sprycel which specifies that Sprycel can be administered regardless of food intake. Due to a formulation change after the efficacy data from the first 84 patients were collected, the Applicant for Sprycel conducted a PK study comparing the 20 and 50 mg dose strengths of proposed commercial formulations with the one used for the first 84 patients. The results from this PK study indicated that the Cmax ratios of the proposed commercial formulations (20 mg and 50 mg) were between 30 to 40% less than the formulation for the first 84 patients. Despite these significant differences, efficacy data from all subjects were included, further indicating that a significant drop of the Cmax was judged by the FDA Sprycel NDA clinical reviewer to not significantly affect the efficacy of Sprycel.

In view of the results related to the food effect studies, the following conclusions may be made.

Test Formulation shows an absence of food effect on its extent of exposure (Fed/Fast AUC ratios within ±5% for Test Formulation versus±15% for Sprycel).

The administration of a high-fat/high-calorie meal did not have a significant effect versus the fasting conditions on the extent of systemic exposure (i.e., AUC(0-t), e.g., AUC(0-24h), and AUC(0-∞) of dasatinib following the single-dose administration of Test Formulation. The administration of food did, however, delay the absorption of dasatinib and result in a Cmax that was reduced by 47%. Given that the efficacy of dasatinib is mostly related to the administered dose and overall systemic exposure, the impact of the lower Test Formulation Cmax during fed conditions is expected to be of minimal clinical relevance. Therefore, Test Formulation may be recommended to be administered with or without food.

Dissolution

Extensive in vitro dissolution testing of Test Formulation, 100 mg has been performed. During the pharmaceutical development of the formulation, a 0.01 M HCl (pH 2) USP II method was used for optimization of the rapid dissolution of the formulation. Dissolution testing of three batches manufactured at various compression forces was performed using both the pH 2 method and the FDA recommended method for dasatinib (pH 4.0 acetate buffer containing 1% Triton X-100) (see Dasatinib Dissolution Method). The dissolution results are shown in Table 6.

TABLE 6

Dissolution results (mean, min and max) of three commercial scale batches of Test Formulation using the pH 2 (n = 6) and FDA recommended methods (n = 6)

| Time | % Dissolved by Tablet Batch, Compression Force (kN) and Method | | | | | |
|---|---|---|---|---|---|---|
| | Batch 1 (15.7 kN) | | Batch 2 (20.3 kN) | | Batch 3 (21.5 kN) | |
| (min) | pH 2 | FDA | pH 2 | FDA | pH 2 | FDA |
| 10 | 86 (79-94) | 85 (80-88) | 82 (74-96) | 81 (75-86) | 77 (72-85) | 76 (71-83) |
| 15 | 96 (89-103) | 93 (88-98) | 102 (96-112) | 99 (96-104) | 91 (86-93) | 95 (93-98) |
| 30 | 102 (99-105) | 99 (96-103) | 105 (102-107) | 102 (100-107) | 98 (95-100) | 99 (96-101) |
| 45 | 102 (100-105) | 99 (97-103) | 105 (102-107) | 103 (101-108) | 98 (95-100) | 100 (96-101) |
| 60 | 103 (100-105) | 99 (97-103) | 105 (102-107) | 104 (101-107) | 98 (95-99) | 100 (96-102) |

Additional biorelevant in vitro dissolution testing of Test Formulation and the RLD, Sprycel, has been performed at several pH conditions to better understand the dissolution properties of the Test Formulation and the RLD. The results are summarized below.

During in vitro dissolution experiments at pH 1, it was observed that SPYRCEL 100 mg showed an unexpectedly high variability (relative standard deviation [RSD]=43% at 15 min) in dissolution rate. It was decided to repeat the testing using another batch of Sprycel 100 mg and the high variability was confirmed (RSD=34% at 15 min). In order to understand if the high variability was related to solubility of dasatinib, dissolution testing of Sprycel 20 mg was performed at the same conditions. A high variability (RSD=32% at 15 min) was also observed for the 20 mg strength, indicating that the high variability in dissolution rate for Sprycel at pH 1 was related to other product performance properties specific for Sprycel and not solubility.

Figure 10:
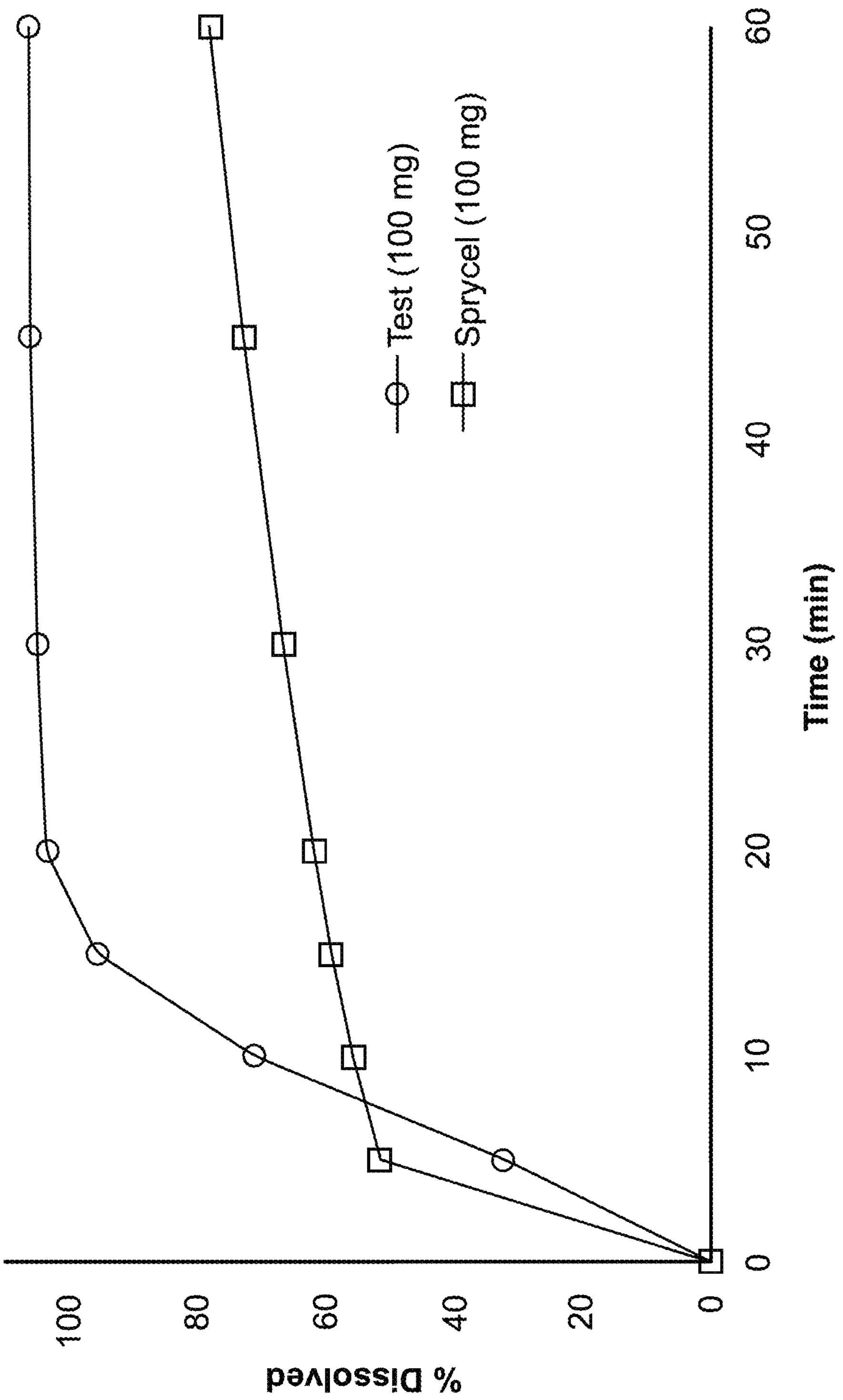
FIG. 10 provides dissolution of Test Formulation (100 mg, n=6) and Sprycel (100 mg, n=6+6) (pH 1; 500 mL, 50 rpm).

Average in vitro dissolution curves of Test Formulation and Sprycel (dasatinib monohydrate) 100 mg at pH 1 conditions are presented in FIG. 10. All Test tablets completely dissolved within 20 min. The variability of Test tablets was significantly lower (RSD=6% at 15 min) than for Sprycel 100 mg (RSD=43% at 15 min).

Figure 11:
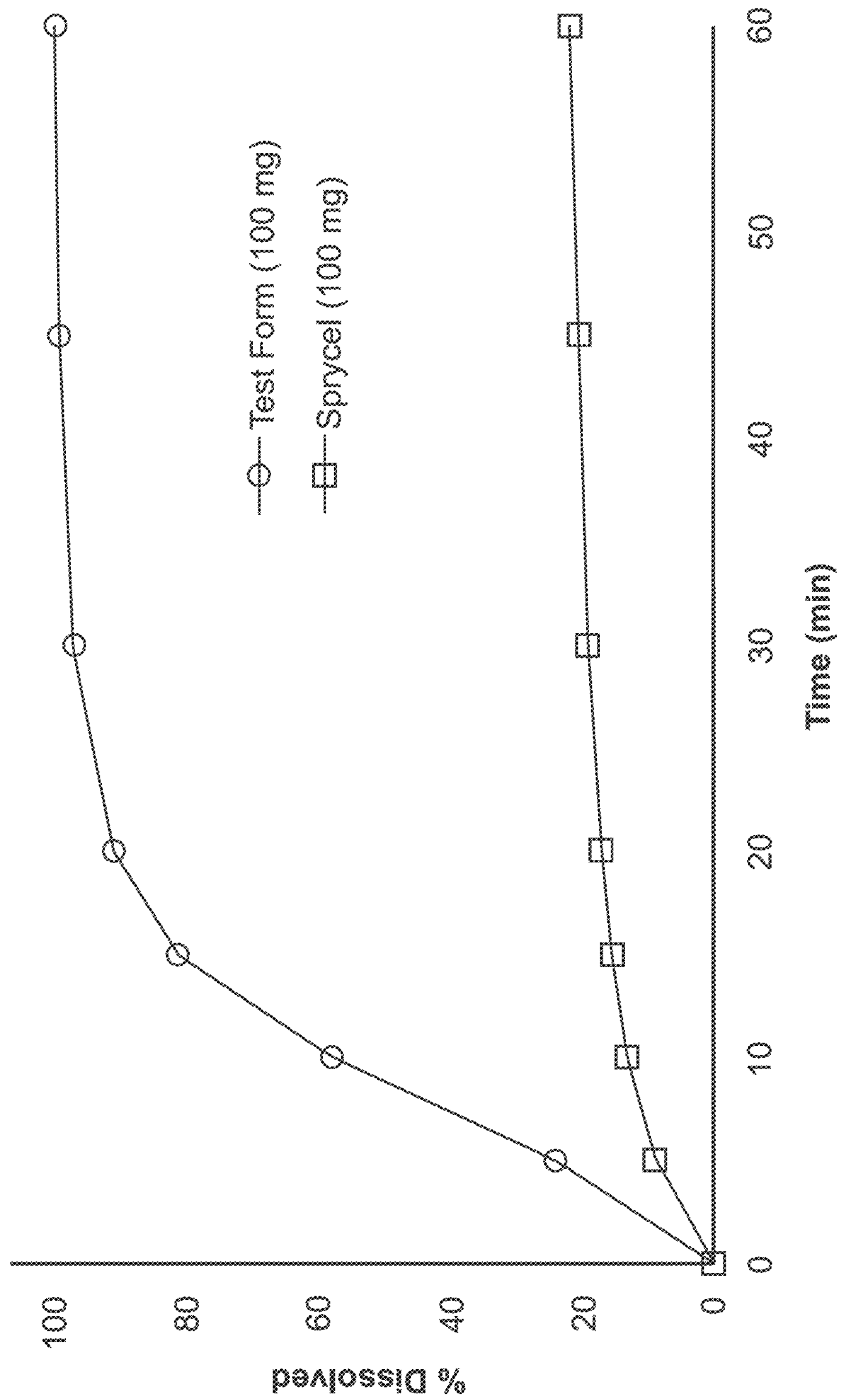
FIG. 11 provides dissolution (n=6) of Test Formulation (100 mg) and Sprycel 100 mg (pH 4.5; 500 mL, 50 rpm).
Figure 12:
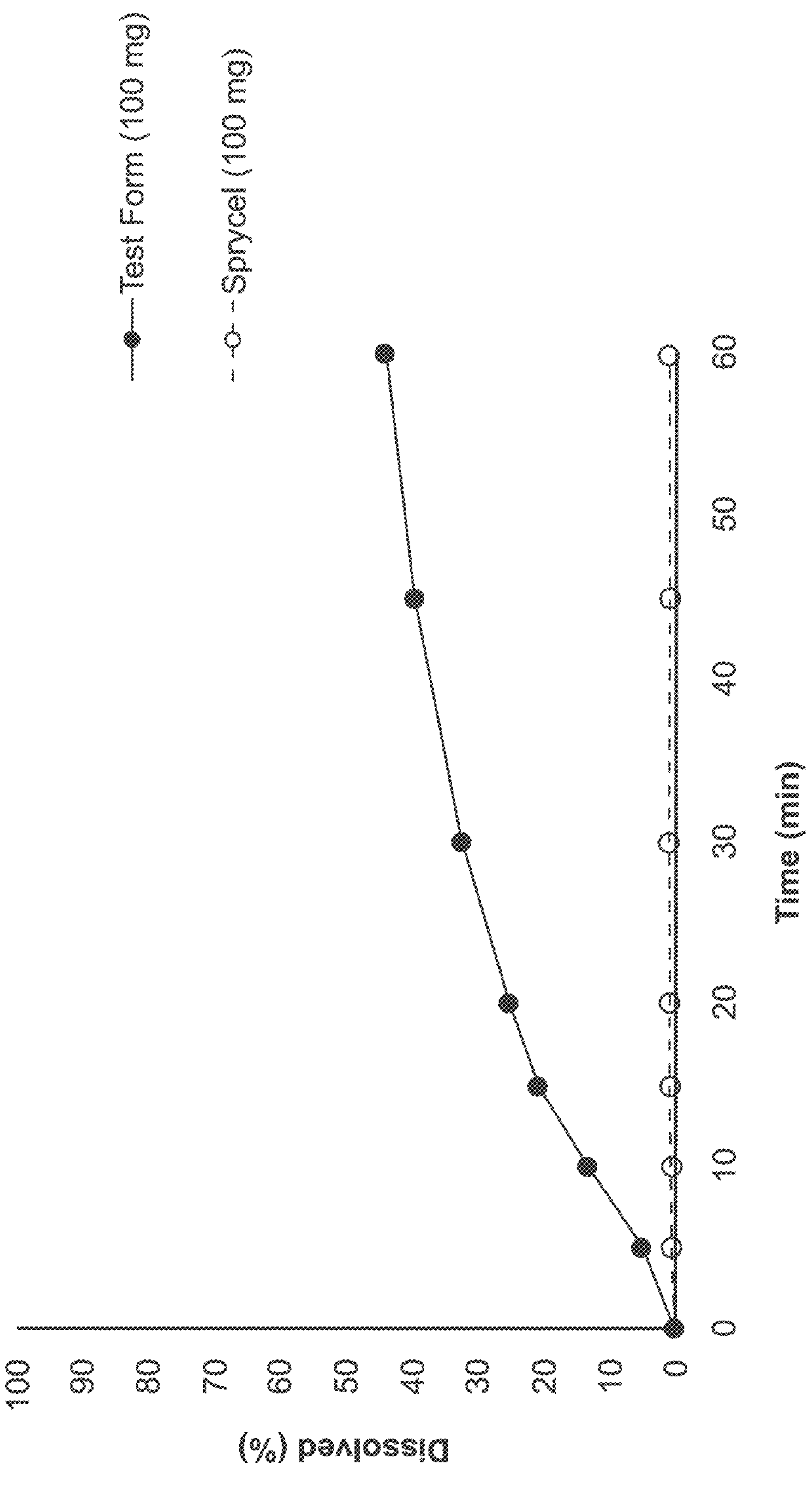
FIG. 12 provides dissolution (n=6) at pH 6.8 of Test Formulation 100 mg and Sprycel 100 mg (500 mL, 75 rpm).
Figure 15:
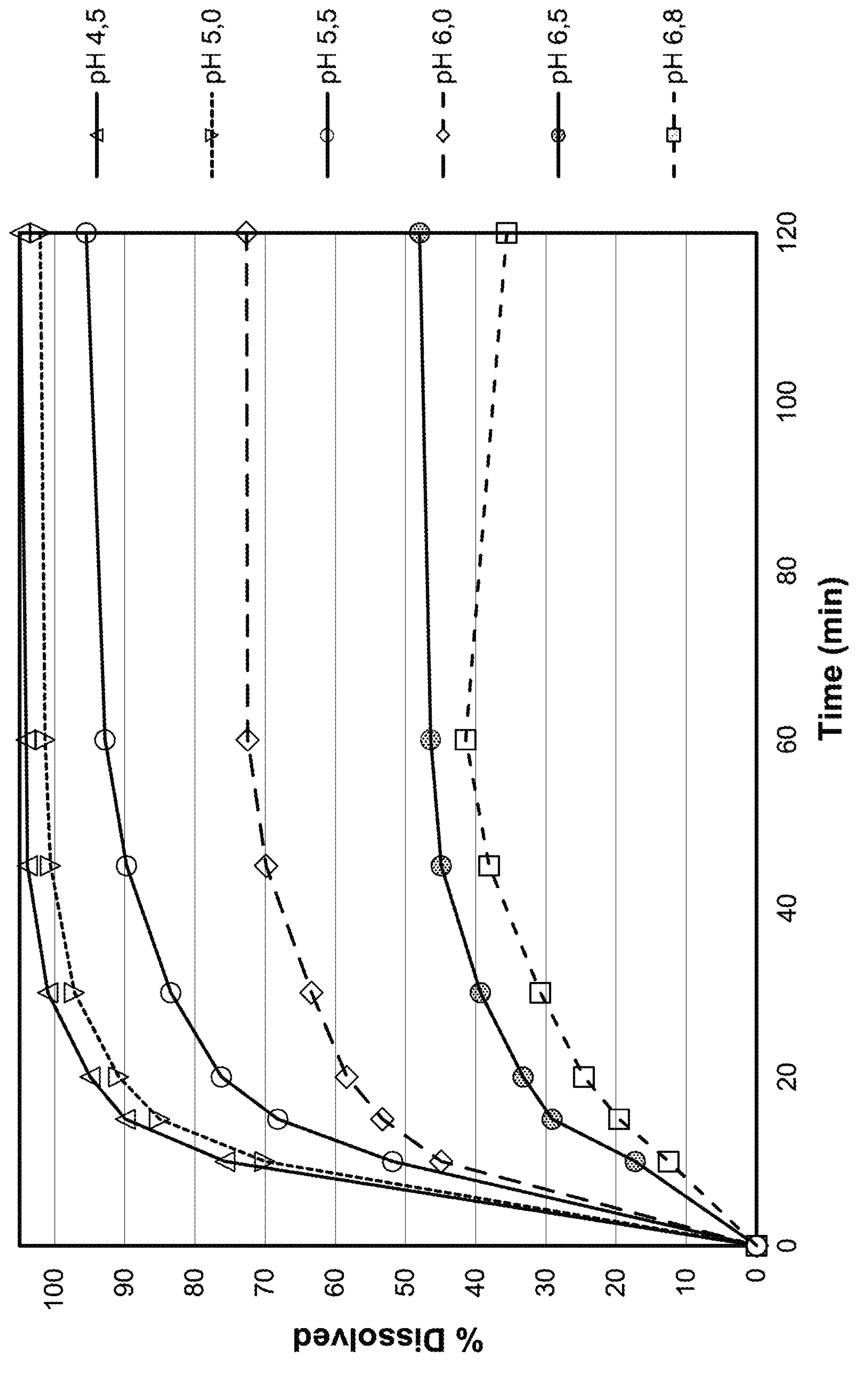
FIG. 15 provides dissolution of Test Formulation 100 mg tablet at various pH.

Dissolution testing of Dasatinib 100 mg Tablets Test Formulation and Sprycel at several pH values showed unexpectedly high dissolution rate variability for Sprycel. Average dissolution rates for Dasatinib 100 mg Tablets Test Formulation and Sprycel (dasatinib monohydrate) 100 mg at pH 1 and pH 4.5 in 500 mL buffers at 50 rpm are shown in FIG. 11 and FIG. 12, respectively. Dissolution of the Dasatinib Tablets Test Formulation and Sprycel 100 mg at various pH in a USP II (paddle) apparatus are shown in FIG. 15. Buffers in the pH range 4.5 to 6.8 were prepared and used as being relevant gastric pH following omeprazole administration. Dissolution media volume was 500 mL in all experiments and the stirring was set to 75 rpm. As seen in FIG. 15, the Dasatinib 100 mg Tablets Test Formulation dissolved completely within 60 minutes at pH 5.0. The observed difference in dissolution between Dasatinib 100 mg Tablets Test Formulation and Sprycel may explain the in vivo 40% greater bioavailability of the former under fasting conditions.

The high variability in in vitro dissolution rate for Sprycel at pH 1 was not observed at higher pHs. At pH 4.5, Sprycel was incompletely dissolved within 1 h, whereas Test Formulation was completely dissolved. At pH 6.8 Sprycel was mainly undissolved (<1%) after 1 h, while approximately 45% of Test Formulation was dissolved. The in vitro dissolution testing confirms that Test Formulation is much less sensitive to changes in gastrointestinal luminal pH when compared to Sprycel and that the variability in dissolution rate seen for the RLD at pH 1 is not seen for Test Formulation.

Figure 13:
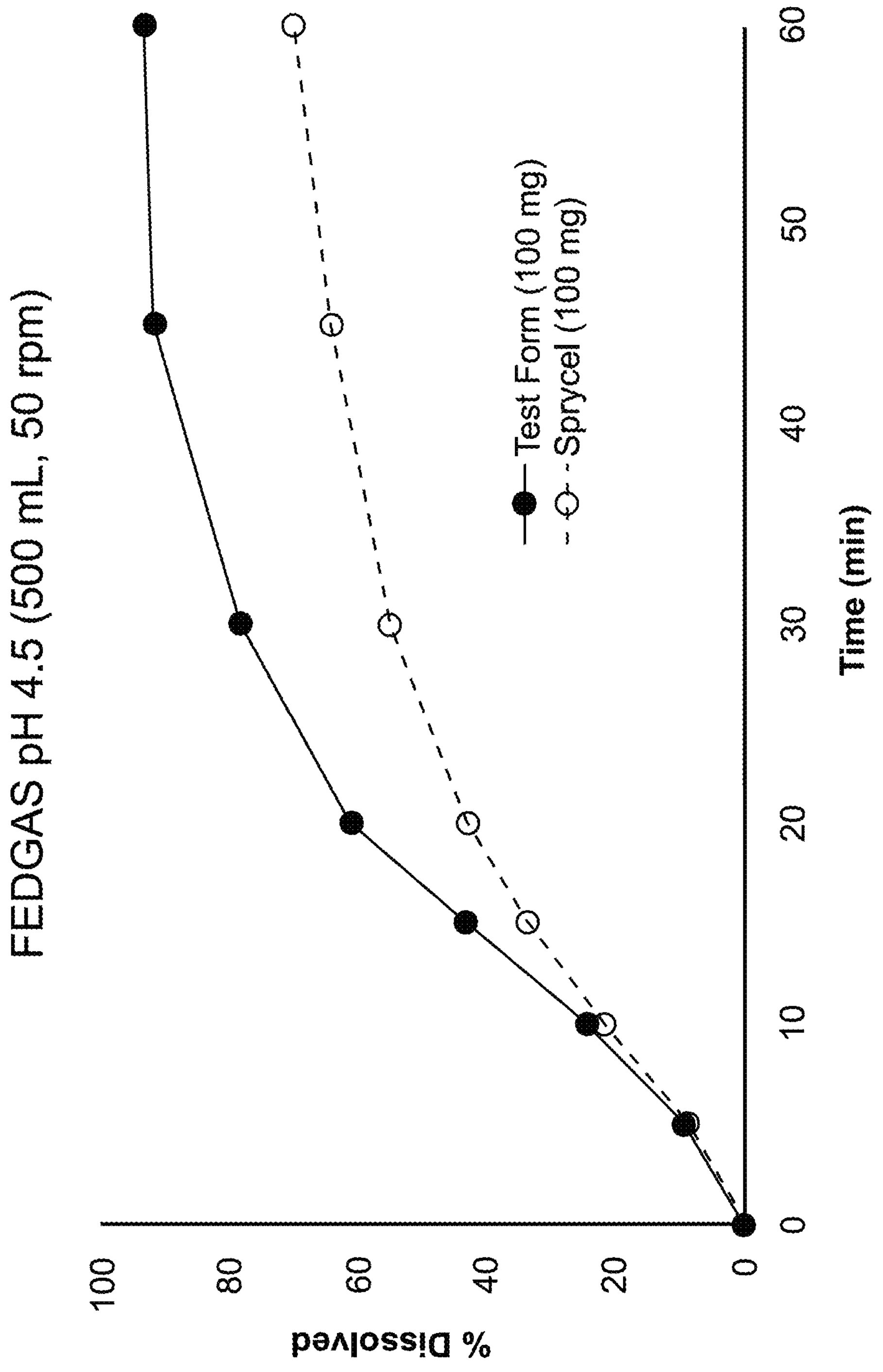
FIG. 13 provides dissolution (n=3+3) of Test Formulation 100 mg and Sprycel 100 mg in media simulating gastric conditions following a high-fat meal (pH 4.5, 500 mL, 50 rpm).

For an improved understanding of dissolution and absorption of dasatinib following a FDA recommended high fat meal, both Test Formulation and Sprycel 100 mg were tested in a dissolution medium (FEDGAS) that simulates the gastric conditions following a high-fat meal. This medium contains fat, carbohydrates, dietary fiber and bile salts in a pH 4.5 buffer. The dissolution results are presented in FIG. 13.

The in vitro dissolution of Sprycel was significantly higher but still incomplete in a medium simulating the gastric lumen following a high-fat meal when compared with the dissolution of Sprycel in plain pH 4.5 buffer. Test Formulation dissolved practically completely but at a slower rate in the simulated high fat meal gastric medium when compared to plain pH 4.5 buffer. This is believed to be due to the fact that the simulated high-fat meal gastric medium is an emulsion which reduces access to water needed for dissolving the ASD form of dasatinib, which the Test Formulation is based upon.

Figure 14:
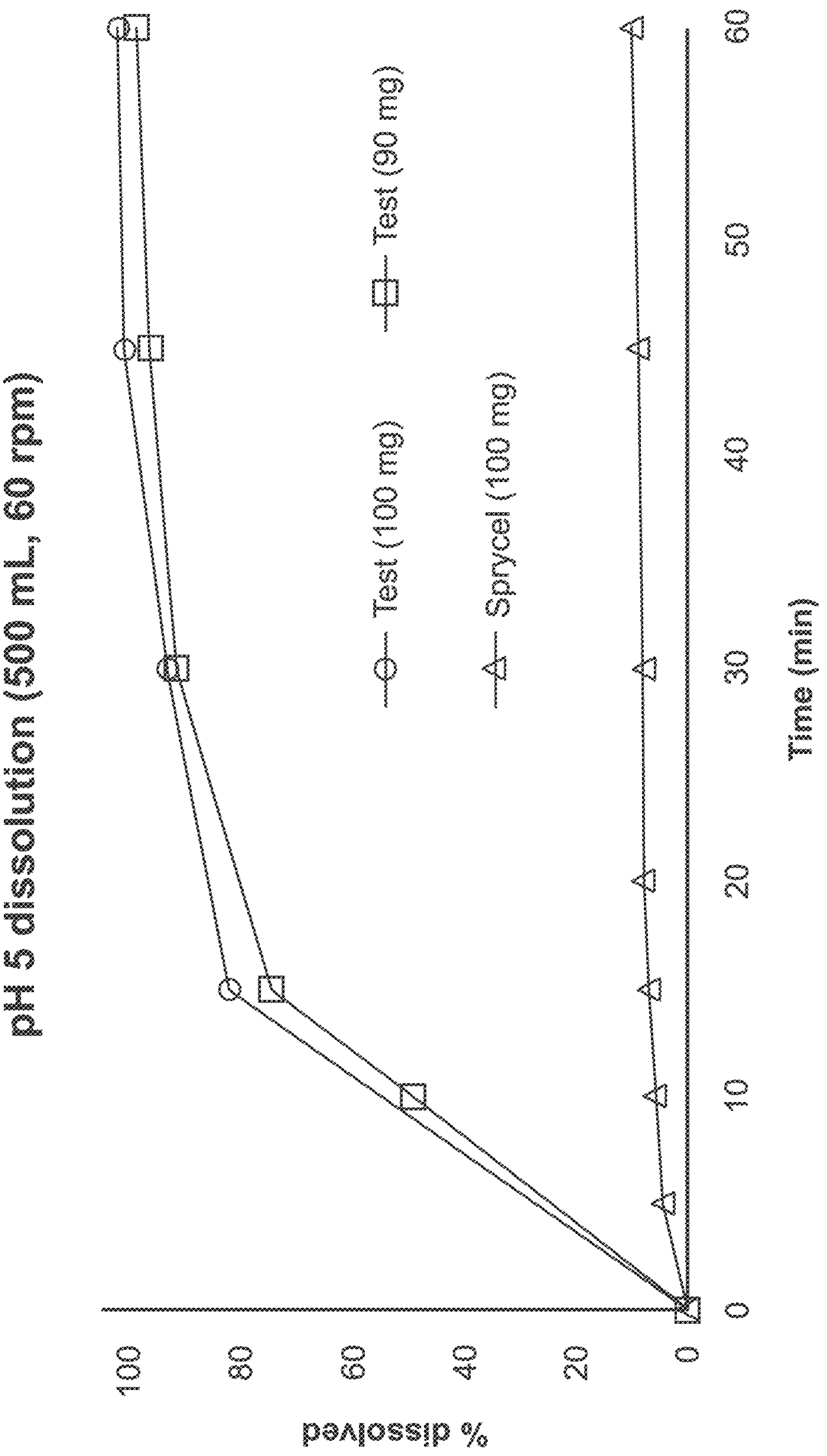
FIG. 14 provides dissolution of Test Formulation (90 mg/100 mg) and Sprycel (100 mg) at pH 5.0 (500 mL, 60 rpm) dissolution of Test Formulation and Sprycel at pH 5.0.

In connection to a clinical study in which Formulation 90 mg was co administered with oral omeprazole, a pH 5.0 in vitro dissolution method (500 mL, 60 rpm) was temporarily introduced. In vitro dissolution of Sprycel 100 mg and both Test Formulation mg and 100 mg tablets using this dissolution method are presented in FIG. 14. Both strengths of Test Formulation dissolved completely, although the dissolution rate was slightly decreased when compared to dissolution in the pH 4.5 buffer. Sprycel 100 mg was incompletely dissolved (approximately 10%) within 1 h under these conditions.

The in vitro (dissolution rate in acidic media) and in vivo (AUC) performance of Dasatinib 100 mg Tablets Test Formulation and Sprycel are consistent with the solubility profile of the crystalline base form of dasatinib—an increased pH in the stomach can be expected to limit the dissolution and oral absorption of Sprycel. In contrast, Dasatinib 100 mg Test Formulation can be expected to be less sensitive to such variations in various pH conditions.

Since dasatinib becomes practically insoluble at pH values higher than the normal acidic environment of the stomach, it is associated with DDI when administered with drugs that modulate acidity in the stomach (see Eley). The Sprycel Label states that concomitant use of ARAs such as H2 antagonists and PPIs should be avoided since clinical DDI studies have reported that a single dose of SPRYCEL 10 hours following famotidine (H2 antagonist) reduced the dasatinib mean plasma AUC by 61% and the mean Cmax by 63%. Similarly, a single 100 mg dose of Sprycel 22 hours following a 40 mg dose of omeprazole (PPI) at steady state reduced the dasatinib mean plasma AUC by 43% and the mean Cmax by 42%, see Sprycel Label. In addition, the Sprycel Label states that it should not be simultaneously administered with antacids, although antacids may be administered at least 2 hours prior to or 2 hours after Sprycel, see Sprycel Label.

The demonstrated DDI between Sprycel and ARAs have significant clinical implications which are further elaborated below.

Cancer patients frequently take ARAs to alleviate symptoms of gastroesophageal reflux disease despite the risk of a DDI which may significantly reduce the bioavailability of their anticancer therapy and subsequently result in reduced anti-tumor effect that potentially affects survival outcomes. The magnitude of this DDI is most pronounced for drugs whose in vitro solubility varies over the pH range 1 to 4, such as dasatinib. PPIs are the most potent ARAs, producing a rapid onset and prolonged duration of acid suppression, and are among the most common drug classes involved in DDIs with tyrosine kinase inhibitors (TKIs).

An increased incidence of chronic myeloid leukemia (CML) has recently been reported in a retrospective analysis of patients with a history of gastritis, dyspepsia, peptic ulcers, as well as among users of PPIs, which are all known proxies for *Helicobacter pylori* infections. A segment of CML patients with *H. pylori* etiology may need continued PPI therapy while receiving dasatinib, resulting in low and highly variable intestinal absorption of Sprycel under pH neutral intestinal luminal conditions.

PPI use following prescription of TKIs in the US has recently been evaluated in a retrospective claims database analysis of US SEER-Medicare data. It showed that 22% of all CML patients were treated with PPI during the first three months following a first prescription of a TKI (see Shara). A recent population matched registry study from Sweden which included 97% of all CML patients in the country found that 45% had at least one dispensed PPI between CML diagnosis and end of follow-up during the period 2005 to 2012. At two years on TKI treatment, the estimated cumulative incidence of PPI was 30% for any TKI, 28% for imatinib, 24% for dasatinib and 32% for nilotinib. In this study, the 5-year survival among PPI users was 78%, compared to 85% in non-users. The hazard ratio of death among PPI users compared to non-users was 1.6 (95% CI 1.1-2.3). Following adjustment for age, year of diagnosis, and comorbidity index, a 30% increase in mortality remained but was no longer significant (HR=1.3, 95% CI 0.9-1.9). If only PPI use in the first year following CML diagnosis was analyzed, the crude hazard ratio of death during follow-up was 1.5 (95% CI 1.0-2.1) and the adjusted hazard ratio was 1.2 (95% CI 0.8-1.8). The overall use of ARAs in patients with CML in this study is likely an underestimate since 19% of omeprazole and most H2 antagonists in Sweden are sold over the counter and not recorded by the registry.

In view of the findings that the 5-year survival among PPI users was 78%, compared to 85% in non-PPI users, one may conclude reasonably that the known interaction between dasatinib and an acid reduction agent (viz., ARA, e.g., omeprazole) provides for a reduced survival rate for ARA-users. As explained herein, concurrent administration of a therapeutically effective amount of an immediate release tablet disclosed herein and an ARA showed no drug-drug interaction between dasatinib and the ARA. Accordingly, an additional aspect of a method of treatment disclosed herein relates generally to an increased probability in patient survival over 5-years, compared to a Sprycel-treated patient, where the patient optionally undergoes concurrent ARA administration and where the probability of survival ranges from about 1% to about 10% and all values in between, including, for example, about 2%, about 3%, about 4%, about 5%, about 6%, about 7%, about 8%, and about 9%.

In view of the mortality hazard ratios and knowing that a hazard ratio (HR) may be used to assess the probability (P) of an occurrence, where P=HR/(1+HR) (see Spruance at 2790-2791), one may ascertain mortality probability based on the mortality hazard ratios. The observed mortality hazard ratios considered above shows that a PPI user has a probability of mortality of about 55% to about 62% over 5-years compared to non-PP I users. As explained herein, concurrent administration of a therapeutically effective amount of an immediate release tablet disclosed herein and an acid reduction agent (viz., ARA, e.g., omeprazole) showed no drug-drug interaction between dasatinib and the ARA. Also, as explained herein, administration of a therapeutically effective amount of an immediate release tablet disclosed herein reduces anomalously low dasatinib systemic exposure. Accordingly, a further aspect of a method of treatment disclosed herein relates generally to a reduction in the probability of mortality in a patient over 5-years, where the patient optionally undergoes concurrent ARA administration and where the probability of mortality ranges from about 5% to about 50% and all values in between, including, for example, about 10%, about 15%, about 20%, about 25%, about 30%, about 35%, about 40%, and about 45%, compared to a Sprycel-treated patient, and where the amount of dasatinib administered ranges of from about 5 to about 200 mg of dasatinib, including all values in between.

EXAMPLES

Example 1

A tablet was prepared based on the following recipe.

| Component | Quantity per Tablet (mg) | Quantity per Tablet (%) |
|---|---|---|
| Amorphous Solid Dispersion (ASD) | | |
| Dasatinib | 100.00 | 19.23 |
| Copovidone | 207.69 | 39.94 |
| Tablet Core | | |
| Sodium stearyl fumarate | 10.40 | 2.00 |
| Crospovidone | 44.00 | 8.46 |
| Mannitol | 38.69 | 7.44 |
| Sodium bicarbonate | 83.00 | 15.96 |
| Fumaric acid | 31.00 | 5.96 |
| Colloidal Silicon Dioxide | 2.60 | 0.50 |
| Sodium stearyl fumarate | 2.60 | 0.50 |
| Total per Tablet Core | 520 | 100 |
| Tablet Coating | | |
| Opadry ® White 03B28796 | 10.0 mg/tablet | |
| Total per Tablet | 530 mg | |

The amorphous solid dispersion and sodium stearyl fumarate were mixed in a diffusive mixer preparing dry mix I. This dry mix I was roller compacted to ribbons and thereafter screen sieved to granules. The granules, mannitol, crospovidone and co-sieved silicon dioxide, fumaric acid and sodium bicarbonate were mixed in a diffusive mixer preparing dry mix II. Dry mix II and sodium stearyl fumarate were mixed in a diffusive mixer preparing dry mix III. The dry mix III was compressed into tablets and the resulting tablets were spray coated.

Example 2

A tablet was prepared based on the following recipe, i.e. dry mixed, compacted, dry mixed, dry mixed, tableted and spray coated as described above for Example 1.

| Component | Quantity per Tablet (mg) | Quantity per Tablet (%) |
|---|---|---|
| Amorphous Solid Dispersion (ASD) | | |
| Dasatinib | 100.00 | 19.23 |
| Copovidone | 207.69 | 39.94 |
| Tablet Core | | |
| Sodium stearyl fumarate | 10.40 | 2.00 |
| Crospovidone | 38.10 | 7.33 |
| Mannitol | 72.80 | 14.00 |

-continued

| Component | Quantity per Tablet (mg) | (%) |
|---|---|---|
| Sodium bicarbonate | 62.40 | 12.00 |
| Succinic acid | 23.40 | 4.50 |
| Colloidal Silicon Dioxide | 2.60 | 0.50 |
| Sodium stearyl fumarate | 2.60 | 0.50 |
| Total per Tablet Core | 520 | 100 |

-continued

| Component | Quantity per Tablet (mg) | (%) |
|---|---|---|
| Tablet Coating | | |
| Opadry ® White 03B28796 | 10.0 mg/tablet | |
| Total per Tablet | 530 mg | |

Examples 3-18

A tablet was prepared based on the following recipe, i.e. dry mixed, compacted, dry mixed, dry mixed, compressed into tablets and spray coated as described above for Example 1. The amount of coating is proportional to the amount of dasatinib. 10.0 mg coating is applied to a tablet containing 100 mg dasatinib and for example 5.0 mg coating is applied to a tablet containing 50 mg dasatinib.

| Example | 3 | | 4 | | 5 | | 6 | |
|---|---|---|---|---|---|---|---|---|
| | mg | % | mg | % | mg | % | mg | % |
| Dasatinib | 100.00 | 19.23 | 100.00 | 19.23 | 100.00 | 19.23 | 100.00 | 19.23 |
| Copovidone | 207.69 | 39.94 | 207.69 | 39.94 | 207.69 | 39.94 | 207.69 | 39.94 |
| Sodium stearyl fumarate | 10.40 | 2.00 | 10.40 | 2.00 | 10.40 | 2.00 | 10.40 | 2.00 |
| Crospovidone | 22.00 | 4.23 | 44.00 | 8.46 | 38.12 | 7.33 | 43.31 | 8.33 |
| Mannitol | 60.68 | 11.67 | 95.68 | 18.40 | 72.80 | 14.00 | 67.60 | 13.00 |
| Sodium bicarbonate | 83.00 | 15.96 | 41.50 | 7.98 | 62.40 | 12.00 | 62.40 | 12.00 |
| Fumaric acid | 31.00 | 5.96 | 15.50 | 2.98 | 23.40 | 4.50 | 23.40 | 4.50 |
| Colloidal Silicon Dioxide | 2.60 | 0.50 | 2.60 | 0.50 | 2.60 | 0.50 | 2.60 | 0.50 |
| Sodium stearyl fumarate | 2.60 | 0.50 | 2.60 | 0.50 | 2.60 | 0.50 | 2.60 | 0.50 |
| Core total | 520 | 100 | 520 | 100 | 520 | 100 | 520 | 100 |

| Example | 7 | | 8 | | 9 | | 10 | |
|---|---|---|---|---|---|---|---|---|
| | mg | % | mg | % | mg | % | mg | % |
| Dasatinib | 100.00 | 19.23 | 100.00 | 19.23 | 100.00 | 19.23 | 100.00 | 19.23 |
| Copovidone | 207.69 | 39.94 | 207.69 | 39.94 | 207.69 | 39.94 | 207.69 | 39.94 |
| Sodium stearyl fumarate | 10.40 | 2.00 | 10.40 | 2.00 | 10.40 | 2.00 | 10.40 | 2.00 |
| Crospovidone | 43.3 | 8.3 | 43.3 | 8.3 | 43.3 | 8.3 | 43.3 | 8.3 |
| Mannitol | 67.6 | 13.0 | 44.8 | 8.6 | 8.1 | 1.6 | 67.6 | 13.0 |
| Sodium bicarbonate | 67.3 | 12.9 | 85.2 | 16.4 | 114.6 | 21.9 | 75.4 | 14.5 |
| Fumaric acid | 18.5 | 3.6 | 23.4 | 4.5 | 31.3 | 6.0 | 10.4 | 2.0 |
| Colloidal Silicon Dioxide | 2.60 | 0.50 | 2.60 | 0.50 | 2.60 | 0.50 | 2.60 | 0.50 |
| Sodium stearyl fumarate | 2.60 | 0.50 | 2.60 | 0.50 | 2.60 | 0.50 | 2.60 | 0.50 |
| Core total | 520 | 100 | 520 | 100 | 520 | 100 | 520 | 100 |

| Example | 11 | | 12 | | 13 | | 14 | |
|---|---|---|---|---|---|---|---|---|
| | mg | % | mg | % | mg | % | mg | % |
| Dasatinib | 100.00 | 19.23 | 100.00 | 19.23 | 100.00 | 19.23 | 100.00 | 19.23 |
| Copovidone | 207.69 | 39.94 | 207.69 | 39.94 | 207.69 | 39.94 | 207.69 | 39.94 |
| Sodium stearyl fumarate | 10.40 | 2.00 | 10.40 | 2.00 | 10.40 | 2.00 | 10.40 | 2.00 |
| Crospovidone | 43.3 | 8.3 | 43.3 | 8.3 | 43.3 | 8.3 | 43.3 | 8.3 |
| Mannitol | 67.6 | 13.0 | 44.2 | 8.5 | 52 | 10 | 62.4 | 12 |
| Sodium bicarbonate | 85.8 | 16.5 | 98.8 | 19 | 85.8 | 16.5 | 75.4 | 14.5 |

-continued

| | | | | | | | | |
|---|---|---|---|---|---|---|---|---|
| Fumaric acid | 0 | 0 | 10.4 | 2 | 15.6 | 3 | 15.6 | 3 |
| Colloidal Silicon Dioxide | 2.60 | 0.50 | 2.60 | 0.50 | 2.60 | 0.50 | 2.60 | 0.50 |
| Sodium stearyl fumarate | 2.60 | 0.50 | 2.60 | 0.50 | 2.60 | 0.50 | 2.60 | 0.50 |
| Core total | 520 | 100 | 520 | 100 | 520 | 100 | 520 | 100 |

| | 15 | | 16 | | 17 | | 18 | |
|---|---|---|---|---|---|---|---|---|
| Example | mg | % | mg | % | mg | % | mg | % |
| Dasatinib | 100.00 | 19.23 | 100.00 | 19.23 | 100.00 | 19.23 | 100.00 | 19.23 |
| Copovidone | 207.69 | 39.94 | 207.69 | 39.94 | 207.69 | 39.94 | 207.69 | 39.94 |
| Sodium stearyl fumarate | 10.40 | 2.00 | 10.40 | 2.00 | 10.40 | 2.00 | 10.40 | 2.00 |
| Crospovidone | 33.3 | 6.5 | 38.3 | 7.5 | 43.3 | 8.3 | 43.3 | 8.3 |
| Mannitol | 52.1 | 10.2 | 47.1 | 9.2 | 71.8 | 13.8 | 69.0 | 13.3 |
| Sodium bicarbonate | 85.8 | 16.8 | 85.8 | 16.8 | 62.4 | 12.0 | 50.0 | 9.6 |
| Fumaric acid | 15.6 | 3.1 | 15.6 | 3.1 | 19.3 | 3.7 | 34.5 | 6.6 |
| Colloidal Silicon Dioxide | 2.60 | 0.50 | 2.60 | 0.50 | 2.60 | 0.50 | 2.60 | 0.50 |
| Sodium stearyl fumarate | 2.60 | 0.50 | 2.60 | 0.50 | 2.60 | 0.50 | 2.60 | 0.50 |
| Core total | 520 | 100 | 520 | 100 | 520 | 100 | 520 | 100 |

| | 19 | | 20 | | 21 | | 22 | |
|---|---|---|---|---|---|---|---|---|
| Example | mg | % | mg | % | mg | % | mg | % |
| Dasatinib | 15.00 | 19.23 | 36.00 | 19.23 | 50.00 | 19.23 | 57.00 | 19.23 |
| Copovidone | 31.15 | 39.94 | 74.76 | 39.94 | 103.85 | 39.94 | 118.38 | 39.94 |
| Sodium stearyl fumarate | 1.56 | 2.00 | 3.74 | 2.00 | 5.20 | 2.00 | 5.93 | 2.00 |
| Crospovidone | 6.50 | 8.33 | 15.59 | 8.33 | 21.66 | 8.33 | 24.69 | 8.33 |
| Mannitol | 10.14 | 13.00 | 24.33 | 13.00 | 33.80 | 13.00 | 38.53 | 13.00 |
| Sodium bicarbonate | 9.36 | 12.00 | 22.46 | 12.00 | 31.20 | 12.00 | 35.57 | 12.00 |
| Fumaric acid | 3.51 | 4.50 | 8.43 | 4.50 | 11.70 | 4.50 | 13.34 | 4.50 |
| Colloidal Silicon Dioxide | 0.39 | 0.50 | 0.93 | 0.50 | 1.30 | 0.50 | 1.48 | 0.50 |
| Sodium stearyl fumarate | 0.39 | 0.50 | 0.93 | 0.50 | 1.30 | 0.50 | 1.48 | 0.50 |
| Core total | 78.00 | 100 | 187.20 | 100 | 260.00 | 100 | 296.40 | 100 |

| | 23 | | 24 | |
|---|---|---|---|---|
| Example | mg | % | mg | % |
| Dasatinib | 70.00 | 19.23 | 90.00 | 19.23 |
| Copovidone | 145.38 | 39.94 | 186.92 | 39.94 |
| Sodium stearyl fumarate | 7.28 | 2.00 | 9.36 | 2.00 |
| Crospovidone | 30.32 | 8.33 | 38.98 | 8.33 |
| Mannitol | 47.32 | 13.00 | 60.84 | 13.00 |
| Sodium bicarbonate | 43.68 | 12.00 | 56.16 | 12.00 |
| Fumaric acid | 16.38 | 4.50 | 21.06 | 4.50 |
| Colloidal Silicon Dioxide | 1.82 | 0.50 | 2.34 | 0.50 |
| Sodium stearyl fumarate | 1.82 | 0.50 | 2.34 | 0.50 |
| Core total | 364.0 | 100 | 468.0 | 100 |

CITED INFORMATION

Budha et al, *Drug absorption interactions between oral targeted anticancer agents and PPIs: is pH-dependent solubility the Achilles heel of targeted therapy?*, Clin. Pharmacol. Ther. (2012) 92(2): 203-213; DOI: 10.1038/clpt.2012.73; Epub: 27 Jun. 2012; PMID: 22739140; 2012 ("Budha").

Buehler G. *History of bioequivalence for critical dose drugs*, Office of Pharmaceutical Science, U.S. Food and Drug Administration, Archived Document, 2010 ("Buehler").

Chandani et al *Atypical pharmacokinetic profiles observed with dasatinib reference listed drug product in bioequivalence studies* American Association of Pharmaceutical Scientists (AAPS) Annual Meeting, San Diego, Nov. 12-15, 2017 (Poster M6107) ("Chandani").

Dasatinib Dissolution Method, www.accessdata.fda.gov/scripts/cder/dissolution searching for dasatinib, last accessed on Jan. 19, 2022.

Eley et al., *Phase I study of the effect of gastric acid pH modulators on the bioavailability of oral dasatinib in healthy subjects*, J. Clin. Pharmacol. (2009) 49(6): 700-709; DOI: 10.1177/0091270009333854; Epub 24 Apr. 2009; PMID: 19395585. ("Eley").

Guidance for Industry, *ANDAs: Stability Testing of Drug Substances and Products*, June 2013 ("GFI, Stability Testing").

Guidance for Industry, *Assessing the Effects of Food on Drugs in INDs and NDAs—Clinical Pharmacology Considerations*, February 2019 ("GFI, Assessing Food Effects").

Guidance for Industry, *Dissolution Testing and Acceptance Criteria for Immediate-Release Solid Oral Dosage Form Drug Products Containing High Solubility Drug Substances*, August 2018 ("GFI, Dissolution Testing").

Guidance for Industry, *Evaluation of Gastric pH-Dependent Drug Interactions With Acid-Reducing Agents: Study Design, Data Analysis, and Clinical Implications*, November 2020 ("GFI, Evaluation of Gastric pH").

Guidance for Industry, *Food-Effect Bioavailability and Fed Bioequivalence Studies*, December 2002 ("GFI, Food Effect").

Indini, *Impact of Use of Gastric-Acid Suppressants and Oral Anti-Cancer Agents on Survival Outcomes: A Systematic Review and Meta-Analysis*, Cancers (2020) 12(4): 998 (1-14). DOI: 10.3390/cancers12040998. Epub 2020 April 18. PMID: 32325628.

International Publication No. WO 2013/105895 A1, *A pharmaceutical composition comprising stable, amorphous hybrid nanoparticles of at least one protein kinase inhibitor and at least one polymeric stabilizing and matrix-forming component*, published on Jul. 18, 2013 to Brisander et al. of Xspray Microparticles AB ("Xspray WO895").

International Publication No. WO 2019/105894 A1, *A method for producing, stable, amorphous hybrid nanoparticles comprising at least one protein kinase inhibitor and at least one polymeric stabilizing and matrix-forming component*, published on Jul. 18, 2013 to Brisander et al. of Xspray Microparticles AB ("Xspray WO894").

Larfors et al. *Increased Risk of Chronic Myeloid Leukemia Following Gastric Conditions Indicating Helicobacter pylori Infection: A Case-Control Study*, Cancer Epidemiol. Biomarkers Prev. (2020) 29(1):151-156; DOI: 10.1158/1055-9965.EPI-19-0758; Epub 16 Oct. 2019; PMID: 31619405 ("Larfors").

Lassman et al., *Phase 2 trial of dasatinib in target-selected patients with recurrent glioblastoma (RTOG 0627)*, *Neuro-Oncology* (2015) 17(7): 992-998 ("Lassman").

Miura M., *Therapeutic drug monitoring of imatinib, nilotinib, and dasatinib for patients with chronic myeloid leukemia*, Biol. Pharm. Bull. (2015) 38(5): 645-654 ("Miura").

Pang et al., *Pharmacokinetics and absorption of the anticancer agents dasatinib and GDC-0941 under various gastric conditions in dogs—reversing the effect of elevated gastric pH with betaine HCl*, Mol. Pharm. (2013) 10(11): 4024-4031; DOI: Epub 11 Sep. 2013; PMID: 23980865 ("Pang").

Robbins J et al., *Dysphagia Research in the 21st Century and Beyond: Proceedings From Dysphagia Experts Meeting, Aug. 21, 2001*, J. Rehab. Res. Devel. (2001) 39(4): 543-548 ("Robbins").

Rousselot et al., *Dasatinib dose optimisation based on therapeutic drug monitoring reduces pleural effusion rates in chronic myeloid leukaemia patients*, Br. J. Haemotol. (2021) 194: 393-402 ("Rousselot").

Shara et al., *The concomitant use of tyrosine kinase inhibitors and proton pump inhibitors: Prevalence, predictors, and impact on survival and discontinuation of therapy in older adults with cancer*, Cancer (2019) 125(7): 1155-1162; DOI: 10.1002/cncr.31917; Epub 3 Jan. 2019; PMID: 30605231 ("Shara").

Smelick et al., *Prevalence of Acid-Reducing Agents (ARA) in Cancer Populations and ARA Drug-Drug Interaction Potential for Molecular Targeted Agents in Clinical Development*, Molecular Pharmaceutics (2013) 10(11): 4055-4062; DOI: doi.org/10.1021/mp400403s. Epub 13 Sep. 2013 ("Smelick").

Spruance et al., *Hazard Ratio in Clinical Trials*, Antimicrob Agents Chemother. (2004) 48(8): 2787-2792 ("Spruance").

Sprycel Prescribing Information for NDA 021986, Supplement 25 (Revised Jun. 29, 2021) ("Sprycel Label").

Sprycel Clinical Pharmacology and Biopharmaceutics Review for NDAs 21986 and 22072, Jun. 27, 2006 ("Sprycel Clinical Review").

U.S. Patent Application Publication No. US 2022/0233532 A1, *Fast Dissolving Pharmaceutical Compositions*, published on Jul. 28, 2022, to Brisander et al. of Xspray Pharma AB.

Wang et al., *Differential effects of dosing regimen on the safety and efficacy of dasatinib: retrospective exposure—response analysis of a Phase III study*, Clin. Pharmacol. (2013) 5(1): 85-97 ("Wang").

The subject matter of U.S. patent application Ser. No. 17/580,768, filed on Jan. 21, 2022 and U.S. Provisional Patent Application Nos. 63/140,003, filed on Jan. 21, 2021, and 63/288,752, filed on Dec. 13, 2021, is incorporated by reference in its entirety. Additionally, information cited herein is incorporated by reference. To the extent that incorporated subject matter conflicts with subject matter herein, the subject matter disclosed herein controls.

Additional Embodiments, Aspects, and Features

Embodiment A relates to a pharmaceutical formulation comprising an amorphous solid dispersion of dasatinib that is approximately 40% more bioavailable than Sprycel tablets containing dasatinib monohydrate.

A first aspect (A1) relates to a pharmaceutical formulation comprising an amorphous solid dispersion of dasatinib of about 100 mg of dasatinib that is bioequivalent to Sprycel 140 mg Tablets containing dasatinib monohydrate.

A second aspect (A2) relates to a pharmaceutical formulation comprising an amorphous solid dispersion of dasatinib of about 70 mg of dasatinib that is bioequivalent to Sprycel 100 mg Tablets containing dasatinib monohydrate.

A third aspect (A3) relates to a pharmaceutical formulation comprising an amorphous solid dispersion of dasatinib of about 57 mg of dasatinib that is bioequivalent to Sprycel 80 mg Tablets containing dasatinib monohydrate.

A fourth aspect (A4) relates to a pharmaceutical formulation comprising an amorphous solid dispersion of dasatinib of about 50 mg of dasatinib that is bioequivalent to Sprycel 70 mg Tablets containing dasatinib monohydrate.

A fifth aspect (A5) relates to a pharmaceutical formulation comprising an amorphous solid dispersion of dasatinib of about 36 mg of dasatinib that is bioequivalent to Sprycel 50 mg Tablets containing dasatinib monohydrate.

A sixth aspect (A6) relates to a pharmaceutical formulation comprising an amorphous solid dispersion of dasatinib of about 15 mg of dasatinib that is bioequivalent to Sprycel 20 mg Tablets containing dasatinib monohydrate.

Embodiment B relates to a pharmaceutical formulation comprising an amorphous solid dispersion of dasatinib that upon administration to subjects in the fasting state provides a significantly lesser variablitiy in median Tmax than a Sprycel tablet containing dasatinib monohydrate; 0.33-3.00 hr compared to 0.50-24 hr.

Embodiment C relates to a pharmaceutical formulation comprising an amorphous solid dispersion of dasatinib that has an intra-subject CV % for $AUC_{(0-24h)}$ approximately 3-fold less than a Sprycel tablet containing dasatinib monohydrate.

Embodiment D relates to a pharmaceutical formulation comprising an amorphous solid dispersion of dasatinib that has an intra-subject CV % for AUC(0-∞) approximately 2.5-fold less than a Sprycel tablet containing dasatinib monohydrate.

Embodiment E relates to a pharmaceutical formulation comprising an amorphous solid dispersion of dasatinib that has an intra-subject CV % for $C_{max}$ approximately 2-fold less than a Sprycel tablet containing dasatinib monohydrate.

Embodiment F relates to a pharmaceutical formulation comprising an amorphous solid dispersion of dasatinib that has an inter-subject CV % for $AUC_{(0-24h)}$ approximately 4.5-fold less than a Sprycel tablet containing dasatinib monohydrate.

Embodiment G relates to a pharmaceutical formulation comprising an amorphous solid dispersion of dasatinib that has an inter-subject CV % for $AUC_{(0-\infty)}$ approximately 4.3-fold less than a Sprycel tablet containing dasatinib monohydrate.

Embodiment H relates to a pharmaceutical formulation comprising an amorphous solid dispersion of dasatinib that has an inter-subject CV % for $C_{max}$ approximately 4.8-fold less than a Sprycel tablet containing dasatinib monohydrate.

Embodiment I relates to a pharmaceutical formulation comprising an amorphous solid dispersion of dasatinib that is absence of food effect on its extent of exposure (Fed/Fast AUCt ratios within ±5% versus±15% for a Sprycel tablet containing dasatinib monohydrate).

Embodiment J relates to a pharmaceutical formulation comprising an amorphous solid dispersion of dasatinib with the absence of drug-drug interaction (DDI) with an antacid (e.g., aluminum hydroxide gel, calcium carbonate, magnesium hydroxide, etc.), an H2 antagonist (e.g., famotidine, cimetidine, nizatidine, ranitidine, etc.) a PPI (e.g., omeprazole, rapeprazole, esomeprazole, lansoprazole, pantoprazole, dexlansoprazole, etc.).

Embodiment K relates to a pharmaceutical formulation comprising an amorphous solid dispersion of dasatinib that does not exhibit anomalously low systemic exposure profiles, which the EMA has referred to as "low-tier" patient profiles, when compared with a Sprycel tablet containing dasatinib monohydrate.

Embodiment L relates to a pharmaceutical formulation comprising an amorphous solid dispersion comprising 100 mg dasatinib by weight of the formulation, wherein administering to a subject the amorphous solid dispersion provides a maximum plasma concentration of about 241±29 ng/mL (intersubject variability).

Embodiment M relates to a pharmaceutical formulation comprising an amorphous solid dispersion comprising 100 mg dasatinib by weight of the formulation, wherein administering to a subject the amorphous solid dispersion provides a maximum plasma concentration of about 241±70 ng/mL (intrasubject variability).

Embodiment N relates to a pharmaceutical formulation comprising an amorphous solid dispersion comprising 100 mg dasatinib by weight of the formulation, wherein administering to a subject the amorphous solid dispersion provides an area under the plasma drug concentration curve AUC(0-∞) of 877±79 ng·hr/mL (intersubject variability).

Embodiment O relates to a pharmaceutical formulation comprising an amorphous solid dispersion comprising 100 mg dasatinib by weight of the formulation, wherein administering to a subject the amorphous solid dispersion provides an area under the plasma drug concentration curve AUC(0-∞) of 877±123 ng·hr/mL (intrasubject variability).

In another aspect, there is provided a method of treating a proliferative disorder in a patient in need thereof, comprising administering a therapeutically effective amount of a composition according to any one of Embodiments A to O and/or any Aspects thereof (e.g., Aspects A1 to A6).

Feature 1. An immediate release pharmaceutical composition in the form of a non-effervescent tablet, comprising: (a) particles comprising (i) dasatinib in an amount of about 10% by weight to about 70% by weight of the particles; and (ii) at least one polymeric stabilizing and matrix-forming component; (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight.

Feature 2. The pharmaceutical composition of Feature 1, wherein the particles are solid dispersion particles.

Feature 3. The pharmaceutical composition of any one of Features 1-2, wherein dasatinib is 100% amorphous.

Feature 4. The pharmaceutical composition of any one of Features 1-3, wherein the gas generating agent is selected from a group consisting of sodium carbonate, potassium carbonate, sodium bicarbonate, potassium bicarbonate, sodium sulfite, potassium sulfite, an ammonium cation, and a combination thereof.

Feature 5. The pharmaceutical composition of any one of Features 1-4, wherein the gas generating agent is selected from a group consisting of sodium bicarbonate, potassium bicarbonate, and a combination thereof.

Feature 6. The pharmaceutical composition of any one of Features 1-5, wherein the acidic pH modifier is selected from a group consisting of sorbic acid, adipic acid, succinic acid, fumaric acid, tartaric acid, and a combination thereof.

Feature 7. The pharmaceutical composition of any one of Features 1-6, wherein the mole ratio of the gas generating agent to the acidic pH-modifier ranges from about 4:1 to about 1:4.

Feature 8. The pharmaceutical composition of any one of Features 1-7, wherein the disintegrating agent comprises crospovidone.

Feature 9. The pharmaceutical composition of any one of Features 1-8, wherein the pharmaceutical composition comprises dasatinib in an amount of about 15 mg, about 36 mg, about 50 mg, about 57 mg, about 70 mg, or about 100 mg.

Feature 10. A method of treating a disorder in a patient in need thereof, comprising administering a therapeutically effective amount of the composition of any one of Features 1-9 to the patient, wherein said proliferative disorder is newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and adults with Philadelphia chromosome-positive acute lymphoblastic leukemia (Ph+ ALL) with resistance or intolerance to prior therapy.

Feature 11. The method of Feature 10, wherein an amount of dasatinib in the pharmaceutical composition comprises 15 mg, 36 mg, 50 mg, 57 mg, 70 mg, or 100 mg.

Feature 12. The method of Feature 10, wherein a dasatinib dose of X achieves bioequivalence to a dasatinib dose of Y for Sprycel, wherein X and Y are respectively selected from (i) 15 mg (X) and 20 mg (Y), (ii) 36 mg (X) and 50 mg (Y), (iii) 50 mg (X) and 70 mg (Y), (iv) 57 mg (X) and 80 mg (Y), (v) 70 mg (X) and 100 mg (Y), and (vi) 100 mg (X) and 140 mg (Y).

Feature 13. The method of Feature 10, wherein a dasatinib dose of 100 mg provides a Cmax of about 241 ng/mL.

Feature 14. The method of Feature 10, wherein a dasatinib dose of 100 mg provides an AUC(0-∞) of about 877 ng·hr/mL Feature 15. The method of Feature 10, wherein a dasatinib dose of 100 mg provides a Cmax of about 241 ng/mL and an intersubject coefficient of variation of about 12%.

Feature 16. The method of Feature 10, wherein a dasatinib dose of 100 mg provides a Cmax of about 241 ng/mL and an intrasubject coefficient of variation of about 29%.

Feature 17. The method of Feature 10, wherein a dasatinib dose of 100 mg provides an AUC(0-∞) of about 877 ng·h/mL and an intersubject coefficient of variation of about 9%.

Feature 18. The method of Feature 10, wherein a dasatinib dose of 100 mg provides an AUC(0-∞) of about 877 ng·h/mL and an intrasubject coefficient of variation of about 14%.

Feature 19. The method of Feature 10, wherein a dasatinib dose of 100 mg provides an $AUC_{(0\text{-}24h)}$ fed/$AUC_{(0\text{-}24h)}$ fasted ratio of from about 95% to about 100%, wherein AUC(0-24h) fed corresponds to the least-squares geometric mean of the $AUC_{(0\text{-}24h)}$ in fed patients and wherein $AUC_{(0\text{-}24h)}$ fasted corresponds to the least-squares geometric mean of the $AUC_{(0\text{-}24h)}$ in fasted patients.

Feature 20. The method of Feature 10 further comprising co-administering an acid reducing agents (ARA) comprising antacid, an H2 antagonist, or a proton pump inhibitor.

The invention claimed is:

1. A method for reducing pleural effusion in a patient suffering from a proliferative disorder, comprising:

administering a therapeutically effective amount of a pharmaceutical composition comprising dasatinib as an amorphous solid dispersion, wherein:

(a) the pharmaceutical composition is administered at a dasatinib dose that is 20% to 30% lower than a dose of a conventional crystalline dasatinib formulation required to deliver a therapeutically effective amount of dasatinib under fasted conditions; and (b) administration of the pharmaceutical composition results in at least a 20% reduction in intra-subject variability of a minimum plasma concentration (Cmin) of dasatinib, as measured by coefficient of variation (CV %), relative to administration of a therapeutically effective amount of the conventional crystalline dasatinib formulation under fasted conditions.

2. The method of claim 1, wherein the pharmaceutical composition, comprises: (a) particles comprising (i) dasatinib in an amount of about 10% by weight to about 70% by weight of the particles; and (ii) at least one polymeric stabilizing and matrix-forming component.

3. The method of claim 2, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight.

4. The method of claim 2, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight and wherein the gas generating agent is selected from a group consisting of sodium carbonate, potassium carbonate, sodium bicarbonate, potassium bicarbonate, sodium sulfite, potassium sulfite, an ammonium cation, and a combination thereof.

5. The method of claim 2, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight and wherein the gas generating agent is selected from a group consisting of sodium bicarbonate, potassium bicarbonate, and a combination thereof.

6. The method of claim 2, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight and wherein the acidic pH modifier is selected from a group consisting of sorbic acid, adipic acid, succinic acid, fumaric acid, tartaric acid, and a combination thereof.

7. The method of claim 3, wherein the mole ratio of the gas generating agent to the acidic pH-modifier ranges from about 4:1 to about 1:4.

8. The method of claim 3, wherein the disintegrating agent comprises crospovidone.

9. The method of claim 1, wherein the pharmaceutical composition comprises dasatinib in an amount of about 15 mg, about 36 mg, about 50 mg, about 57 mg, about 70 mg, or about 100 mg.

10. The method of claim 1, where the proliferative disorder is selected from newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and adults with Philadelphia chromosome-positive acute lymphoblastic leukemia (Ph+ ALL) with resistance or intolerance to prior therapy.

11. A method for reducing pleural effusion in a patient suffering from a proliferative disorder, comprising:

administering a therapeutically effective amount of a pharmaceutical composition comprising dasatinib as an amorphous solid dispersion, wherein (a) the pharmaceutical composition is administered at a dasatinib dose that is 20% to 30% lower than a dose of a conventional crystalline dasatinib formulation required to deliver a therapeutically effective amount of dasatinib under fasted conditions;

(b) administration of the pharmaceutical composition results in at least a 20% reduction in intra-subject variability of a minimum plasma concentration (Cmin) of dasatinib, as measured by coefficient of variation (CV %), relative to administration of a therapeutically effective amount of the conventional crystalline dasatinib formulation under fasted conditions; and (c) systemic exposure of dasatinib, as measured by AUC (0-24 h), is within 80% to 125% of the systemic exposure following administration of the conventional crystalline dasatinib formulation.

12. The method of claim 11, wherein the pharmaceutical composition, comprises: (a) particles comprising (i) dasatinib in an amount of about 10% by weight to about 70% by weight of the particles; and (ii) at least one polymeric stabilizing and matrix-forming component.

13. The method of claim 12, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight.

14. The method of claim 12, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight and wherein the gas generating agent is selected from a group consisting of sodium carbonate, potassium carbonate, sodium bicarbonate, potassium bicarbonate, sodium sulfite, potassium sulfite, an ammonium cation, and a combination thereof.

15. The method of claim 12, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight and wherein the gas generating agent is selected from a group consisting of sodium bicarbonate, potassium bicarbonate, and a combination thereof.

16. The method of claim 12, wherein the pharmaceutical composition further comprises (b) at least one disintegrant agent in an amount of about 4% by weight to about 16% by weight; (c) at least one gas generating agent in an amount of about 8% by weight to about 22% by weight; and (d) at least one acidic pH modifier in an amount of about 2% by weight to about 6% by weight and wherein the acidic pH modifier is selected from a group consisting of sorbic acid, adipic acid, succinic acid, fumaric acid, tartaric acid, and a combination thereof.

17. The method of claim 13, wherein the mole ratio of the gas generating agent to the acidic pH-modifier ranges from about 4:1 to about 1:4.

18. The method of claim 13, wherein the disintegrating agent comprises crospovidone.

19. The method of claim 11, wherein the pharmaceutical composition comprises dasatinib in an amount of about 15 mg, about 36 mg, about 50 mg, about 57 mg, about 70 mg, or about 100 mg.

20. The method of claim 11, where the proliferative disorder is selected from newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and adults with Philadelphia chromosome-positive acute lymphoblastic leukemia (Ph+ ALL) with resistance or intolerance to prior therapy.

* * * * *